United States Patent [19]

Schoenleber et al.

[11] Patent Number: 4,994,486
[45] Date of Patent: Feb. 19, 1991

[54] DOPAMINERGIC COMPOUNDS

[75] Inventors: Robert W. Schoenleber, Deerfield; John W. Kebabian, Lake Bluff; Michael P. DeNinno, Wildwood; Michael R. Michaelides, Highland Park; Sheela A. Thomas, Vernon Hills, all of Ill.

[73] Assignee: Abbott Laboratories, Abbott Park, Ill.

[21] Appl. No.: 456,011

[22] Filed: Dec. 22, 1989

Related U.S. Application Data

[63] Continuation-in-part of Ser. No. 359,448, May 31, 1989, Pat. No. 4,963,568.

[51] Int. Cl.$^5$ ............... A61K 31/35; C07D 333/64; C07D 277/22; C07D 405/00
[52] U.S. Cl. .................... 514/456; 549/406; 549/407; 549/59; 546/269; 540/596; 544/336; 548/203; 548/206
[58] Field of Search ............ 549/407, 406, 59; 514/456; 546/269; 540/596; 544/336; 548/203, 206

Primary Examiner—Mary C. Lee
Assistant Examiner—Joseph K. McKane
Attorney, Agent, or Firm—Jerry F. Janssen; Steven F. Weinstock

[57] ABSTRACT

Novel compounds of Formula (I):

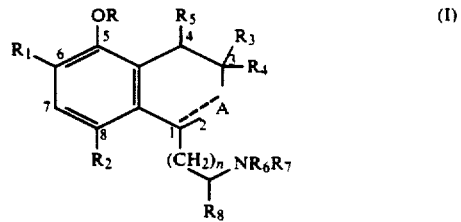

or pharmaceutically acceptable salts, esters and amides thereof, wherein A is O, C, CH or $CH_2$, n is 0 or 1, and the dotted line is a single bond when A is O or $CH_2$ and a double bond when A is CH or when n=0, A is C and $R_6$ and A taken together form a nitrogen-containing heterocycle;

R is hydrogen, lower alkyl or a readily cleavable group;

$R_1$ is selected from hydrogen, halogen, lower alkyl, haloalkyl and lower alkoxy;

$R_2$ is selected from hydrogen, halogen, lower alkyl and haloalkyl or, taken together with $R_8$, forms a fused ring;

$R_3$ is hydrogen, alkyl, alkenyl, alkynyl, cycloalkyl, aryl or arylalkyl or, taken together with $R_4$, forms a spirocycloalkyl or, taken together with $R_5$, forms a fused cycloalkyl;

$R_4$ is hydrogen or alkyl or, taken together with $R_3$, forms a spirocycloalkyl;

$R_5$ is hydrogen or alkyl or, taken together with $R_3$, forms a fused cycloalkyl;

$R_6$ is hydrogen, alkyl, alkenyl, alkynyl, cycloalkyl or arylalkyl or, taken together with A when A is C and when n is 0, forms a fused nitrogen-containing heterocycle or, taken together with $R_7$ or $R_8$, forms a nitrogen-containing heterocycle;

$R_7$ is hydrogen or alkyl or, taken together with $R_6$ or $R_8$, forms a nitrogen-containing heterocycle;

$R_8$ is hydrogen or alkyl or, taken together with $R_6$ or $R_7$, forms a nitrogen-containing heterocycle or, taken together with $R_2$, forms a fused ring, with the proviso that $R_3$ and $R_4$ cannot simultaneously both be hydrogen, are selective dopaminergic agents and are useful for treating disorders characterized by abnormal dopaminergic activity in the central or the peripheral nervous system, for example, neurological disorders such as psychoses, Parkinson's Disease, certain cardiovascular disorders and addictive behavior disorders.

16 Claims, No Drawings

DOPAMINERGIC COMPOUNDS

This application is a continuation-in-part of copending U.S. application Ser. No. 359,448, filed May 31, 1989 now U.S. Pat. No. 4963568.

TECHNICAL FIELD

This invention relates to novel compounds which are selective dopaminergic agents. These compounds are potentially useful for treating disorders characterized by abnormal dopamine levels, such as schizophrenia and other neurological disorders such as Parkinson's Disease, as well as for treating various forms of addictive behavior and certain cardiovascular disorders.

BACKGROUND OF THE INVENTION

Dopamine is an important neurotransmitter in the central nervous system (CNS), and also has several important roles in the peripheral nervous system such as in the control of supply of blood to the kidneys and in autonomic ganglion transmission.

It is now widely accepted that dopamine receptors in the CNS can be divided into two general categories, designated D-1 and D-2 receptors. The division was originally based on biochemical and pharmacological differences between the two receptor types. Recently, further evidence which supports this division has come from study of the molecular biology of dopamine receptors in the CNS. The dopamine D-1 receptor is linked to the enzyme adenylate cyclase through a stimulatory G protein such that stimulation of this receptor by dopamine or a dopamine D-1 receptor agonist causes an increase in the production of 3',5'-cyclic adenosine monophosphate (cAMP). The D-2 receptor, on the other hand, also regulates important functional activity within the CNS, although the biochemical events which follow stimulation of this receptor by dopamine or a D-2 receptor agonist are not as well understood. Autoreceptors on dopaminergic neurons which have the pharmacological properties of D-2 receptors appear to control the firing rate of these cells as well as the release of dopamine from the nerve terminals. It is also known that stimulation of the D-2 receptors in the intermediate lobe of the pituitary gland causes a decrease in cAMP production and that stimulation of the D-2 receptors on the mammotrophs of the anterior pituitary gland suppresses prolactin secretion. Dopaminergic neurons are also affected by and interact with other neurotransmitter systems in the CNS. For example, D-2 receptors on the cholinergic interneurons in the striatum (one of the components of the basal ganglia) regulate the release of acetylcholine from these cells.

Dopamine involvement has been proposed for several diverse neurological disorders such as Parkinson's disease and schizophrenia. The putative roles of the two types of dopamine receptors differ in these disorders.

One neuropathology involving dopamine is Parkinson's Disease. Dopamine occurs at high concentration within the nerve terminals in the basal ganglia of the mammalian brain. In the early 1960's, the loss of striatal dopamine was established as a chemical marker of Parkinson's Disease. This deficiency is still thought to be primary to the etiology of the disease state.

L-DOPA (3,4-dihydroxyphenylalanine), which is used in conjunction with a peripheral aromatic amino acid decarboxylase inhibitor and often supplemented with anticholinergic agents, has been shown to be useful in the treatment of Parkinson's Disease. It is theorized that the response to L-DOPA is a result of the conversion of L-DOPA to dopamine within the striatum, and that the response is linked to stimulation of both the D-1 and D-2 receptors.

The success of L-DOPA therapy has led to the testing of other compounds capable of mimicking the post-synaptic receptor actions of dopamine. Such direct-acting agents might offer the therapeutic advantages of greater potency, increased duration of action, or fewer side effects over L-DOPA. For example, bromocryptine, the direct-acting dopamine agonist most widely used in the treatment of Parkinson's disease, lowers the amount of L-DOPA required to achieve the maximal therapeutic response and allows for a delay in the onset of L-DOPA therapy. However, the response to bromocryptine alone is not as great as that observed with L-DOPA.

Dopamine has been used in the treatment of shock, congestive heart failure and renal failure. Stimulation of the peripheral DA-1 receptors causes vasodilation, particularly in the renal and mesenteric vascular beds where large numbers of these receptors are found. The utility of dopamine has been limited, however, by its ability to cause vasoconstriction at higher concentrations, presumably due to its secondary effects on adrenergic receptors and by its emetic effects due to peripheral DA-2 stimulation. Agents selective for the peripheral DA-1 receptors may offer significant advantages over currently used treatments for these and other disorders.

A second neurological disorder in which dopamine has been implicated is the psychosis schizophrenia. The psychoses are serious psychiatric illnesses characterized by abnormal behavior which may include delusions, hallucinations, violence, mania and serious long-lasting depression. Schizophrenia is the most common psychosis and involves disturbance of thought processes, hallucinations and loss of touch with reality. The theory of schizophrenia as a disease of the CNS was first formalized by Kraepelin and Bleuler in the early 1900's. It was not until chlorpromazine was discovered by Delay and Daniker in the early 1950's, however, that effective drug management of this disease was possible.

The pioneering work of Carlsson and others led to the now widely-held dopamine theory of schizophrenia. According to this theory, schizophrenia is caused by an excess of dopamine in the brain. Several line of evidence support this hypothesis. For example, chronic abuse of stimulants such as amphetamines, known to enhance dopaminergic activity in the brain, can lead to a paranoid psychosis that is almost indistinguishable from classic paranoid schizophrenia. The mechanism-of-action proposed for drugs with antischizophrenic activity is the blockade by these compounds of the dopamine receptors, and consequently, the prevention of excess receptor stimulation. In the mid 1970's it was observed that virtually all of the currently used antipsychotic agents could displace radiolabeled haloperidol (a dopamine antagonist) from striatal dopamine receptors with a good correlation between average effective clinical dose and drug binding affinity.

Unfortunately, the currently available antipsychotic agents frequently produce undesirable side-effects, the most common of which are the so-called extrapyramidal effects that include bizarre involuntary movements and Parkinson-like effects. Sedation and hypotension are also common side effects. Because of these often severe side-effects and the high incidence of patients unresponsive to currently available drugs, more potent and selective agents are needed.

Published evidence suggests that dopamine also has a central role in the brain's reward system. In particular, it has been reported that animals trained to self-administer cocaine will increase their consumption of this drug after treatment with either a D-1 or a D-2 receptor antagonist. It was proposed that the animals would increase the amount of cocaine administered in order to maintain the elevated dopamine levels responsible for the drugs euphorigenic and reinforcing properties. Because of this interrelationship, dopamine antagonists are potentially useful for the treatment of drug abuse and other addictive behavior disorders.

SUMMARY OF THE INVENTION

The compounds of the present invention are dopaminergic compounds represented by the following structural formula (I):

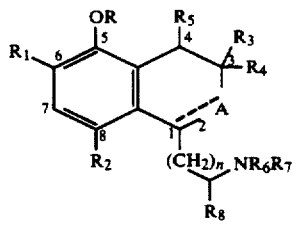

or pharmaceutically acceptable salts, esters and amides thereof,
wherein A is O, C, CH or $CH_2$, n is 0 or 1, and the dotted line is a single bond when A is O or $CH_2$ and a double bond when A is CH or when n=0, A is C and $R_6$ and A taken together form a nitrogen-containing heterocycle.

R is hydrogen, lower alkyl or a readily cleavable group.

$R_1$ is selected from hydrogen, halogen, lower alkyl, haloalkyl and lower alkoxy.

$R_2$ is selected from hydrogen, halogen, lower alkyl and haloalkyl or, taken together with $R_8$, forms a fused ring.

$R_3$ is hydrogen, alkyl, alkenyl, alkynyl, cycloalkyl, aryl or arylalkyl or, taken together with $R_4$, forms a spirocycloalkyl or, taken together with $R_5$, forms a fused cycloalkyl.

$R_4$ is hydrogen or alkyl or, taken together with $R_3$, forms a spirocycloalkyl.

$R_5$ is hydrogen or alkyl or, taken together with $R_3$, forms a fused cycloalkyl.

$R_6$ is hydrogen, alkyl, alkenyl, alkynyl, cycloalkyl or, taken together with A when A is C and when n is 0, forms a fused nitrogen-containing heterocycle or, taken together with $R_7$ or $R_8$, forms a nitrogen-containing heterocycle.

$R_7$ is hydrogen or alkyl or, taken together with $R_6$ or $R_8$, forms a nitrogen-containing heterocycle.

$R_8$ is hydrogen or alkyl or, taken together with $R_6$ or $R_7$, forms a nitrogen-containing heterocycle or, taken together with $R_2$, forms a fused ring.

These compounds are subject to the proviso that $R_3$ and $R_4$ cannot simultaneously both be hydrogen.

It has been found that the compounds of Formula I have the ability to act on dopamine receptors in the central and peripheral nervous systems. The compounds of the present invention are, therefore, potentially useful in the treatment of dopamine-related neurological and cardiovascular disorders as well as in the treatment of addictive behavior disorders.

DETAILED DESCRIPTION OF THE INVENTION

This invention relates to novel compounds which are selective dopaminergic agents. More particularly, this invention relates to compounds of the following Formula (I):

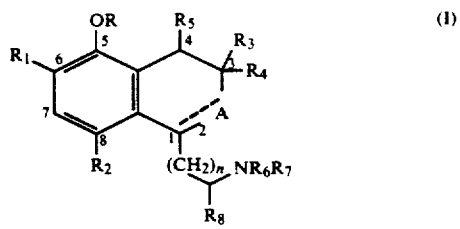

wherein A is O, C, CH or $CH_2$, n is 0 or 1, and
the dotted line is a single bond when A is O or $CH_2$ and a double bond when A is CH or when n=0, A is C and $R_6$ and A taken together form a nitrogen-containing heterocycle;

R is hydrogen, lower alkyl or a readily cleavable group; $R_1$ is selected from hydrogen, halogen, lower alkyl, haloalkyl and lower alkoxy;

$R_2$ is selected from hydrogen, halogen, lower alkyl and haloalkyl or, taken together with $R_8$, forms a fused ring;

$R_3$ is hydrogen, alkyl, alkenyl, alkynyl, cycloalkyl, aryl or arylalkyl or, taken together with $R_4$, forms a spirocycloalkyl or, taken together with $R_5$, forms a fused cycloalkyl;

$R_4$ is hydrogen or alkyl or, taken together with $R_3$, forms a spirocycloalkyl;

$R_5$ is hydrogen or alkyl or, taken together with $R_3$, forms a fused cycloalkyl;

$R_6$ is hydrogen, alkyl, alkenyl, alkynyl, cycloalkyl or arylalkyl or, taken together with A when A is C and when n is 0, forms a fused nitrogen-containing heterocycle or, taken together with $R_7$ or $R_8$, forms a nitrogen-containing heterocycle;

$R_7$ is hydrogen or alkyl or, taken together with $R_6$ or $R_8$, forms a nitrogen-containing heterocycle; and $R_8$ is hydrogen or alkyl or, taken together with $R_6$ or $R_7$, forms a nitrogen-containing heterocycle or, taken together with $R_2$, forms a fused ring;

or pharmaceutically acceptable salts, esters and amides thereof, subject to the proviso that $R_3$ and $R_4$ cannot simultaneously both be hydrogen.

The present invention also relates to compositions comprising a therapeutically effective amount of the compound of Formula (I) and a pharmaceutically acceptable carrier or diluent.

The present invention also relates to the use of the compounds of Formula (I) in the treatment of dopamine related disorders.

The following compounds are representative of the preferred compounds of Formula (I):
1-Aminomethyl-5-hydroxy-3-phenyl-3,4-dihydronaphthalene;
1-Aminomethyl-5-acetoxy-3-phenyl-3,4-dihydronaphthalene;

1-Aminomethyl-5-t-butylacetoxy-3-phenyl-3,4-dihydronaphthalene;

[1R,3S] 1-Aminomethyl-5-hydroxy-3-phenyl-1,2,3,4-tetrahydronaphthalene;

1-Aminomethyl-5-hydroxy-6-methoxy-3-phenyl-3,4-dihydronaphthalene;

[1R,3S] 1-Aminomethyl-3-cyclohexyl-3,4-dihydro-5-hydroxy-6-methyl-1H-2-benzopyran;

[1R,3S] 1-(N,N-Dimethyl)-aminomethyl-3-cyclohexyl-3,4-dihydro-5-hydroxy-6-methyl-1H-2-benzopyran;

[1R,3S] 1-(N-Methyl)-aminomethyl-3-cyclohexyl-3,4-dihydro-5-hydroxy-6-methyl-1H-2-benzopyran;

[1R,3S] 1-Aminomethyl-6-bromo-3,4-dihydro-5-hydroxy-3-phenyl-1H-2-benzopyran;

[1R,3R] 1-Aminomethyl-6-bromo-3,4-dihydro-5-hydroxy-3-phenyl-1H-2-benzopyran;

[1R,3S] 1-Aminomethyl-3,4-dihydro-5-hydroxy-3-phenyl-1H-2-benzopyran;

[1R,3R] 1-(N-Methyl)-aminomethyl-6-bromo-3,4-dihydro-5-hydroxy-3-phenyl-1H-2-benzopyran.

[1R,3S] 1-Aminomethyl-3,4-dihydro-5,6-dimethoxy-3-phenyl-1H-2-benzopyran;

[1R,3S] 1-Aminomethyl-3,4-dihydro-5-hydroxy-6-methoxy-3-phenyl-1H-2-benzopyran.

Contemplated equivalents of the compounds of general Formula (I) are compounds otherwise corresponding thereto and having the same general properties wherein one or more of $R_1$, $R_2$, $R_3$, etc. are simply variations of the substituents as defined herein. As will be apparent, where a substituent can be a hydrogen atom, the exact chemical nature of a substituent which is other than hydrogen at that position is not critical, so long as it does not adversely affect the efficacy of the compound.

Certain compounds of this invention exist in optically active forms. The pure d isomers and pure l isomers, as well as mixtures thereof including the racemic mixtures, are contemplated by this invention. Additional asymmetric centers may be present in a substituent such as an alkyl group. All such isomers as well as mixtures thereof are intended to be within the scope of this invention. In particular, stereochemistry of the substituents at the 1 and 3 positions, as shown in Formula (I), can independently be either axial or equatorial unless specifically noted otherwise.

The term "addictive behavior" is used herein to mean symptoms and maladaptive behavioral changes associated with periodic or continued use of psychoactive substances. These behavioral changes, for example, continued compulsive use of the psychoactive substance despite the presence of persistent or recurrent social, occupational, psychological or physical problems that the person knows are caused by or may be exacerbated by continued use of the substance, would be viewed as extremely undesirable in almost all cultures.

The term "administration" of the dopaminergic agent or composition, as used herein, refers to systemic use as when taken orally, parenterally, by inhalation spray, by nasal, rectal or buccal routes, or topically in dosage form unit formulations containing conventional non-toxic pharmaceutically acceptable carriers, adjuvants and vehicles as desired.

The term "alkenyl" is used herein to mean straight or branched chain radicals of one to twelve carbon atoms containing at least one double bond. Representative of such radicals are ethenyl, n-propenyl, isopropenyl, n-butenyl, isobutenyl, 2-ethylhexenyl, n-octenyl, 2,4-dimethylpentenyl, and the like. These can be unsubstituted, or they can be substituted, for example, with lower alkyl, cycloalkyl, or with aryl or arylalkyl groups, or with heteroatoms such as N or O, or with a heterocycle such as pyrrolidinyl, piperidinyl and the like, provided that any such substituent not interfere with the efficacy of the compound.

The term "alkyl" is used herein to mean straight or branched chain radicals of one to twelve carbon atoms. Representative of such radicals are methyl, ethyl, n-propyl, isopropyl, n-butyl, sec-butyl, isobutyl, t-butyl, 2-ethylhexyl, n-octyl, 2,4-dimethylpentyl, and the like. These can be unsubstituted, or they can be substituted, for example, with lower alkyl, cycloalkyl, or with aryl or arylalkyl groups, or with heteroatoms such as N or O, or with a heterocycle such as pyrrolidinyl, piperidinyl and the like, provided that any such substituent not interfere with the efficacy of the compound.

The term "alkynyl" is used herein to mean straight or branched chain radicals of one to twelve carbon atoms containing at least one triple bond. Representative of such radicals are ethynyl, n-propynyl, butynyl, 3-ethylhexynyl, n-octynyl, 4-methylpentynyl, and the like. These can be unsubstituted, or they can be substituted, for example, with lower alkyl, cycloalkyl, or with aryl or arylalkyl groups, or with heteroatoms such as N or O, or with a heterocycle such as pyrrolidinyl, piperidinyl and the like, provided that any such substituent not interfere with the efficacy of the compound.

The terms "amino acid" and "polypeptide residue" refer to a single amino acid or two or more amino acids joined by amide (peptide) bonds. The amino acids can be naturally occurring amino acids such as valine or glycine or phenylalanine or they may be synthetic amino acids such as cyclohexylalanine. The amino acids can either be in the L or D configuration or a mixture of the two isomers. If not specified, amino acid substituents are optically active and have the L configuration.

The term "antipsychotic agent" as used herein refers to drugs used extensively in the symptomatic management of all forms of schizophrenia, organic psychosis, the manic phase of manic depressive illness and other acute idiopathic illnesses and occasionally used in depression or in severe anxiety.

The term "aryl" as used herein refers to aromatic radicals having five to six atoms in a single ring system which may contain one to three heteroatoms selected from N, O and S, the remaining atoms being carbon atoms. Representative aromatic radicals include phenyl, pyridyl, pyrazinyl, thiazoyl, furyl, and thienyl. Further, the single ring system may be substituted to form a multiple fused ring system, for example, 1-naphthyl, 2-naphthyl, and the like. These compounds may be unsubstituted; or they may be substituted with one or more non-hydrogen substituents for example, hydroxy, halogen, lower alkyl or lower alkoxy, provided that any such substituent not interfere with the efficacy of the compound.

The term "arylalkyl" is used herein to mean straight or branched chain radicals of one to twelve carbon atoms which are substituted with an aryl group. Representative arylalkyl groups include benzyl and phenylethyl groups.

The term "catechol-protecting groups" as used herein refers to groups used to derivatize catechol hydroxyl oxygen atoms in order to prevent undesired reactions or degradation during a synthesis. These derivatizing groups can be selected from phenol-protecting groups as defined below or they may be selected from those groups which are suitable for the protection of catechols because of the proximity of the two hydroxyl functions. Commonly used catechol-protecting groups include dimethyl ethers, dibenzyl ethers, cyclohexylidene ketals, methylene acetals, acetonide derivatives, diphenylmethylene ketals, cyclic borate esters, cyclic carbonate esters, cyclic carbamates and the like.

The term "cycloalkyl" as used herein refers to a three- to twelve-carbon cyclic group, such as cyclohexyl, cyclopropyl, bicyclooctyl, and the like. They can be unsubstituted; they can be substituted with one or more non-hydrogen substituent on the ring, for example, with alkyl, cycloalkyl, aryl or arylalkyl groups, with hydroxy, amino, alkylamino, aminoalkyl, mercapto, alkylthio or with halogen; or they can be fused to heterocyclic, aryl or other cycloalkyl groups, provided that any such substituent not interfere with the efficacy of the compound.

The term "dopamine-related cardiovascular disorders" as used herein refers to conditions which can be reversed or improved by admistration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which, because the role of dopamine in the cardiovascular system is presently incompletely defined, are still under investigation.

The term "dopamine-related neurological disorders" as used herein refers to behavioral disorders, such as psychoses and addictive behavior disorders; affective disorders, such as major depression; and movement disorders such as Parkinson's Disease, Huntington's Disease and Gilles de la Tourette's syndrome; which have been linked, pharmacologically and/or clinically, to either insufficient or excessive functional dopaminergic activity in the CNS. Also included are miscellaneous indications for which dopaminergic agents have been found to be clinically useful. Examples of such indications are disorders characterized by vomiting, such as uremia, gastroenteritis, carcinomatosis, radiation sickness, and emesis caused by a variety of drugs; intractable hiccough and alcoholic hallucinosis.

The term "fused" is used herein to mean two cyclic groups having at least two atoms in common to both rings.

The term "haloalkyl" refers to a lower alkyl group, as defined below, bearing at least one halogen substituent, for example trifluoromethyl.

The term "halogen" refers to bromo (Br), chloro (Cl), fluoro (F) and iodo (I).

The term "heterocycle" refers to a three- to twelve-atom monocyclic or bicyclic group containing one or more heteroatoms selected from N, O and S.

The term "lower alkoxy" refers to a lower alkyl group, as defined below, which is bonded through an oxygen atom. Examples of lower alkoxy groups are methoxy, ethoxy, t-butoxy and the like.

The term "lower alkyl" refers to branched or straight chain alkyl groups comprising one to six carbon atoms, including, but not limited to, methyl, ethyl, propyl, isopropyl, n-butyl, t-butyl, neopentyl and the like.

The term "nitrogen-containing heterocycle" refers to a five- to seven-atom monocyclic or bicyclic group containing one or more heteroatoms selected from S, O and N, wherein at least one of the heteroatoms is nitrogen. Examples of nitrogen-containing heterocycles include pyrrolidine, piperidine and the like. These heterocycles may be unsubstituted or they may be substituted, for example with lower alkyl, provided that any such substituent not interfere with interfere with the efficacy of the compounds.

"Normal dopamine levels" are those levels of dopamine that are found in the brains of control subjects and are usually measured as levels of the dopamine metabolites homovanillic acid (3-methoxy-4-hydroxyphenylacetic acid) and 3,4-dihydroxyphenylacetic acid. Abnormal dopamine levels are those levels that are not within the range of dopamine levels found in the brains of control subjects.

The term "parenteral" as used herein includes intravenous, intramuscular, intraperitoneal, intrasternal, subcutaneous and intraarticular injection and infusion techniques.

By "pharmaceutically acceptable" it is meant those salts, amides and esters which are, within the scope of sound medical judgement, suitable for use in contact with the tissues of humans and lower animals without undue toxicity, irritation, allergic response and the like, and are commensurate with a reasonable benefit/risk ratio, effective for their intended use in the treatment of neurological, cardiovascular and addictive behavior disorders. The salts can be prepared in situ during the final isolation and purification of the compounds of Formula (I), or separately by reacting the free base or acid function with a suitable organic acid or base. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like. Examples of pharmaceutically acceptable, nontoxic amides of the compounds of formula I include amides derived from ammonia, primary C1 to C6 alkyl amines and secondary C1 to C6 dialkyl amines wherein the alkyl groups are straight or branched chain. In the case of secondary amines the amine may also be in the form of a 5- or 6-membered heterocycle containing one nitrogen atom. Amides derived from ammonia, C1 to C3 alkyl primary amides and C1 to C2 dialkyl secondary amides are preferred. Amides of the compounds of formula I may be prepared according to conventional methods. It is understood that amides of the compounds of the present invention include amino acid and polypeptide derivatives.

As used herein, the term "pharmaceutically acceptable carriers" means a non-toxic, inert solid, semi-solid or liquid filler, diluent, encapsulating material or formulation auxillary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. Examples of pharmaceutically acceptable antioxidants include water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

The term "phenol" as used herein refers to hydroxyl derivatives of a benzene ring.

The term "phenol-protecting group" is used herein to mean substituents on the phenolic oxygen which prevent undesired reactions and degradations during a synthesis. Commonly used phenol-protecting groups include ethers, for example alkyl, alkenyl and cycloalkyl ethers (such as methyl, isopropyl, t-butyl, cyclopropylmethyl, cyclohexyl, allyl ethers and the like); alkoxyalkyl ethers such as methoxymethyl or methoxyethoxymethyl ethers and the like; alkylthioalkyl ethers such as methylthiomethyl ethers; tetrahydropyranyl ethers; arylalkyl ethers (such as benzyl, o-nitrobenzyl, p-methoxybenzyl, 9-anthrylmethyl, 4-picolyl ethers and the like); trialkylsilyl ethers such as trimethylsilyl, triethylsilyl, t-butyldimethylsilyl, t-butyldiphenylsilyl ethers and the like; alkyl and aryl esters such as acetates, propionates, n-butyrates, isobutyrates, trimethylacetates, benzoates and the like; carbonates such as methyl, ethyl, 2,2,2-trichloroethyl, 2-trimethylsilylethyl, vinyl, benzyl and the like; carbamates such as methyl, isobutyl, phenyl, benzyl, dimethyl and the like.

The term "readily cleavable group" is used herein to mean substituents which are rapidly cleaved in vivo, for example by hydrolysis in blood, to yield the parent compounds of the Formula (I). Readily cleavable groups include those substituents commonly referred to as prodrug moieties.

The term "spirocycloalkyl" is used herein to mean two cycloalkyl groups bonded to each other in such a way that a single carbon atom is common to both rings.

By a "therapeutically effective amount" of the dopaminergic agent is meant a sufficient amount of the compound to treat neurological, cardiovascular or addictive behavior disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

The total daily dose of the compounds of this invention administered to a host in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

The compounds of the present invention may be administered alone or in combination or in concurrent therapy with other agents which affect the central or peripheral nervous system. The compounds of the present invention may also be co-administered with agents, for example enzyme inhibitors, which block their metabolic transformation outside the CNS.

This invention also provides pharmaceutical compositions in unit dosage forms, comprising a therapeutically effective amount of a compound (or compounds) of this invention in combination with a conventional pharmaceutical carrier.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents.

If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantages of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

The compounds of the present invention are synthesized by the reaction schemes I through IX presented below, in which R and $R_1$-$R_8$ correspond to the R groups identified by Formula (I).

SCHEME IA

The compounds of Formula IA-IC are synthesized by the method discussed herein and illustrated below. An o-anisaldehyde derivative of Formula 1 (wherein $R_9$ is a phenol protecting group) and a substituted acetic acid derivative, such as phenyl acetic acid, are condensed in the presence of a dehydrating agent, such as acetic anhydride, and a proton acceptor such as triethylamine (TEA) to give the compounds of the Formula 2. The carboxylic acid (or acid derivative such as the methyl or ethyl ester) and the double bond are reduced by a reducing agent such as lithium aluminum hydride (LAH) preferably in an ether solvent such as tetrahydrofuran (THF) to afford the compounds of the Formula 3. The leaving group ability of the hydroxyl group is enhanced by derivatizing it with, for example, methanesulfonyl chloride, in the presence of a proton acceptor such as TEA, and it is then converted to the cyano compounds of the Formula 4 by nucleophilic displacement with a salt of cyanic acid such as sodium cyanide in a polar solvent such as dimethyl sulfoxide (DMSO). The cyano group is hydrolyzed to the corresponding carboxylic acid group under basic conditions using, for example, aqueous sodium hydroxide. The naphthalenone derivatives (compounds of the Formula 5) are prepared by intramolecular acylation of the protected phenol ring by conversion of the carboxylic acid to the corresponding acid chloride, using, a chlorinating agent such as thionyl chloride, followed by cyclization of the acid chloride, preferably using a Lewis acid catalyst such as aluminum chloride. Compounds of the Formula 5 are converted to the corresponding cyanohydrins by treatment with a cyano derivative such as trimethylsilylcyanide and the cyanohydrins are reduced to the amino alcohols of Formula 6 by treatment with a reducing agent such as LAH or borane. The 1-hydroxy group is eliminated from (6) by heating it under acidic conditions, e.g. in isopropyl alcohol saturated with hydrochloric acid, to produce the dihydronaphthalene derivatives of Formula 7. Compounds of Formula IA are produced when compounds of Formula 7 are treated with a suitable reagent for the removal of the phenol protecting group, for example, boron tribromide or boron trichloride in an inert solvent such as dichloroethane or methylene chloride. Compounds of Formula 7 are also hydrogenated to the corresponding tetrahydronaphthalene derivatives in the presence of a catalyst such as palladium or platinum on carbon and then deprotected with e.g. boron tribromide or boron trichloride to produce compounds of Formula IB.

Compounds of Formula IB, wherein $R_1$ and/or $R_2$ are hydrogen, are treated with a reagent, such as di-t-butyldicarbonate, for protecting the amino function and these compounds are, in turn, selectively halogenated and then deprotected, for example by treatment with acid, to afford the compounds of Formula IC.

Compounds IA-IC are further derivatized on the phenol hydroxyl group with easily cleavable acyl groups such as acetoxy groups or trimethylacetyl groups by treatment with the appropriate acyl derivatives, e.g. trimethylacetyl chloride or acetic anhydride. In the preferred embodiments of compounds IA and IB, $R_3$ is phenyl or cyclohexyl and X is bromo or chloro.

SCHEME IB

The compounds of Formula IA and IB are alternately synthesized by the method discussed herein and illustrated below. O-Anisaldehyde with the phenol hydroxyl protected as described in Example 1A and the aldehyde group derivatized as its dithiane is treated with a base such as n-butyl lithium, to generate the anion of Formula 8, and the anion is condensed with an alphabeta unsaturated acid derivative such as ethyl cinnamate in the presence of dimethyl-2-imidazolidinone to produce compounds of Formula 9. The dithiane group is removed from (9) by treatment with hydrogen in the presence of a catalyst such as Raney nickel or tri-n-butyl tin hydride/2,2'-azobisisobutyronitrile (AIBN), and the resultant intermediate is converted to compounds of Formula 5 as described in Scheme IA for the conversion of compounds of Formula 4 to compounds of Formula 5. Compounds of Formula 5 are also converted to compounds of Formula 7 as described in Scheme IA and further, compounds of Formula 7 are converted to compounds of Formulas IA and IB as described in Scheme IA.

SCHEME II

The compounds of Formulas IIA and IIB are synthesized by the methods discussed herein and illustrated below. The naphthalenone 10 (wherein $R_{10}$ is a catechol protecting group) is treated with a suitable reagent to remove the protecting groups, for example boron tribromide, to afford compounds of Formula 11. Compounds of Formula 11 are treated with a suitable reagent for selectively protecting the 6-hydroxy group to afford compounds of Formula 15. Compounds of Formula 15 are converted to their corresponding cyanohydrin derivatives of Formula 16 by treatment with a cyano derivative such as trimethylsilylcyanide and the cyanohydrin is, in turn, reduced to the amino alcohol (compounds of Formula 17) by treatment with a reducing agent such as LAH, preferably in a ether solvent such as diethyl ether. Compounds of Formula 17 are treated with a suitable reagent to induce the elimination the elements of water, for example compounds of Formula 17 are heated under acidic conditions, e.g. in isopropyl alcohol saturated with hydrochloric acid, to produce the dihydronaphthalene derivatives of Formula IIB. Compounds of Formula IIB can also be hydrogenated to the corresponding tetrahydronaphthalene derivatives of Formulas IIC and IID in the presence of a catalyst such as palladium or platinum on carbon. Compounds of Formula IIA and IIB can also be further derivatized on the phenol hydroxyl group with easily cleavable acyl groups such as acetoxy groups or trimethylacetyl groups by treatment with the appropriate acyl derivatives, e.g. trimethylacetyl chloride or acetic anhydride.

Alternately, compounds of Formula 11 are treated with a suitable reagent to selectively protect the 5-hydroxy group to afford compounds of Formula 12. Compounds of Formula 12 are converted to compounds of Formula IIA by the procedures described above for the conversion of compounds of Formula 15 to IIB.

In the preferred embodiments of compounds of Formulas IIA-IID, $R_3$ is phenyl or cyclohexyl and X is bromo or chloro.

SCHEME III

The compounds of Formula III are synthesized by the method discussed herein and illustrated below. A compound of Formula 18 (wherein $R_9$ is a phenol protecting group) is treated with a base such as n-butyl lithium to produce an anion. The lithium anion, or an organometallic derivative of the anion, for example the corresponding magnesium or cuprate derivative, is reacted with an epoxide of Formula 19 to produce compounds of Formula 20.

Compounds of Formula 20 can be oxidized to ketones with an oxidizing agent such as pyridinium chlorochromate and the ketones can, in turn, be enantioselectively reduced with, for example, B-chlorodiisopinocampheylborane to give the optically active isomers of the compounds of Formula 20.

Compounds of Formula 20 are condensed with a suitable bromo aldehyde derivative of Formula 21, such as bromoacetaldehyde dimethyl acetal or 3-bromo-propionaldehyde dimethyl acetal, to form the substituted benzopyran derivatives of Formula 22. Compounds of Formula 22 are converted to compounds of Formula 23 by treatment with a nucleophilic azide such as lithium or sodium azide in a polar solvent such as DMF, followed by reduction of the intermediate azido compounds, for example, with LAH. Compounds of Formula 23 are treated with a suitable reagent to remove the phenol protecting group, for example hydrobromic acid, to afford compounds of Formula IIIA.

Alternately, compounds of Formula 22 can be treated with a suitable brominating agent to afford compounds of Formula 24 which are, in turn, converted to compounds of Formula IIIB by the procedures described above for the conversion of compounds of Formula 22 to the compounds of Formula IIIA.

Alternately, compounds of Formula 22 are converted to the compounds of Formula IIIC by reaction with an amine such as allyl amine, cyclopropylamine, benzylamine, phenylethylamine or pyrrolidine, followed by treatment with a suitable reagent for the removal of the phenol protecting group, for example boron tribromide.

Compounds of Formula 24 are alternately converted to the compounds of Formula IIID by reaction with an amine such as allyl amine, cyclopropylamine, benzylamine, phenylethylamine or pyrrolidine, followed by treatment with a suitable reagent for the removal of the phenol protecting group, for example boron tribromide.

SCHEME IVA

Compounds of Formulas IVA and IVB are synthesized by the methods described herein and illustrated below. Compounds of Formula 25 are treated with a base such as n-butyl lithium and the resultant anion (or an organometallic derivative of the anion, for example the corresponding magnesium or cuprate derivative) is reacted with a carbonyl compound of Formula 26, for example an aldehyde such as cyclohexane carboxaldehyde or benzaldehyde or a ketone such as cyclohexanone, to afford the compounds of Formula 27. Compounds of Formula 27 are reacted with an appropriate formamide derivative such a N-(2,2-dimethoxyethyl)-formamide or N-(3,3-dimethoxypropyl)formamide, to give the compounds of Formula 29. The compounds of Formula 29 are, in turn, converted to the compounds of Formula 30 by reduction of the formyl substituent with a reducing agent such as LAH, followed by treatment with hydrochloric acid, followed by treatment with a suitable reagent for the removal of the phenol protecting group, for example hydrogen bromide/acetic acid. The compounds of Formula 30 are converted to the N,N-dialkyl derivatives of Formula IVA by treatment with an aldehyde, such as formaldehyde, and a reducing agent such as sodium cyanoborohydride in a polar solvent, preferably methanol.

Alternately, the compounds of Formula 27 are condensed with a suitable bromoaldehyde derivative of Formula 21, such as bromoacetaldehyde dimethyl acetal or 3-bromopropionaldehyde dimethyl acetal, to form the substituted benzopyran derivatives of Formula 31, as described in Scheme III. The compounds of Formula 31 are, in turn, converted to the compounds of Formula IVB by reaction with an amine such as allyl amine, cyclopropylamine, benzylamine, phenylethylamine or pyrrolidine, followed by treatment with a suitable reagent for the removal of the phenol protecting group, for example boron tribromide.

SCHEME IVB

The compounds of Formula IVC and IVD are synthesized by the methods described herein and illustrated below. Compounds of Formula 32 are treated with a reducing agent, such as sodium borohydride to afford the corresponding hydroxymethyl compounds which are, in turn, treated with a brominating agent, such as phosphorous tribromide, to afford the compounds of Formula 33, compounds of formula 33 are reacted with dithiane compound of Formula 34 such as phenyl-1,3-dithiane, to give the compounds of Formula 35. The compounds of Formula 35 are treated sequentially with n-chlorosuccinimide and a silver or mercury salt, such as silver nitrate, and then reducing agent, such as sodium borohydride, to afford the compound of Formula 36. The compounds of Formula 36 are, in turn, reacted with a suitable bromoaldehyde derivative of Formula 21, such as bromoacetaldehyde dimethyl acetal or 3-bromopropionaldehyde dimethyl acetal, to form the substituted benzopyran derivatives of Formula 37. Compounds of Formula 37 are converted to compounds of Formula IVC by treatment with a nucleophilic azide such as lithium or sodium azide in a polar solvent such as DMF, followed by reduction of the intermediate azido compounds, for example, with LAH and removal of the phenol protecting group, for example by hydrogenolysis.

Alternately, the compounds of Formula 37 are treated with a nucleophilic amine, such as allyl amine, cyclopropylamine, benzylamine, phenylethylamine or pyrrolidine, followed by removal of the phenol protecting group, for example by hydrogenolysis to afford the compounds of Formula IVD.

SCHEME V

The compounds of Formulas VA and VB are synthesized by the methods described herein and illustrated below. Benzaldehyde derivatives of Formula 38, wherein $R_1$ and $R_2$ are hydrogen or lower alkyl, $R_{11}$ is a lower alkyl group such as methyl or ethyl, and $R_9$ is preferably an alkoxyalkyl group, are treated with a base such as n-butyl lithium and the resultant anions, or an organometallic derivative of the anion, for example the corresponding magnesium or cuprate derivative, are reacted with an epoxide of Formula 19 to afford the compounds of Formula 39. The compounds of Formula 39 are cyclized in acidic solution, for example treatment with aqueous hydrochloric acid at ambient temperature, to afford the compounds of Formula 40. Compounds of Formula 40, wherein $R_1$ and/or $R_2$ are hydrogen, are, in turn, reacted with a cyano derivative such as trimethylsilyl cyanide to afford the compounds of Formula 41. The compounds of Formula 41 are then treated with an appropriate halogenating agent to give selectively the 6-halo (42a/42d), the 8-halo (42b/42e) or the 6,8-dihalo derivatives (42c) of Formula 42 as described herein in Examples 89, 91 and 94 for selective bromination. The compounds of Formula 42 are, in turn, treated with a reducing agent such as diborane, followed by generation of the desired acid salt to afford the compounds of Formula VA (a-e).

Alternately, the compounds of Formula 40 are reacted with nitromethane in the presence of an appropriate base such as ammonium acetate, sodium hydroxide or sodium bicarbonate, to afford the compounds of Formula 43. The compounds of Formula 43 are converted to the compounds of Formula VB by treatment with a suitable reagent for the removal of the phenol protecting group, for example anhydrous hydrochloric acid in methanol, followed by reduction of the nitro group, for example with catalytic hydrogenation, and generation of the desired acid salt.

SCHEME VIA

The compounds of Formula VIA-VIC are synthesized by the method discussed herein and illustrated below. Compounds of Formula 44 are treated with a cyano derivative such as trimethylsilylcyanide and a suitable reagent for removing the protecting groups, such as boron trifluoride etherate, to afford the compounds of Formula 45. The compounds of Formula 45 are, in turn, reduced to give compounds of Formula VIA with a reducing agent such as diborane.

Alternately, compounds of Formula 45 are treated with a suitable reagent for protecting the phenolic hydroxyl group to give the compounds of Formula 46. According to one method, the compounds of Formula 46 are treated with a reagent to enhance the leaving group ability of the hydroxy group, for example methanesulfonyl chloride, followed by treatment of the intermediate with a nucleophilic azide to afford the compounds of Formula 47. The compounds of Formula 47 are converted to VIB by treatment with a reducing agent, such as diborane or LAH, followed by treatment with a suitable reagent for removing the phenol protecting group, for example boron tribromide.

Alternately, the compounds of Formula 46 are treated with a reagent to enhance the leaving group ability of the hydroxy group, for example methanesulfonyl chloride, followed by treatment of the intermediate with a nucleophilic amine to afford the compounds of Formula 48. The compounds of Formula 48 are converted to VIC by treatment with a reducing agent, such as diborane or LAH, followed by treatment with a suitable reagent for removing the phenol protecting group, for example boron tribromide.

SCHEME VIB

The compounds of Formula VID, VIE and VIF are synthesized by the methods discussed herein and illustrated below. Compounds of Formulas 22, 24 and 31, wherein $R_3$ is benzyloxymethyl, are converted to compounds of the Formula 49 by removal of the benzyl protecting group, for example by hydrogenolysis, followed by displacement of bromine with a nucleophilic azide such as lithium or sodium azide in a polar solvent such as DMF. The compounds of Formula 49 are treated with a suitable reagent for activation of the hydroxy group, for example methanesulfonyl chloride, and the activated hydroxy group is displaced with a nucleophilic azide, such as lithium azide, to afford the diazido compounds of Formula 50. The compounds of Formula 50 are treated with a reducing agent such as LAH and a suitable reagent for the deprotection of the phenol hydroxyl group, for example boron tribromide or hydrochloric acid in alcohol to afford the compounds of Formula VID.

Compounds of Formula 49, are, alternately, converted to compounds of Formula VIE by treatment with a reducing agent such as LAH, followed by treatment with a suitable reagent for the removal of the phenol hydroxyl deprotecting group, for example born tribromide.

Compounds of Formula 49, are, alternately, converted to compounds of Formula VIF by activation of the 3-hydroxymethyl group by reaction with methanesulfonyl chloride followed by displacement with a amine, such as allyl amine, cyclopropylamine, benzylamine, pyrrolidine or piperidine or morpholine, followed by reduction of the azido group and treatment with a suitable reagent for removing the phenol protecting group.

SCHEME VII

The compounds of Formula VIIA and VIIB are synthesized by the methods discussed herein and illustrated below. Compounds of Formula 5 are converted to their corresponding cyanohydrin derivatives by treatment with a cyano derivative such as trimethylsilylcyanide, preferably in the presence of a catalyst such as aluminum trichloride. The cyano derivatives are dehydrated to the unsaturated nitriles by treatment with a dehydrating agent such as trifluoroacetic acid/p-toluenesulfonic acid and the unsaturated nitriles are in turn, reduced to the saturated nitriles of Formula 52 by treatment with a reducing agent such as sodium borohydride. The nitrile group is hydrolyzed to a carboxylic acid group (compounds of Formula 53) and the acid converted to the N-methoxy-N-methyl amide (compounds of Formula 54) by sequential treatment with a chlorinating agent, such as thionyl chloride, to generate the acid chloride and N-methoxymethylamine. Compounds of Formula 54 are converted to a mixture of the diastereomeric pyrrolidinyl derivatives 55 and 56 by treatment with 2,2,5,5,-tetramethyl-1-aza-2,5-disilacyclopentane-1-propyl magnesium bromide, followed by treatment with a reducing agent such as sodium cyanoborohydride, and the diastereomers are separated chromatographically. The separated isomers 55 and 56 are converted to compounds of Formula VIIA and VIIB, respectively, by treatment with an appropriate reagent to remove the phenol protecting group, preferably boron tribromide.

Alternately, compounds of Formula 52 are treated with appropriate halogenating agents to give selectively the 6-halo (52a), the 8-halo (52b) and the 6,8-dihalo derivatives (52c) of Formula 52 as described herein in Examples 89, 91 and 94 for selective bromination. Compounds 52 a–c are, in turn, converted to compounds of Formula VIIA a–c and VIIB a–c by the method described above for the conversion of compounds of Formula 52 to VIIA and VIIB.

SCHEME VIII

The compounds of Formula VIIA and VIIIB are synthesized by the methods discussed herein and illustrated below. Compounds of Formula 5, wherein $R_1$ is selected from hydrogen, lower alkyl, haloalkyl and lower alkoxy, are converted to compounds of Formula 57 by treatment with dimethyl succinate in the presence of a base such as potassium t-butoxide. Compounds of Formula 57 are reduced to the corresponding 1,2,3,4-tetrahydronaphthalene derivatives and the tricyclic ring is formed by treating the 1,2,3,4-tetrahydronaphthalene derivatives of the compounds of Formula 57 with a dehydrating agent such as polyphosphoric acid. Four isomeric products are obtained. Two of the isomers, compounds of Formulas 58 and 59, are carried on to compounds of Formulas VIIIA and VIIIB, respectively. Reduction of the 3-keto group of compounds of Formulas 58 and 59 with, for example hydrogen in the presence of a catalyst such as palladium on carbon support, is followed by hydrolysis of the ester in basic solution to give compounds of Formulas 60 and 61, respectively. Compounds of Formulas 60 and 61 are treated with diphenylphosphoryl azide and benzyl alcohol in the presence of a base such as TEA to afford the carbobenzyloxy protected amino derivatives, which are deprotected by hydrogenolysis using, for example, palladium on carbon support as a catalyst, and treated with a suitable reagent for the deprotection of the phenol, for example, boron tribromide, to afford the compounds of Formulas VIIIA and VIIIB. Compounds of Formulas VIIIA and VIIIB (wherein $R_1$ is H) are treated with a reagent, such as di-t-butyldicarbonate, for protecting the amino function and these compounds are, in turn, halogenated and then deprotected, for example, by treatment with acid, to afford the compounds of Formulas VIIIC and VIIID, respectively.

SCHEME IX

The compounds of Formula IX are synthesized by the method described herein and illustrated below. Compounds of Formula 5 are converted to the alpha-bromoketone by treatment with a brominating agent such as phenyltrimethylammonium tribromide. The bromide undergoes nucleophilic displacement for example with the anion of thiophenol to give the alphathiophenylketone of Formula 62. The ketone is reduced to the alcohol with a reducing agent such as sodium borohydride and the alcohol is eliminated with a dehydrating agent such as p-toluenesulfonic acid to give the thio-enolether. The sulfur is oxidized to the sulfoxide (compounds of Formula 63) with an oxidizing agent such as mCPBA. The amine component is made by a nucleophilic displacement on chloromethyltrimethylsilane by an amine of Formula 64, such as benzylamine. The imine is formed by treatment with an aldehyde such as formaldehyde and then an alcohol, such as methanol, is added to form the alkoxymethyl amine of Formula 66. This amine of Formula 66 is then reacted with the sulfoxide of Formula 63 in the presence of an acid, such as trifluoroacetic acid, to generate the azomethine ylid in situ which traps the activated double bond of the alpha, beta unsaturated sulfoxide to give a 1,3-dipolar addition adduct which, on heating, spontaneously undergoes elimination to give the cyclization-/elimination product of Formula 67. The amine can be deprotected by treatment with an acylating agent, such as 1-chloroethylchloroformate followed by acyl group removal with a nucleophile, such as methanol. The phenol can be deprotected by treatment with an appropriate reagent, preferably boron tribromide to give the compounds of Formula IX.
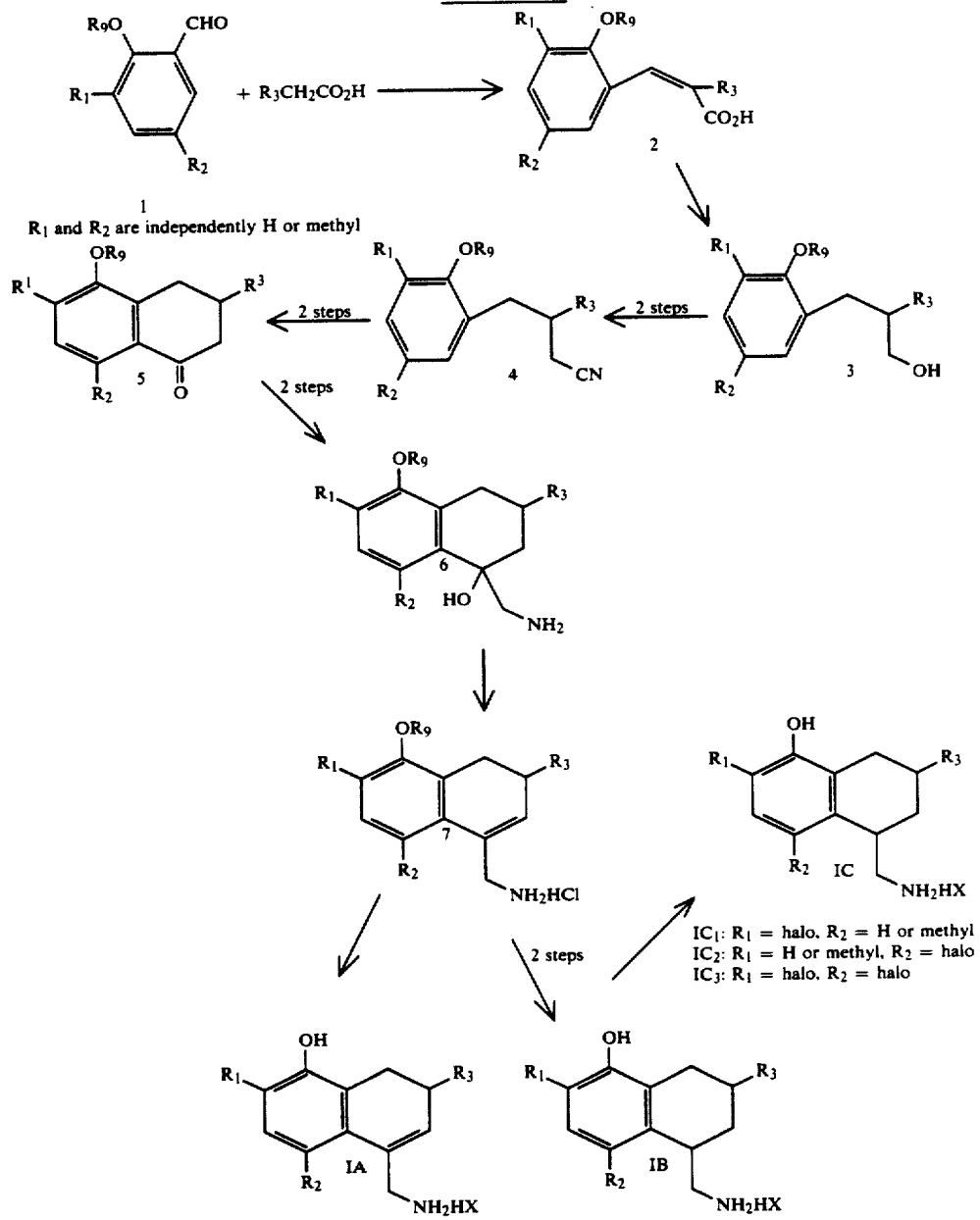
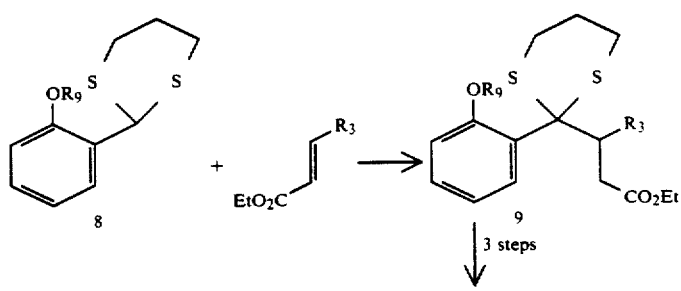

SCHEME IB
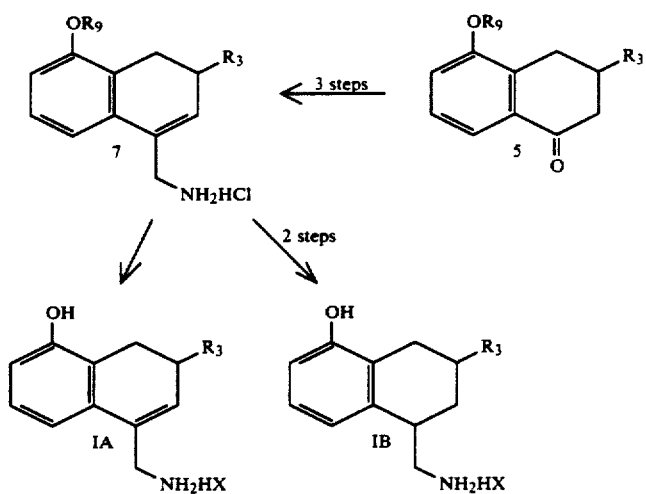
SCHEME II
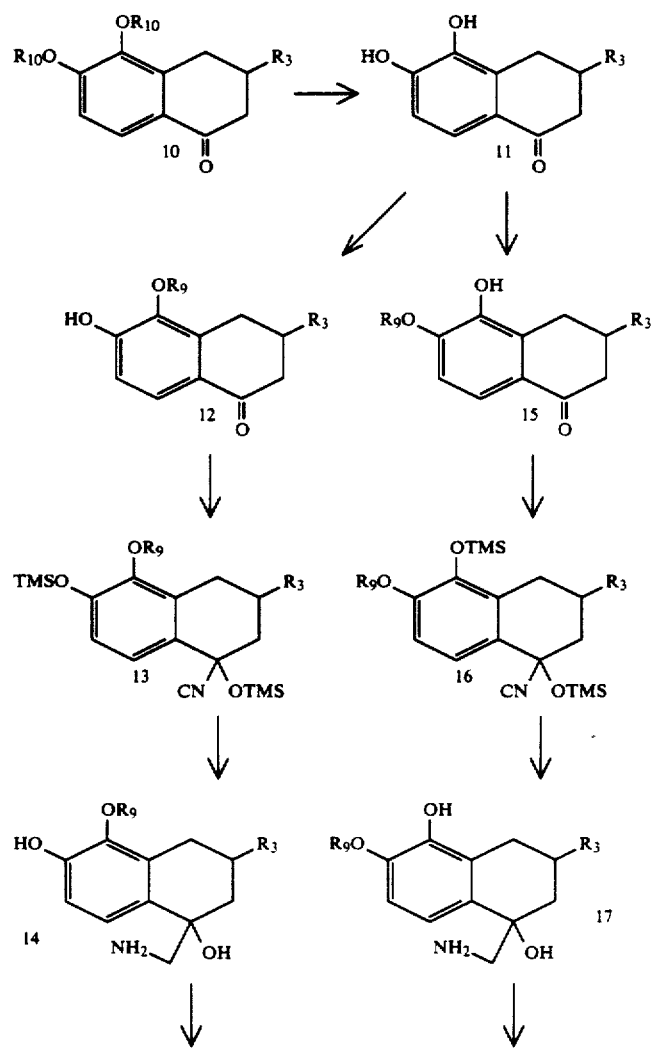

-continued
SCHEME II
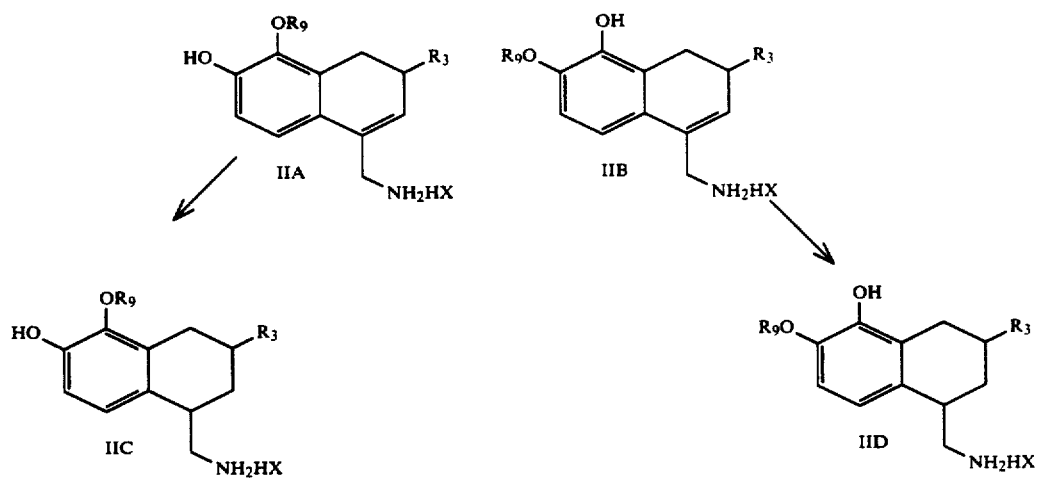
SCHEME III
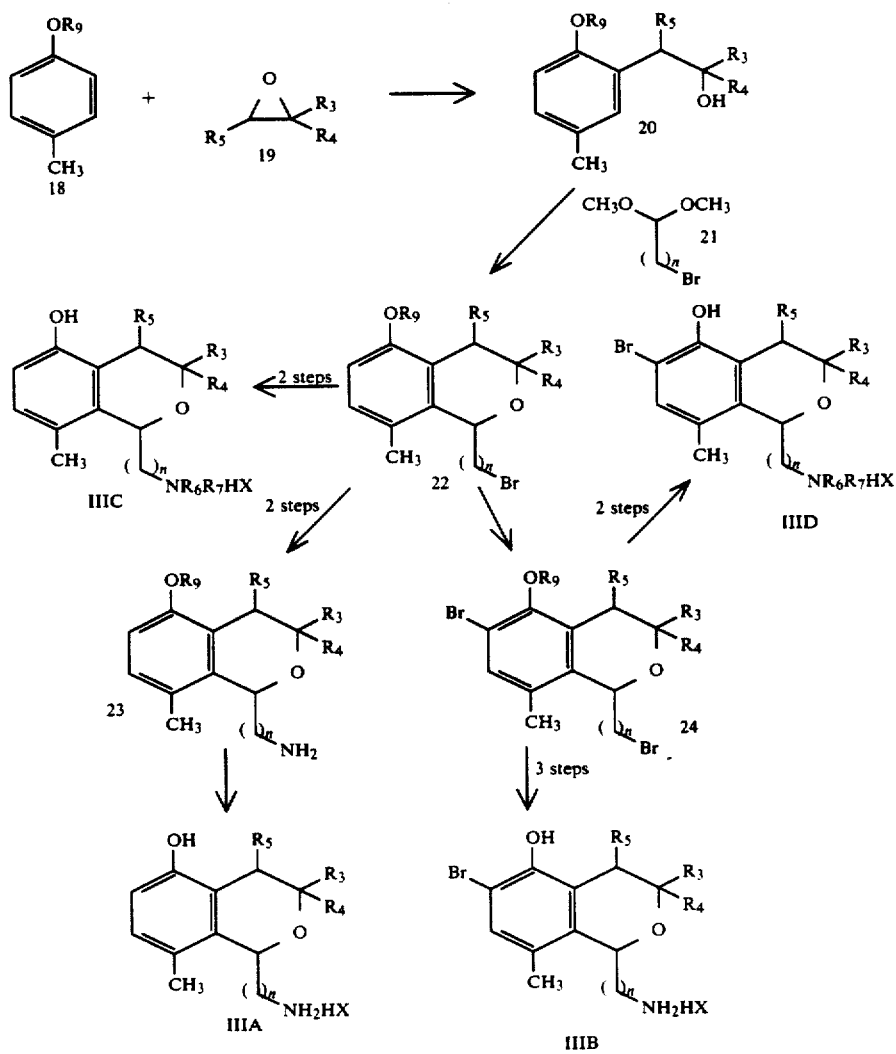

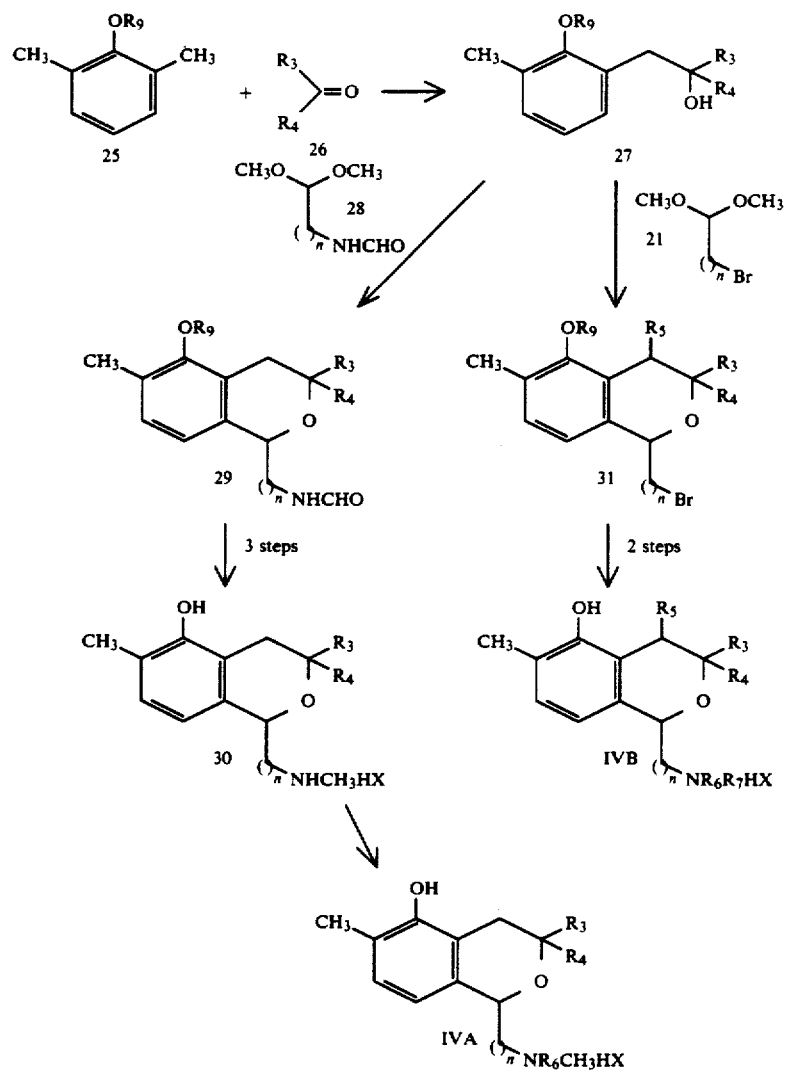
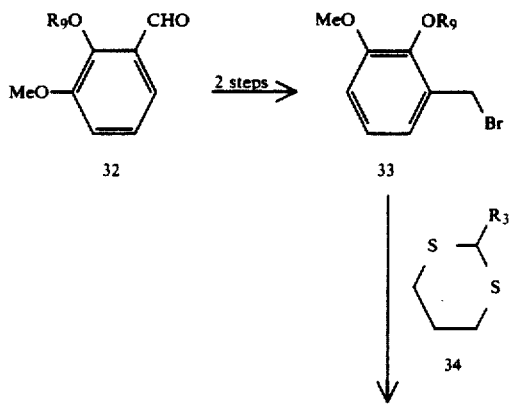
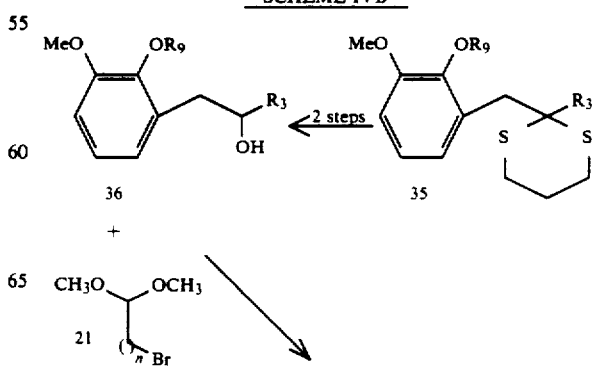

-continued
SCHEME IVB
SCHEME V
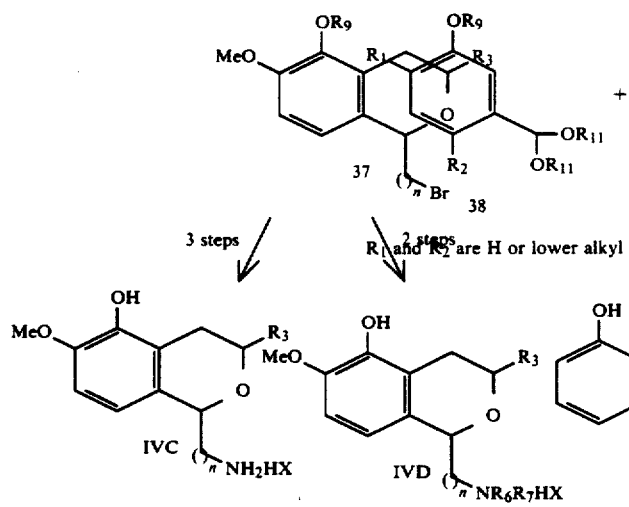
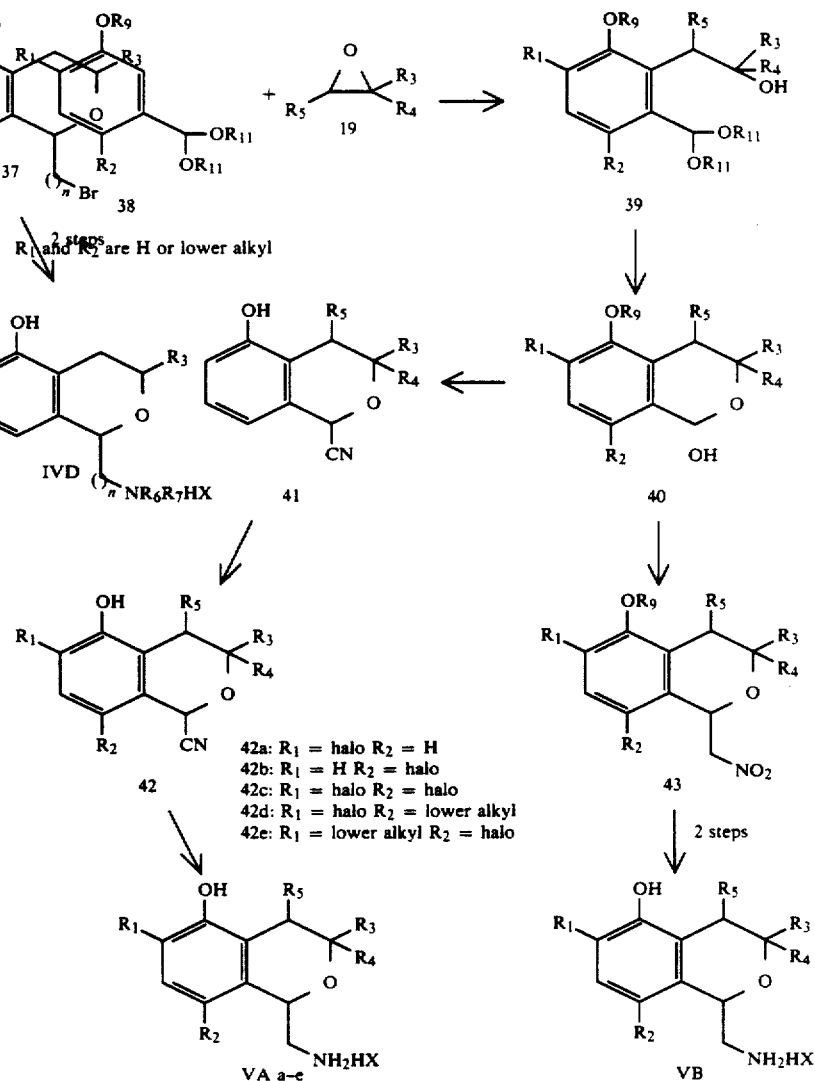
42a: $R_1$ = halo $R_2$ = H
42b: $R_1$ = H $R_2$ = halo
42c: $R_1$ = halo $R_2$ = halo
42d: $R_1$ = halo $R_2$ = lower alkyl
42e: $R_1$ = lower alkyl $R_2$ = halo SCHEME VIA
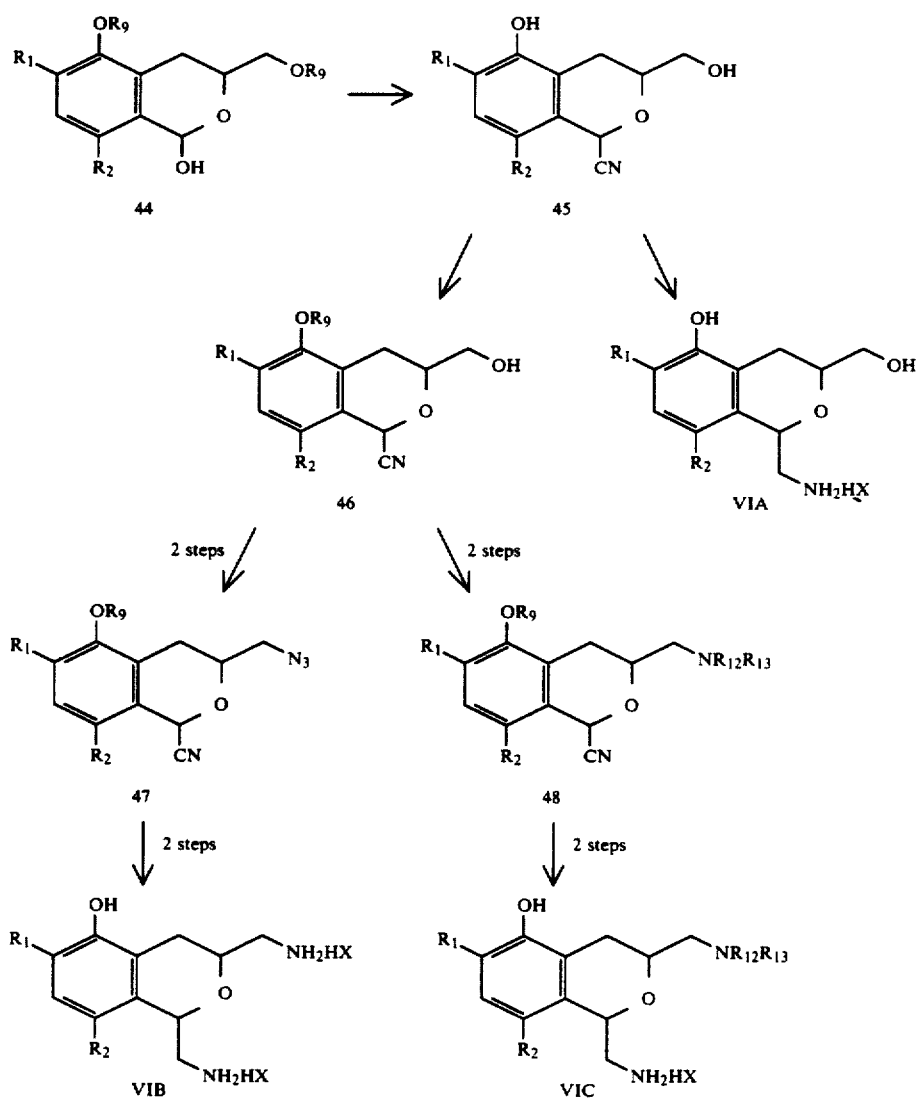
SCHEME VIB
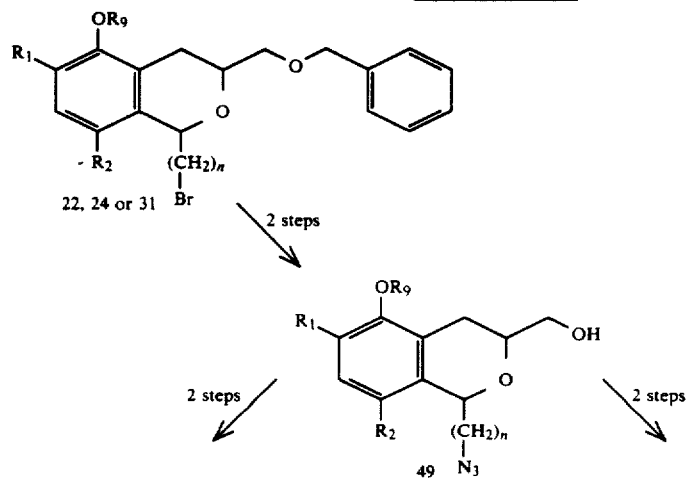

-continued
SCHEME VIB
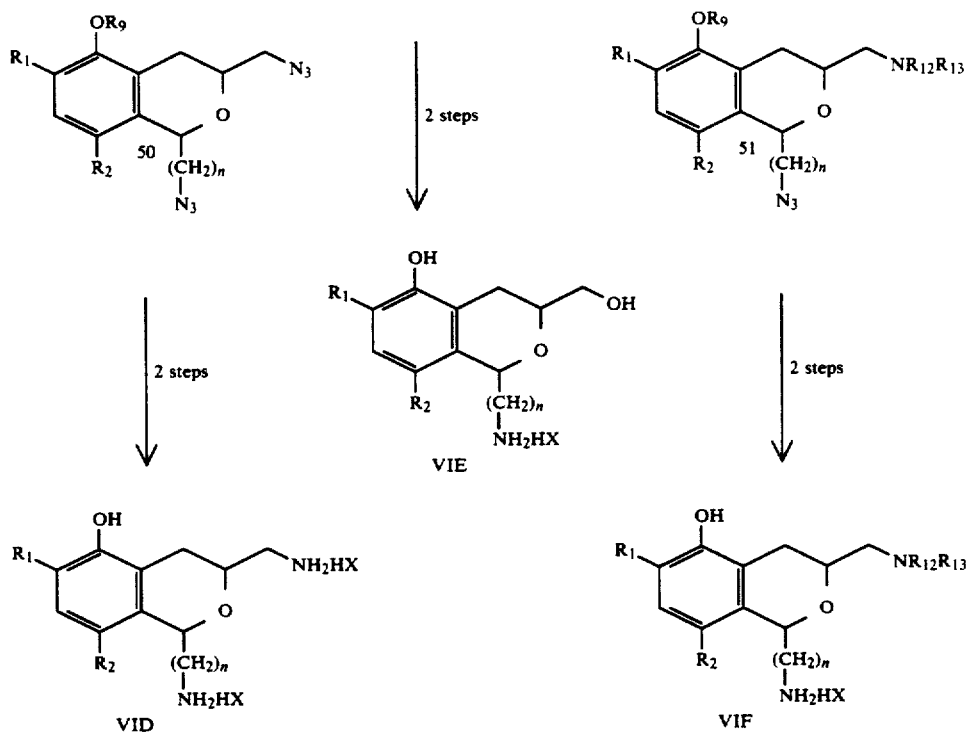
SCHEME VII
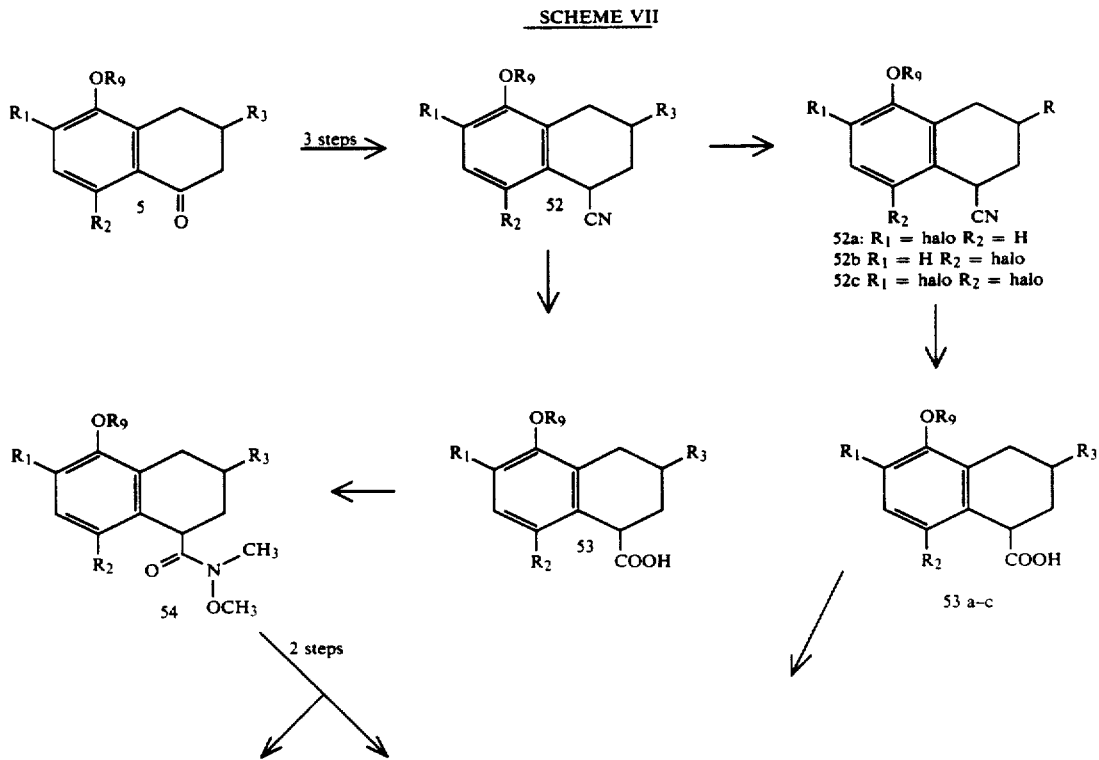

-continued
SCHEME VII
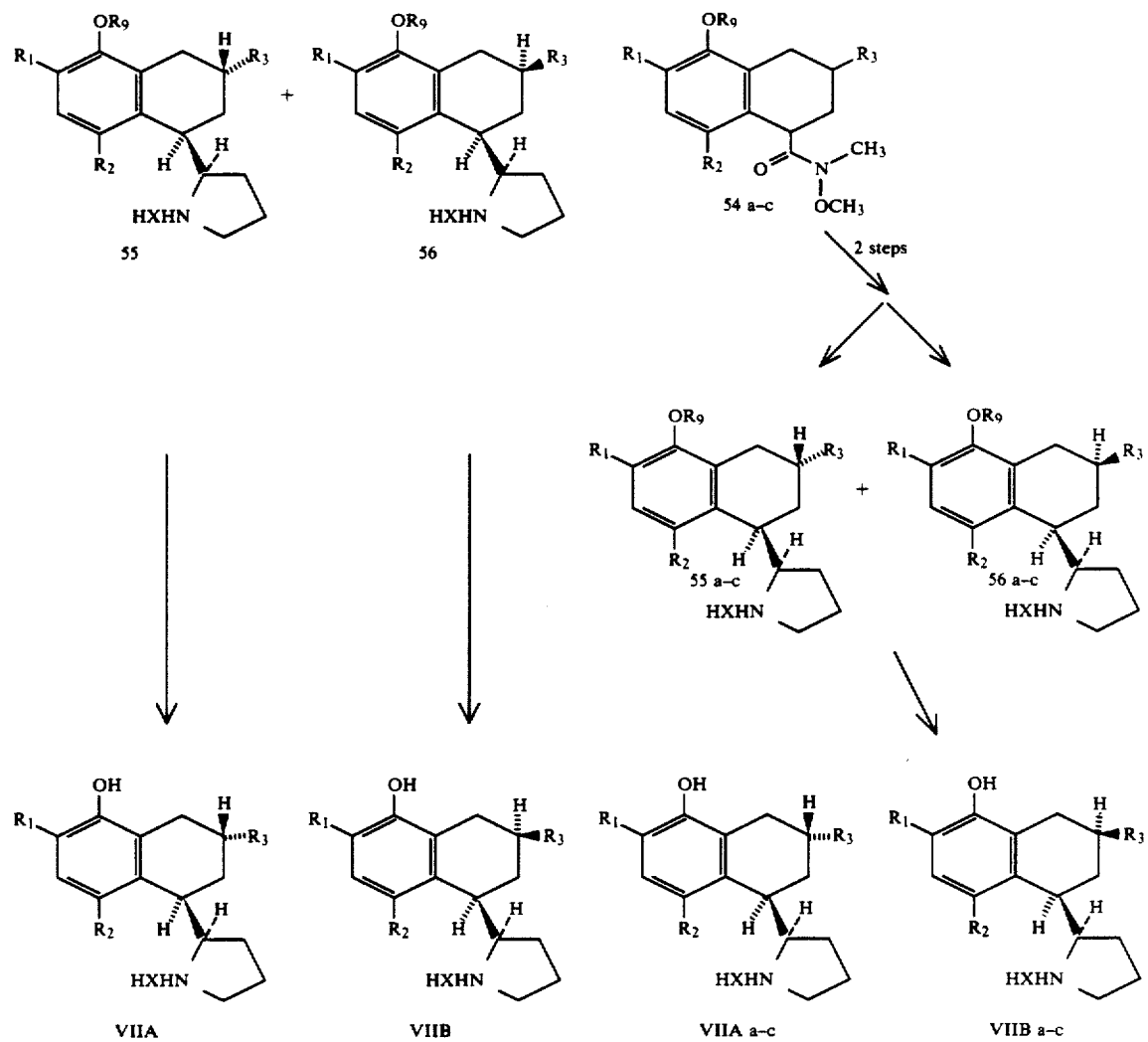
SCHEME VIII
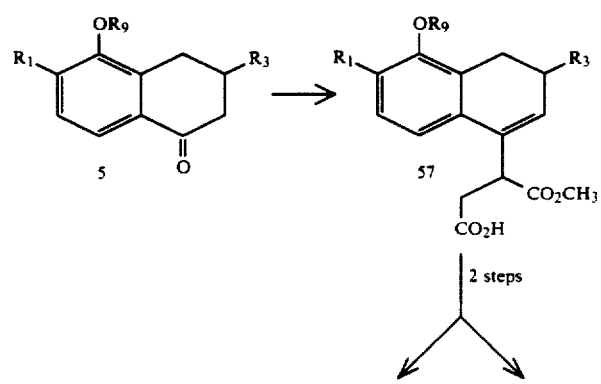

SCHEME VIII
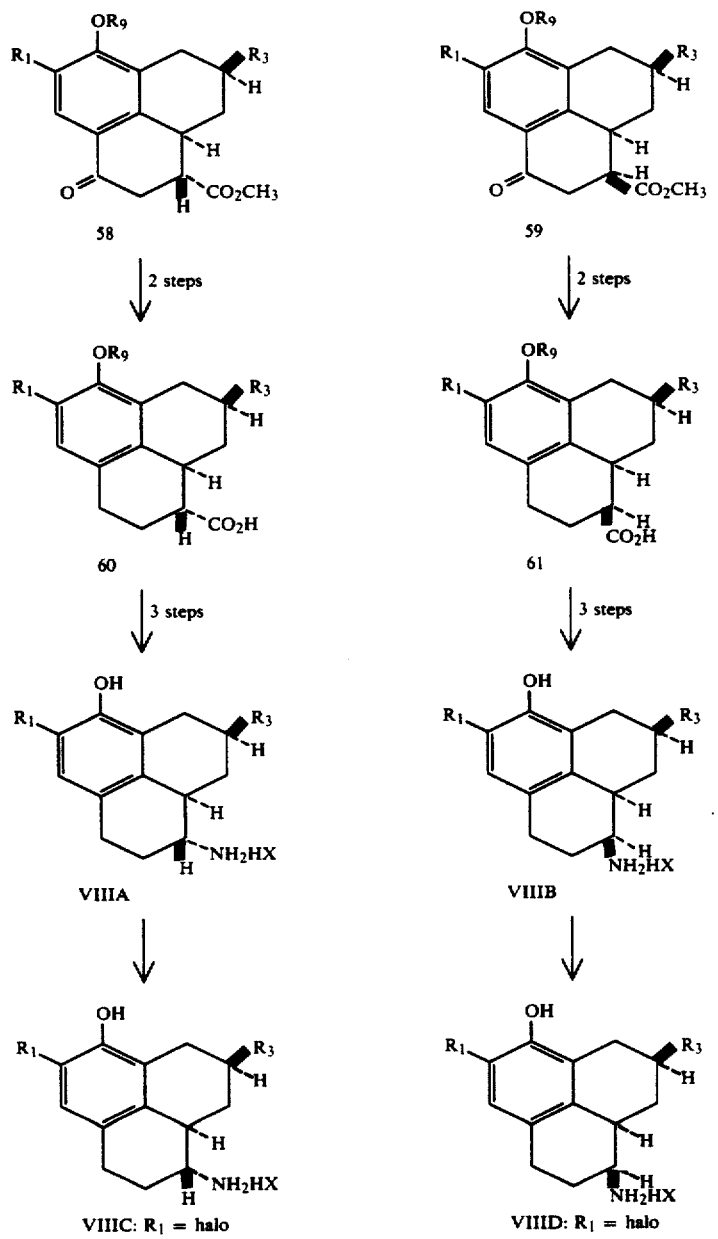
SCHEME IX
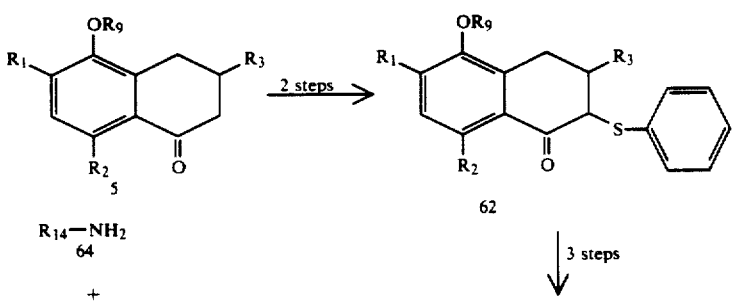

SCHEME IX

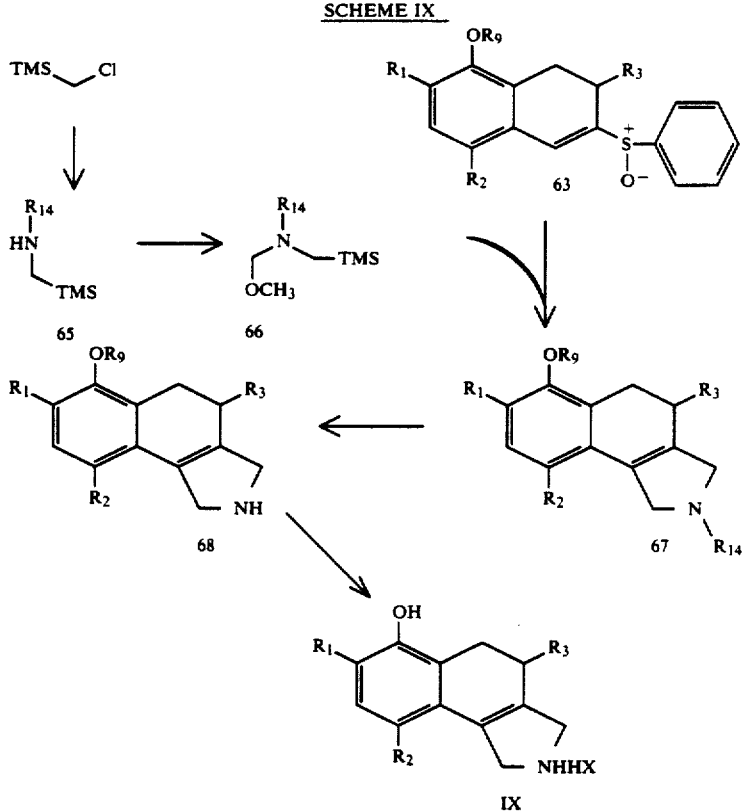

The foregoing may be better understood by reference to the following examples which are provided for the illustration and not the limitation of the invention.

EXAMPLE 1

5-Methoxy-3-phenyl-1,2,3,4-tetrahydro-1-naphthalenone

Method A

Step 1: (E.Z)-3-(2'-Methoxyphenyl)-2-phenylpropenoic acid

A solution of 36.8 mL (0.305 mol) of o-anisaldehyde (commericially available from Aldrich Chemical Company), 41.45 g (0.305 mol) of phenyl acetic acid (commercially available from Aldrich Chemical Company), 150 mL of acetic anhydride and 51 mL (0.366 mol) of triethylamine (TEA) was heated at reflux temperature for 24 h. The reaction mixture was allowed to cool to ambient temperature and 250 mL of water was added, followed by the addition of 500 mL of ethyl acetate and another 1 L of water. The layers were separated and the organic layer was extracted with saturated aqueous sodium bicarbonate solution. The organic layer was discarded. The aqueous layer was acidified with concentrated aqueous hydrochloric acid solution and extracted with 1 L of ethyl acetate. The ethyl acetate solution was dried over anhydrous magnesium sulfate and concentrated in vacuo to give 71 g (92% yield) of a 15/85 E/Z mixture of (E,Z)-3-(2'-methoxyphenyl)-2-phenylpropenoic acid as as an oil; DCl MS M/Z: 272 $(M+NH_4)^+$, 255 $(M+H)^+$.

Step 2: 3-(2'-Methoxyphenyl)-2-phenylpropanol

A solution of 24 g (362 mmol) of lithium aluminum hydride (LAH) in 250 mL of tetrahydrofuran (THF) was cooled to 0° C. (E,Z)-3-(2'-Methoxyphenyl)-2-phenylpropenoic acid (71 g, 280 mmol), from step 1, was dissolved in 350 mL of THF and the resultant solution was added to the LAH solution dropwise over a 30 min period. The reaction mixture was then heated at reflux temperature for 2 h. After cooling the reaction mixture to 0° C., the reaction was quenched by the careful sequential addition of 24 mL of water, 24 mL of 15% aqueous sodium hydroxide solution and 72 mL of water. The resultant precipitate was filtered and the filtrate concentrated in vacuo to give 72.6 g of 3-(2'-methoxyphenyl)-2-phenylpropanol as an oil; $^1$H NMR $(CDCl_3)\delta 1.8-1.9$ (m, 1H), 2.1–2.2 (m, 1H), 2.7–2.95 (m, 1H), 3.0–3.15 (m, 2H), 3.7–3.8 (m, 1H), 3.84 (s, 3H), 6.57 (t, 1H), 6.72 (dd, 1H), 6.83 (d, 1H), 7.15–7.4 (m, 6H).

Step 3: 3-(2'-Methoxyphenyl)-2-phenylpropane-1-methanesulfonate 3-(2'-Methoxyphenyl)-2-phenylpropanol (72.6 g, 300 mmol), from step 2, and 73.1 g (722 mmol) of TEA were dissolved in 500 mL of diethyl ether. Methanesulfonyl chloride (34.8 g, 304 mmol) was added slowly to this solution at 0° C. The reaction mixture was allowed to warm to ambient temperature. After stirring the reaction mixture for 2 h at ambient temperature, it was diluted with 300 mL of diethyl ether and washed with water, dried over anhydrous magnesium sulfate, filtered and concentrated to give 76.6 g (78% yield) of 3-(2'-methoxyphenyl)-2-phenylpropane-1-methanesulfonate as an oil; $^1$H NMR $(CDCl_3)\delta 2.7$ (s, 3H), 2.96 (dd, 1H), 3.35–3.45 (m, 1H), 3.83 (s, 3H), 4.35 (m, 2H), 6.57 (t, 1H), 6.70 (dd, 1H), 6.84 (d, 1H), 7.2–7.35 (m, 6H).

Step 4: 4-(2'-Methoxyphenyl)-3-phenylbutanenitrile 3-(2'-Methoxyphenyl)-2-phenylpropane-1-methanesulfonate (76.6 g, 239 mmol), from step 3, and 35.2 g (718 mmol) of sodium cyanide were dissolved in 200 mL of dimethyl sulfoxide (DMSO) and the resultant solution was heated to 80° C. After being stirred at 80° C. for 18 h, the reaction mixture was allowed to cool to ambient temperature, diluted with ethyl acetate and washed sequentially with water and saturated aqueous sodium chloride solution (brine). The solvents were removed in vacuo to give 60.1 g (100% yield) of the title compound as an oil; $^1$H NMR (CDCl$_3$)δ2.56 (d, 2H), 3.02 (d, 1H), 3.05 (d, 1H), 3.25–3.35 (m, 1H), 3.73 (s, 3H), 6.61 (t, 1H), 6.78 (dd, 1H), 6.85 (d, 1H), 7.2–7.4 (m, 6H).

Step 5: 4-(2'-Methoxyphenyl)-3-phenylbutyric acid 4-(2'-Methoxyphenyl)-3-phenylbutanenitrile (60.1 g, 239 mmol), from Step 4, was dissolved in 340 mL of ethylene glycol. Sodium hydroxide (67.5 g, 1.69 mol) and 135 mL of water were added and the reaction mixture was heated at reflux temperature for 24 h. The solvent was removed in vacuo and 1 L of water plus 1 L of methylene chloride were added to the residue. The layers were separated and the organic layer discarded. The aqueous layer was acidified with concentrated aqueous hydrochloric acid and extracted with 3 L of ethyl acetate. The ethyl acetate solution was dried over anhydrous sodium sulfate, filtered and concentrated in vacuo to give 49.8 g (77% yield) of the title compound as an oil; $^1$H NMR (CDCl$_3$)δ2.6–2.7 (m, 2H), 2.9 (d, 2H), 3.4–3.5 (m, 1H), 3.77 (s, 3H), 6.56 (t, 1H), 6.73 (dd, 1H), 6.80 (d, 1H), 7.0–7.4 (m, 6H).

Step 6: 5-Methoxy-3-phenyl-1,2,3,4-tetrahydro-1-naphthalenone 4-(2'-Methoxyphenyl)-3-phenylbutyric acid (29.1 g, 108 mmol), from Step 5, was dissolved in 50 mL of thionyl chloride and heated to 60° C. for 10 min. After stirring an additional 30 min at ambient temperature, the solvent was removed in vacuo. The crude product was dissolved in 60 mL of methylene chloride and the resultant solution was added dropwise to 15.8 g (118 mmol) of aluminum chloride in 240 mL of methylene chloride precooled to 0° C. After the addition, the reaction was allowed to proceed at 0° C. for 1 h, and then quenched by the addition of 500 g of ice. The methylene chloride layer was separated and washed with 3×200 mL of water, dried over anhydrous sodium sulfate, filtered and concentrated in vacuo to give 9.84 g (36% yield) of 5-methoxy-3-phenyl-1,2,3,4-tetrahydro-1-naphthalenone as a clear yellow oil; $^1$H NMR (CDCl$_3$)δ2.48 (dd, 1H), 2.65–2.8 (m, 2H), 3.20 (dd, 1H), 3.7–3.85 (m, 1H), 3.82 (s, 3H), 6.85–6.95 (m, 2H), 7.08 (dd, 1H), 7.2–7.3 (m, 1H), 7.35–7.4 (m, 2H), 7.57 (dt, 1H), 7.73 (d, 1H); DCl MS M/Z: 270 (M+NH$_4$)$^+$, 253 (M+H)$^+$.

Method B

Step 1: 2-(2'-Methoxyphenyl)-1,3-dithiane

A solution of 20.4 g (150 mmol) of o-anisaldehyde and 24 mL (239 mmol) of propane-1,3-dithiol in 300 mL of methylene chloride was cooled to 0° C. Boron trifluoride etherate (4.0 mL, 33 mmol) was added dropwise to the cooled solution and the reaction mixture was stirred at 0° C. for 0.5 h, then at ambient temperature for 18 h. The methylene chloride solution was washed with 2×100 mL of 10% aqueous sodium hydroxide solution, 100 mL of water and 100 mL of brine, dried over anhydrous sodium sulfate and concentrated in vacuo to give 35.4 g (95% yield) of 2-(2'-methoxyphenyl)-1,3-dithiane, m.p. 127°–128° C.; $^1$H NMR (CDCl$_3$) δ 1.8–2.0 (m, 1H), 2.1–2.25 (m, 1H), 2.87 (t, 1H), 2.92 (t, 1H), 3.05–3.2 (m, 2H), 3.85 (s, 3H), 5.69 (s, 1H), 6.87 (d, 1H), 6.97 (t, 1H), 7.25 (dt, 1 H), 7.59 (dd, 1H).

Step 2: Ethyl 4-(1'',3''-dithiane)-4-(2'-methoxyphenyl)-3-phenylbutyrate

A solution of 2-(2'-methoxyphenyl)-1,3-dithiane (10 g, 44 mmol), from Step 1, in 90 mL of dry THF was cooled to −78° C. in a dry ice/acetone bath. To this solution was added 18.6 mL of a 2.5 molar solution of n-butyl lithium in hexane. After the addition was complete the reaction mixture was stirred for 0.75 h at −78° C. 1,3-Dimethyl-2-imidazolidinone (13.6 mL, 124 mmol), commercially available from Aldrich Chemical Company, was added to the reaction mixture in one portion, followed by 7.4 g (42 mmol) of ethyl cinnamate (commercially available from Aldrich Chemical Company) added dropwise. The reaction mixture was stirred for 1 h at −78° C. and then the reaction was quenched with 25 mL of 10% aqueous acetic acid and allowed to warm to 0° C. The reaction mixture was diluted with 100 mL of diethyl ether and the layers separated. The organic layer was washed with 2×50 mL of saturated aqueous sodium bicarbonate solution, 50 mL of water and 50 mL of brine, dried over anhydrous magnesium sulfate and concentrated to give a crude oily product. The crude product was chromatographed on silica gel eluted with 10% ethyl acetate in hexane to give 14.3 g (85% yield) of ethyl 4-(1'',3''-dithiane)-4-(2'-methoxyphenyl)-3-phenylbutyrate as an oil; $^1$H NMR (CDCl$_3$) δ 1.0 (t, 3H), 1.7–1.9 (m, 2H), 2.4–2.85 (m, 4H), 3.05–3.25 (m, 2H), 3.8–3.95 (m, 2H), 3.97 (s, 3H), 4.55–4.6 (m, 1H), 6.75–6.85 (m, 1H), 6.95 (d, 1H), 7.05–7.25 (m, 6H), 7.6–7.7 (m, 1H).

Step 3: Ethyl 4-(2'-methoxyphenyl)-3-phenylbutyrate

Ethyl 4-(1'',3''-dithiane)-4-(2'-methoxyphenyl)-3-phenylbutyrate (10.1 g, 25 mmol) from Step 2, 225 g of Raney nickel and 400 mL of absolute ethanol were mixed together and heated at reflux temperature under 1 atmosphere of hydrogen for 3.25 h. The stirring was stopped and the mixture was allowed to cool slightly before the solvent was decanted from the catalyst. An additional 300 mL of absolute ethanol was added to the catalyst and the mixture was stirred and heated to reflux. The stirring was again stopped and the reaction mixture was allowed to cool slightly before the solvent was decanted from the catalyst. The combined supernatants were filtered through Celite filter aid and concentrated in vacuo to give 5.7 g (77% yield) of ethyl 4-(2'-methoxyphenyl)-3-phenylbutyrate as a clear oil; $^1$H NMR (CDCl$_3$) δ 1.05 (t, 3H), 2.5–2.7 (m, 2H), 3.0–3.25 (m, 2H), 3.82 (s, 3H), 3.8–4.2 (m, 3H), 6.61 (t, 1H), 6.75 (dd, 1H), 6.81 (d, 1H), 7.1–7.4 (m, 6H).

Step 4: 4-(2'-Methoxyphenyl)-3-phenylbutyric acid

Ethyl 4-(2'-methoxyphenyl)-3-phenylbutyrate (5.7 g, 19 mmol), from Step 3, was dissolved in 25 mL of methanol and 14 mL of 50% aqueous sodium hydroxide solution was added in one portion. The reaction mixture was stirred at ambient temperature for 18 h. The reaction mixture was concentrated and the residue was partitioned between 100 mL of diethyl ether and 100 mL of water. The layers were separated and the aqueous layer was adjusted to pH 6 with 6M aqueous hydrochloric acid solution and extracted with 3×100 mL of diethyl ether. The organic layers were combined, washed with brine, dried over anhydrous magnesium sulfate, filtered and concentrated in vacuo to give 5.1 g (99% yield) of the title compound as a colorless oil. The $^1$H NMR spectrum was identical to the spectrum reported for the product of Step 5 of Method A, Example 1.

Step 5: 5-Methoxy-3-phenyl-1,2,3,4-tetrahydro-1-naphthalenone 4-(2'-Methoxyphenyl)-3-phenylbutyric acid was converted to the title compound by the procedures described in Step 6 of Method A.

EXAMPLE 2

1-Aminomethyl-5-hydroxy-3-phenyl-3,4-dihydronaphthalene formic acid salt

Step 1: 1-Aminomethyl-1-hydroxy-5-methoxy-3-phenyl-1,2,3,4-tetrahydronaphthalene 5-Methoxy-3-phenyl-1,2,3,4-tetrahydro-1-naphthalenone (1.9 g, 7.5 mmol), the product of Example 1, 3 mL of acetonitrile, 1.9 g (19 mmol) of trimethylsilylcyanide, commercially available from Aldrich Chemical Company, and 100 mg of aluminum chloride were mixed together and heated at reflux temperature for 2 h. The reaction mixture was cooled and concentrated. The residue was dissolved in 6 mL of diethyl ether and the ether solution was added dropwise to a solution of 0.62 g (16 mmol) of lithium aluminum hydride in 14 mL of diethyl ether. After the reaction mixture was heated at reflux temperature for 2 h, 0.6 mL of water was added dropwise, followed by 0.6 mL of 15% aqueous sodium hydroxide solution, followed by 1.8 mL of water. The reaction mixture was stirred until a granular precipitate formed. The solid was filtered and washed with 3×20 mL of methylene chloride. The filtrate was concentrated to give 2.0 g (95% yield) of the title compound as an oil; $^1$H NMR (d6-DMSO) $\delta$ 1.90 (t, 1H), 2.25 (dt, 1H), 2.65-2.85 (m, 2H), 2.95-3.25 (m, 3H), 3.78 (s, 3H), 6.85-7.05 (m, 3H), 7.2-7.5 (m, 5H).

Step 2: 1-Aminomethyl-5-methoxy-3-phenyl-3,4-dihydronaphthalene hydrochloride

1-Aminomethyl-1-hydroxy-5-methoxy-3-phenyl-1,2,3,4-tetrahydronaphthalene (2.0 g, 7.2 mmol), from Step 1, was heated at reflux temperature for 2 h in 75 mL of isopropyl alcohol saturated with hydrogen chloride. The resultant solution was concentrated and the solid residue was triturated with hot toluene to give 0.72 g (33% yield) of 1-aminomethyl-5-methoxy-3-phenyl-3,4-dihydronaphthalene hydrochloride, m.p. 193°-196° C.; $^1$H NMR (d6-DMSO) $\delta$ 2.78 (dd, 1H), 3.14 (dd, 1H), 3.2-3.5 (m, 2H+H$_2$O), 3.84 (s, 3H), 3.93 (d, 1H), 6.2 (m, 1H), 6.54 (d, 1H), 6.60 (d, 1H), 6.75 (d, 1H), 7.2-7.5 (m, 5H).

Step 3: 1-Aminomethyl-5-hydroxy-3-phenyl-3,4-dihydronaphthalene formic acid salt 1-Aminomethyl-5-methoxy-3-phenyl-3,4-dihydronaphthalene hydrochloride (0.5 g, 1.7 mmol), from Step 2, was suspended in 16 mL of methylene chloride and boron tribromide (5.8 mL of a 1 M solution of BBr$_3$ in methylene chloride) was added dropwise while the reaction mixture was being cooled (to −78° C.) in a dry ice/acetone bath. The reaction mixture was warmed to 0° C. and stirred for 0.5 h, then again cooled to −78° C. in a dry ice/acetone bath. Methanol (2.5 mL) was added dropwise to the reaction mixture, which was then allowed to warm to ambient temperature and concentrated in vacuo. Methanol was added to the residue and the solution was reconcentrated. The residue was dissolved in a small amount of methanol and chromatographed on a silica gel column eluted with ethyl acetate:formic acid:water (18:1:1, v/v/v) to give the formic acid salt of 1-aminomethyl-5-hydroxy-3-phenyl-3,4-dihydronaphthalene, m.p. 102°-104° C.; $^1$H NMR(d6-DMSO) $\delta$2.68 (dd, 1H), 3.06 (dd, 1H), 3.6-3.8 (m, 1H), 3.77 (s, 2H), 6.1 (m, 1H), 6.77 (d, 1H), 6.83 (d, 1H), 7.04 (t, 1H), 7.15-7.35 (m, 5H), 8.36 (s, 1H).

EXAMPLE 3

5-Acetoxy-1-aminomethyl-3-phenyl-3,4-dihydronaphthalene hydrochloride

A suspension of 1-aminomethyl-5-hydroxy-3-phenyl-3,4-dihydronaphthalene formic acid salt, the product of Example 2, in acetic anhydride saturated with anhydrous hydrogen chloride is stirred at ambient temperature for 48 h. A solid is collected by filtration and washed with diethyl ether. Crystallization of the crude material is achieved by dissolving the powder in hot ethanol, adding water, filtering the solution hot and allowing it to cool. Filtration and drying of the solid collected affords 1-aminomethyl-5-acetoxy-3-phenyl-3,4dihydronaphthalene hydrochloride.

EXAMPLE 4

1-Aminomethyl-5-t-butylacetoxy-3-phenyl-3,4-dihydronaphthalene hydrochloride

Step 1: 1-Aminomethyl-N-t-butoxycarbonyl-5-hydroxy-3-phenyl-3,4-dihydronaphthalene Triethylamine is added to a solution of 1-aminomethyl-5-hydroxy-3-phenyl-3,4-dihydronaphthalene (the product of Example 2) in dimethylformamide (DMF). The solution is cooled to 0° C. and a solution of di-t-butyldicarbonate in DMF is added over a period of 1 h. After the addition is complete, water is added to the reaction mixture and it is extracted with ethyl acetate. The combined organic layers from the extraction are washed with 1 N hydrochloric acid solution and brine, dried over anhydrous magnesium sulfate, filtered and concentrated in vacuo. The residue is triturated with boiling hexanes to give the title compound.

Step 2: 1-Aminomethyl-5-t-butylacetoxy-N-t-butoxycarbonyl-3-phenyl-3,4-dihydronaphthalene 1-Aminomethyl-N-t-butoxycarbonyl-5-hydroxy-3-phenyl-3,4-dihydronaphthalene from Step 1 and triethylamine are combined and cooled to 0° C. A solution of trimethylacetyl chloride in dioxane is added dropwise to the cooled solution. The reaction mixture is allowed to warm to ambient temperature and stirred at ambient temperature for 2 h. Water is added to the reaction mixture and the pH is adjusted to approximately 4 with concentrated phosphoric acid. The reaction mixture is extracted with diethyl ether. The combined ether extracts are washed with aqueous saturated sodium bicarbonate solution, water and brine, dried over anhydrous magnesium sulfate, filtered and concentrated in vacuo to give the title compound.

Step 3: 1-Aminomethyl-5-t-butylacetoxy-3-phenyl-3,4-dihydronaphthalene hydrochloride 1-Aminomethyl-5-t-butylacetoxy-N-t-butoxycarbonyl-3-phenyl-3,4-dihydronaphthalene, from Step 2, is dissolved in dioxane and saturated with anhydrous hydrogen chloride. The reaction mixture is stirred for 2 h and concentrated in vacuo. The solid residue is dissolved in a minimum amount of methanol and the methanol solution is added dropwise to an excess amount of diethyl ether. The precipitate is filtered, washed with diethyl ether and dried to give the title compound.

EXAMPLE 5

[1R,3S]
1-Aminomethyl-5-hydroxy-3-phenyl-1,2,3,4-tetrahydronaphthalene formic acid salt Step 1: [1R,3S] 1-Aminomethyl-5-methoxy-3-phenyl-1,2,3,4-tetrahydronaphthalene hydrochloride To 0.22 g (0.73 mmol) of 1-aminomethyl-5-methoxy-3-phenyl-3,4-dihydronaphthalene hydrochloride, from Step 2, of Example 2, in 5 mL of absolute ethanol, was added 0.05 g of 10% palladium supported on carbon. The reaction mixture was sealed under a blanket of hydrogen and stirred overnight at ambient temperature. The reaction mixture was flushed with nitrogen before it was filtered through Celite filter aid and washed with 15 mL of absolute ethanol and 15 mL of methylene chloride. The filtrate was concentrated to give 0.16 g (79% yield) of [1R,3S] 1-aminomethyl-5-methoxy-3-phenyl-1,2,3,4-tetrahydronaphthalene hydrochloride, m. p. 235°–237° C.; $^1$H NMR (d6-DMSO) δ2.15–2.25 (m, 2H), 2.5–2.65 (m, 1H), 2.8–2.95 (m, 2H), 3.0–3.1 (m, 1H), 3.1–3.4 (m, 1H), 3.45–3.5 (m, 1H), 3.72 (s, 3H), 6.43 (d, 1H), 6.62 (d, 1H), 6.94 (t, 1H), 7.2–7.3 (m, 1H), 7.35–7.45 (m, 4H).

Step 2: [1R,3S] 1-Aminomethyl-5-hydroxy-3-phenyl-1,2,3,4-tetrahydronaphthalene formic acid salt

[1R,3S] 1-Aminomethyl-5-methoxy-3-phenyl-1,2,3,4-tetrahydronaphthalene hydrochloride (0.16 g, 0.53 mmol), from Step 1, was suspended in 5 mL of methylene chloride and the suspension was cooled to −78° C. in a dry ice/acetone bath. Boron tribromide (19 mL of a 1 M solution in methylene chloride, 19 mmol) was added and the reaction mixture was allowed to warm to ambient temperature, kept at ambient temperature for 1.5 h then cooled to −78° C. Methanol (3 mL) was added to the reaction mixture and it was again allowed to warm to ambient temperature then concentrated in vacuo. The residue was dissolved in methanol and reconcentrated. The residue was redissolved in methanol and the methanol solution was chromatographed on a silica gel column eluted with ethyl acetate:formic acid:water (18:1:1, v/v/v) to give 0.11 g (70% yield) of the title compound as a white powder, m.p. 110°–112° C.; $^1$H NMR (d6-DMSO) δ1.7 (q, 1H), 2.1–2.25 (m, 1H), 2.35–2.5 (m, 1H), 2.75–2.90 (m, 2H), 2.9–3.05 (m, 1H), 3.05–3.2 (m, 1H), 3.25–3.35 (m, 1H), 6.07 (d, 1H), 6.81 (d, 1H), 7.0 (t, 1H), 7.2–7.3 (m, 1H), 7.3–7.4 (m, 4H), 8.38 (s, 1H).

EXAMPLE 6

1-Aminomethyl-5-hydroxy-6-methoxy-3-phenyl-3,4-dihydronaphthalene hydrochloride

Step 1: 5,6-Dihydroxy-3-phenyl-1,2,3,4-tetrahydro-1-naphthalenone

To a solution of 6.5 g (23 mmol) of 5,6-dimethoxy-3-phenyl-1,2,3,4-tetrahydro-1-naphthalenone (prepared from 2,3-dimethoxybenzaldehyde by the procedures described in Example 1) in 80 mL of anhydrous methylene chloride at −78° C., under nitrogen atmosphere, was added dropwise 100 mL (100 mmol) of a 1 M solution of boron tribromide in methylene chloride. The reaction mixture was stirred at −78° C. for 0.5 h and then at ambient temperature for 1 h. TLC analysis of the reaction mixture on silica gel plates eluted with 20% ethyl acetate in hexane indicated that the reaction was complete. The reaction mixture was cooled to −78° C. and 500 mL of methanol was added dropwise. The mixture was allowed to warm to ambient temperature and then was stirred for 1 h at ambient temperature and concentrated under reduced pressure. The residue was dissolved in methanol and the methanol was evaporated in vacuo. The residue was then purified on a silica gel column eluted with ethyl acetate:hexane (1:5 v/v) to give 5.57 g (95% yield) of the title compound.

Step 2: 5-Hydroxy-6-methoxy-3-phenyl-1,2,3,4-tetrahydro-1-naphthalenone

A 60% dispersion of sodium hydride in mineral oil (0.39 g, 9.8 mmol) was washed with hexane and the hexane was decanted. DMSO (15 mL) was added to the sodium hydride and the resultant suspension was stirred vigorously. To the suspension was added a solution of 2.5 g (9.8 mmol) of 5,6-dihydroxy-3-phenyl-1,2,3,4-tetrahydro-1-naphthalenone, from Step 1, in 10 mL of DMSO. The mixture was stirred at ambient temperature for 80 min and 0.61 mL (9.8 mmol) of methyl iodide was added in one portion. The reaction mixture was stirred at ambient temperature overnight and then made acidic with 5% aqueous hydrochloric acid solution. The mixture was stirred for 30 min and then filtered. The filter cake was dissolved in 20% ethyl acetate in hexane and chromatographed on a silica gel column eluted with 20% ethyl acetate in hexane and 50% ethyl acetate in hexane to give a brown solid. The solid was crystallized from ethyl acetate to give 1.13 g (43% yield) of the title compound as white crystals.

Step 3: 1-Aminomethyl-1,5-dihydroxy-6-methoxy-3-phenyl-1,2,3,4-tetrahydronaphthalene To a suspension of 5-hydroxy-6-methoxy-3-phenyl-1,2,3,4-tetrahydro-1-naphthalenone (1.13 g, 4.2 mmol), from Step 2, in 8 mL of anhydrous acetonitrile, was added 2.4 mL (18 mmol) of trimethylsilylcyanide and a catalytic amount of zinc iodide. The reaction mixture was heated at reflux for 4 h and then cooled and concentrated. The residue was kept overnight at 0° C. under nitrogen atmosphere and then dissolved in 16 mL of anhydrous THF. The THF solution was added dropwise to a suspension of 0.77 g (20 mmol) of lithium aluminum hydride (LAH) in 8 mL of THF at 0° C. under a nitrogen atmosphere. The mixture was allowed to warm to ambient temperature and then was heated at reflux for 1 h, allowed to cool to ambient temperature and was stirred at ambient temperature for 2 h. The reaction was quenched by the sequential addition of 0.8 mL of water, 0.8 mL of 15% aqueous sodium hydroxide solution and 2.8 mL of water. Anhydrous magnesium sulfate was added to the mixture and the suspension was diluted with 50 mL of methylene chloride and filtered. The filter cake was washed with 200 mL of methylene chloride and 300 mL of ethyl acetate and discarded. The combined filtrates were evaporated to give 0.95 g (75.4% yield) of the title compound. This product was taken on to the next step without purification.

Step 4: 1-Aminomethyl-5-hydroxy-6-methoxy-3-phenyl-3,4-dihydronaphthalene hydrochloride A fairly rapid stream of hydrogen chloride was bubbled for 5 minutes through a well stirred suspension of 1-aminomethyl-1,5-dihydroxy-6-methoxy-3-phenyl-1,2,3,4-dihydroxy-6-methoxy-3-phenyl-1,2,3,4-tetrahydronaphthalene (0.4 g, 1.3 mmol), from Step 3, in 10 mL of isopropanol at 0° C. The mixture was warmed to ambient temperature and then heated at reflux for 4 h. Evaporation of the solvent under reduced pressure yielded the crude amine hydrochloride salt which was purified on a silica gel column eluted with 5% methanol in chloroform. The amine base was stirred at ambient temperature for 2 h in 10 mL of diethyl ether saturated with hydrogen chloride. The ether solution was concentrated and the residue was crystallized from acetone to give 0.05 g (12% yield) of the title compound, m.p. 217°-217.5° C. Analysis calculated for $C_{18}H_{20}ClNO_2$: C, 68.02; H, 6.34; N, 4.41. Found: C, 67.64; H, 6.32; N, 4.39.

EXAMPLES 7-31

Following the procedures described in Examples 1A, 2, 5 and 6, starting with o-anisaldehyde and the appropriate commercially available acetic acid derivative (as shown), examples 7-31 are prepared as disclosed in Table 1.

TABLE 1

Examples 7-31

Table 1a

| Example # | $R_3$ |
|---|---|
| 7 | cyclohexyl |
| 8 | ethyl |
| 9 | n-hexyl |
| 10 | 1-adamantyl |
| 11 | 4-hydroxyphenyl |
| 12 | 4-bromophenyl |

Table 1b

| Example # | $R_3$ | Acetic acid derivative |
|---|---|---|
| 13 | cyclohexyl | cyclohexyl-CH2-COOH |
| 14 | ethyl | ethyl-COOH |
| 15 | n-hexyl | n-hexyl-COOH |
| 16 | 1-adamantyl | 1-adamantylacetic acid |
| 17 | 4-hydroxyphenyl | MeO-C6H4-CH2-COOH |
| 18 | 4-bromophenyl | Br-C6H4-CH2-COOH |

Table 1c

TABLE 1-continued

Examples 7-31

| Example # | $R_3$ |
|---|---|
| 19 | cyclohexyl |
| 20 | ethyl |
| 21 | n-hexyl |
| 22 | 1-adamantyl |
| 23 | 4-hydroxyphenyl |
| 24 | 4-bromophenyl |

Table 1d

| Example # | $R_3$ | Acetic acid derivative |
|---|---|---|
| 25 | cyclohexyl | cyclohexyl-CH2-COOH |
| 26 | ethyl | ethyl-COOH |
| 27 | n-hexyl | n-hexyl-COOH |
| 28 | 1-adamantyl | 1-adamantylacetic acid |
| 29 | 4-hydroxyphenyl | MeO-C6H4-CH2-COOH |
| 30 | 4-bromophenyl | Br-C6H4-CH2-COOH |
| 31 | phenyl | C6H5-CH2-COOH |

EXAMPLE 32

General Procedures for the Preparation of Epoxides

Method A: 1-Cyclohexyl ethylene oxide

Sodium hydride (4.5 g, 187 mmol) and trimethylsulfoxonium iodide (41.25 g, 187.5 mmol) were combined in a 3-neck flask equipped with a mechanical stirrer and an addition funnel. Dimethyl sulfoxide (DMSO) was added slowly over a 30 min period, until 200 mL had been added. Gas was evolved throughout the addition. A solution of cyclohexane carboxaldehyde (21.8 mL, 180 mmol) in 50 mL of DMSO was added dropwise to the reaction mixture over a 15 min period. The reaction mixture was heated to 55° C. and stirred at 55° C. for 30 min. The reaction mixture was cooled to ambient temperature and poured into 500 mL of water. The aqueous solution was extracted with 3×100 mL of diethyl ether. The combined ether extracts were washed with water and brine, dried over anhydrous magnesium sulfate and concentrated in vacuo. The crude product was distilled (44° C., 0.1 mm) to give 14 g (62% yield) of 1-cyclohexyl ethylene oxide as a clear colorless liquid.

Method B: 1-Benzyl ethylene oxide

A solution of m-chloroperbenzoic acid (mCPBA; 17 g, 0.1 mol) in 120 mL of methylene chloride was added (at ambient temperature) dropwise to a solution of allyl benzene (10 g, 85 mmol) in 200 mL of methylene chloride. After the reaction mixture was stirred for 5 h with a mechanical stirrer, 5 additional grams of m-CPBA were added and the reaction mixture stirred for another 2 h. The reaction mixture was then diluted with 200 mL of ether, washed with 2×100 mL of aqueous sodium bisulfite solution, 100 mL of aqueous sodium bicarbonate solution and 100 mL of brine. The organic solution was dried over anhydrous magnesium sulfate, filtered and concentrated in vacuo. The residue was purified by bulb-to-bulb distillation (60° C., 0.1 mm) to give 8.5 g (77% yield) of 1-benzyl ethylene oxide as a clear colorless liquid.

Method C: 1,2-Epoxy-5-trimethylsilyl-4-pentyne

Step 1: 5-Trimethylsilyl-3-butyn-1-ol

A solution of 3-butyn-1-ol (commercially available from Aldrich Chemical Company) in THF at 0° C. is treated with a solution of n-butyl lithium (2 equivalents) in hexane and the resultant solution is swirled at 0° C. for 1 h. Trimethylsilyl chloride is then added and the resulting mixture is stirred for 1 h at 0° C. and then partitioned between water and diethyl ether. The ether layer is washed with water and brine, dried over anhydrous magnesium sulfate, filtered and concentrated to afford the title compound.

Step 2: 5-Trimethylsilyl-3-butyn-1-al

Chromium trioxide is added in portions to an ice-cold solution of pyridine (2 equivalents) in methylene chloride. After being stirred at ambient temperature for 20 min, the resultant brown suspension is treated with a solution of 5-trimethylsilyl-3-butyn-1-ol, from Step 1, in methylene chloride. The reaction mixture is stirred for 2 h and then filtered through Celite filter aid, washing the filter cake with methylene chloride. The filtrate is concentrated and purified by column chromatography on silica gel to give the title compound.

Step 3: 1,2-Epoxy-5-trimethylsilyl-4-pentyne

5-Trimethylsilyl-3-butyn-1-al, from Step 2, is converted to the title compound according to Method A of this Example.

EXAMPLE 33

1-Aminomethyl-3-cyclohexyl-3,4-dihydro-5-hydroxy-8-methyl-1H-2-benzopyran hydrochloride Step 1: 1-Cyclohexyl-2-(2'-methoxy-5'-methyl)phenyl-1-ethanol To a solution of 10.1 mL (80 mmol) of p-methylanisole in 90 mL of dry THF at 0° C., was added, dropwise, 28 mL of a 2.5M solution of n-butyl lithium in hexane. After being stirred for 1 h at 0° C. and 5 h at ambient temperature, the reaction mixture was transferred, via canula, to a suspension of cuprous bromide dimethyl sulfide complex (7.20 g, 35 mmol) in 20 mL of dry THF at −78° C. The resultant mixture was stirred at −60° C. for 0.5 h, recooled to −78° C. and treated with a solution of 6.50 g (51 mmol) of 1-cyclohexylethylene oxide (the product of Example 32, Method A) in 10 mL of dry THF. The reaction mixture was then allowed to warm to 25° C., stirred at ambient temperature for 12 h and poured into 100 mL of saturated aqueous ammonium chloride solution. The resultant cloudy mixture was extracted with 2×150 mL of diethyl ether. The combined ether extracts were washed with water and brine, dried over anhydrous sodium sulfate, filtered and concentrated in vacuo. The residue was chromatographed on silica gel eluted with hexane:diethyl ether (5:1 v/v) to give 6.98 g (52% yield) of the title compound.

Step 2: 1-Bromomethyl-3-cyclohexyl-3,4-dihydro-5-methoxy-8-methyl-1H-2-benzopyran Boron trifluoride etherate (4.36 mL, 35 mmol) was added dropwise to a solution of 4.40 g (17.7 mmol) of 1-cyclohexyl-2-(2'-methoxy-5'-methyl)phenyl-1-ethanol from Step 1 and 2.4 mL (20.4 mmol) of bromoacetaldehyde dimethyl acetal in 60 mL of methylene chloride at −50° C. The reaction mixture was allowed to warm to 0° C. over a period of 1 h and then stirred at 0° C. for 6 h. The resultant mixture was diluted with 200 mL of diethyl ether and the ether solution was washed with aqueous sodium carbonate solution and brine, dried over anhydrous sodium sulfate, filtered and concentrated in vacuo. The residue was crystallized from hexane to afford 2.90 g (46% yield) of the title compound.

Step 3: 1-Aminomethyl-3-cyclohexyl-3,4-dihydro-5-methoxy-8-methyl-1H-2-benzopyran hydrochloride A solution of 0.90 g (2.5 mmol) of 1-bromomethyl-3-cyclohexyl-3,4-dihydro-5-methoxy-8-methyl-1H-2-benzopyran, from Step 2, in 20 mL of N,N-dimethylformamide (DMF) was treated with 1.65 g (25 mmol) of sodium azide. The reaction mixture was heated at 80° C. for 3 h, cooled to ambient temperature and then poured into 100 mL of water. The resultant cloudy mixture was extracted with 2×150 mL of diethyl ether and the combined ether extracts were washed with water and brine, dried over anhydrous sodium sulfate, filtered and concentrated in vacuo. The residue was purified on a silica gel column eluted with 5% diethyl ether in hexane to give 0.70 g (86% yield) of the intermediate, 1-azidomethyl-3-cyclohexyl-5-methoxy-8-methyl-1H-2-benzopyran. The intermediate was dissolved in 20 mL of diethyl ether and the resultant ether solution was cooled to 0° C. Lithium aluminum hydride (2.2 mL of a 1.0M solution in diethyl ether) was added and the reaction mixture was stirred at 0° C. for 1 h. The reaction mixture was allowed to warm to ambient temperature, stirred at ambient temperature for 1 h and then the reaction was quenched by the sequential addition of 80 μL of water, 80 μL of 15% aqueous sodium hydroxide solution and 250 μL of water. The reaction mixture was filtered and the filter cake was washed with methylene chloride. The combined filtrates were concentrated and the residue was treated with 25 mL of diethyl ether saturated with hydrogen chloride. The precipitate was collected by vacuum filtration to give 652 mg (91% yield) of the title compound as a white solid.

Step 4: 1-Aminomethyl-3-cyclohexyl-3,4-dihydro-5-hydroxy-8-methyl-1H-2-benzopyran hydrochloride A suspension of 294 mg (0.9 mmol) of 1-aminomethyl-3-cyclohexyl-3,4-dihydro-5-methoxy-8-methyl-1H-2-benzopyran hydrochloride, from Step 3, in 8 mL of glacial acetic acid and 8 mL of 48% aqueous hydrobromic acid was stirred at reflux temperature for 2 h. The reaction mixture was concentrated in vacuo to remove most of the hydrobromic acid. The aqueous concentrate was adjusted to pH 8.0 with 50% aqueous sodium hydroxide solution and saturated aqueous sodium bicarbonate solution. The resultant aqueous solution was extracted with 2×100 mL of methylene chloride and the combined extracts were dried over anhydrous sodium sulfate, filtered and concentrated in vacuo. The residue was purified on silica gel eluted with 5% methanol in methylene chloride to give the free amine. The amine was treated with diethyl ether saturated with anhydrous hydrogen chloride and the resultant precipitate was crystallized from methanol/ether to afford 152 mg (55% yield) of the title compound, m.p.>280° C.(dec); MS DCI-NH$_3$ M/Z: 276 (M+H)$^+$. Analysis calculated for C$_{17}$H$_{26}$ClNO$_2$+0.2H$_2$O: C, 64.73; H, 8.42; N, 4.47. Found: C, 64.78; H, 8.33; N, 4.26.

EXAMPLE 34

1-Aminomethyl-6-bromo-3-cyclohexyl-3,4-dihydro-5-hydroxy-8-methyl-1H-2-benzopyran hydrochloride Step 1: 6-Bromo-1-bromomethyl-3-cyclohexyl-3,4-dihydro-5-methoxy-8-methyl-1H-2-benzopyran A solution of 2.04 g (5.8 mmol) of 1-bromomethyl-3-cyclohexyl-3,4-dihydro-5-methoxy-8-methyl-1H-2-benxopyran (the product of Step 2 of Example 33) in 20 mL of dry methylene chloride was cooled to 0° C. and treated with 0.38 mL (7.4 mmol) of bromine. The resultant solution was stirred for 25 minutes at 0° C. and then poured into 30 mL of a saturated aqueous solution of sodium bisulfite. The cloudy mixture was extracted with 200 mL of diethyl ether and the organic extract was washed with saturated aqueous sodium bicarbonate solution, water and brine, dried over anhydrous sodium sulfate, filtered and concentrated in vacuo. The residue was crystallized from hexane/ether to afford 1.36 g (55% yield) of the title compound.

Step 2: 1-Aminomethyl-6-bromo-3-cyclohexyl-3,4-dihydro-5-hydroxy-8-methyl-1H-2-benzopyran hydrochloride Following the procedures described in Steps 3–4 of Example 33, 6-bromo-1-bromomethyl-3-cyclohexyl-3,4-dihydro-5-methoxy-8-methyl-1H-2-benzopyran, from Step 1, was converted to the title compound, m.p. 258°-259° C. (dec); MS DCI-NH$_3$ M/Z: 354 (M+H)$^+$. Analysis calculated for C$_{17}$H$_{25}$BrClNO$_2$: C, 52.26; H, 6.45; N, 3.58. Found: C, 51.98; H, 6.35; N, 3.50.

EXAMPLES 35–67

Following the syntheses outlined in Examples 33 and 34, using the appropriate epoxide and the appropriate aldehyde acetal, Examples 35–67 are prepared as disclosed in Table 2.

TABLE 2

Examples 35–67

| Example # | Compound | Epoxide* |
|---|---|---|
| 35 | [structure: OH, Me, benzopyran with phenyl and CH$_2$NH$_2$ substituents] | [styrene oxide] 1 |
| 36 | [structure: OH, Br, Me, benzopyran with phenyl and CH$_2$NH$_2$ substituents] | [styrene oxide] 1 |
| 37 | [structure: OH, Me, benzopyran with ethyl and CH$_2$NH$_2$ substituents] | [1,2-epoxybutane] 1 |
| 38 | [structure: OH, Br, Me, benzopyran with ethyl and CH$_2$NH$_2$ substituents] | [1,2-epoxybutane] 1 |

TABLE 2-continued

Examples 35–67

| Example # | Compound | Epoxide* |
|---|---|---|
| 39 | [structure: phenol with OH, Me, fused O-ring bearing CH2-cyclohexane spiro and CH2NH2] | [cyclohexane spiro epoxide] 2 |
| 40 | [structure: Br, OH, Me phenol with fused N-ring, cyclohexane spiro, CH2NH2] | [cyclohexane spiro epoxide] 2 |
| 41 | [structure: OH, Me phenol fused with cyclohexane-O ring, CH2NH2] | [cyclohexene oxide] 1 |
| 42 | [structure: Br, OH, Me phenol fused with cyclohexane-O ring, CH2NH2] | [cyclohexene oxide] 1 |
| 43 | [structure: OH, Me phenol with fused O-ring bearing adamantyl, CH2NH2] | [adamantyl epoxide] 2 |
| 44 | [structure: Br, OH, Me phenol with fused O-ring bearing adamantyl, CH2NH2] | [adamantyl epoxide] 2 |
| 45 | [structure: OH, Me phenol with fused O-ring bearing CH2-phenyl, CH2NH2] | [benzyl epoxide] 3 |

TABLE 2-continued

Examples 35-67

| Example # | Compound | Epoxide* |
|---|---|---|
| 46 | | 3 |
| 47 | | 3 |
| 48 | | 3 |
| 49 | | 1 |
| 50 | | 1 |
| 51 | | 2 |
| 52 | | 1 |

TABLE 2-continued
Examples 35-67

| Example # | Compound | Epoxide* |
|---|---|---|
| 53 | [structure: 3-bromo-phenol with Me, CH2-CH(decyl)-O-CH(CH2NH2) bicyclic] | [structure: 1,2-epoxydodecane] 1 |
| 54 | [structure: phenol with Me, CH2-CH(CH2C≡CH)-O-CH(CH2NH2) bicyclic] | (Me)₃Si—C≡C—CH2—[epoxide] 4 |
| 55 | [structure: 3-bromo-phenol with Me, CH2-CH(decyl)-O-CH(CH2NH2) bicyclic] | [structure: 1,2-epoxydodecane] 1 |
| 56 | [structure: phenol with Me, CH2-CH(CH2CH2CH2CH2CH=CH2)-O-CH(CH2NH2) bicyclic] | [structure: 1,2-epoxy-7-octene] 1 |
| 57 | [structure: phenol with Me, CH2-CH(hexyl)-O-CH(CH2NH2) bicyclic] | [structure: 1,2-epoxyoctane] 1 |
| 58 | [structure: 3-bromo-phenol with Me, CH2-CH(hexyl)-O-CH(CH2NH2) bicyclic] | [structure: 1,2-epoxyoctane] 1 |
| 59 | [structure: phenol with Me, CH2-CH(ethyl)-O-CH(CH2NH2) bicyclic] | [structure: 1,2-epoxybutane] 1 |
| 60 | [structure: 3-bromo-phenol with Me, CH2-CH(ethyl)-O-CH(CH2NH2) bicyclic] | [structure: 1,2-epoxybutane] 1 |

TABLE 2-continued

Examples 35-67

| Example # | Compound | Epoxide* |
|---|---|---|
| 61 | (structure: 3-Me, 6-OH phenol with CH2-CH(O-)-C6H4-Br and CH(CH2NH2)- ring) | 4-bromophenyl glycidyl (2) |
| 62 | (structure: Br, OH, Me substituted with 4-bromobenzyl) | 4-bromophenyl (2) |
| 63 | (structure: OH, Me phenol with phenoxypropyl ether) | phenyl glycidyl ether (1) |
| 64 | (structure: OH, Me phenol with 4-hydroxyphenoxy group) | 4-methoxyphenyl glycidyl ether (1) |
| 65 | (structure: OH, Me phenol with 4-tert-butylphenoxy group) | 4-tert-butylphenyl glycidyl ether (1) |
| 66 | (structure: OH, Me phenol with 2-biphenyloxy group) | 2-biphenyl glycidyl ether (1) |

TABLE 2-continued

Examples 35–67

| Example # | Compound | Epoxide* |
|---|---|---|
| 67 | 3-cyclohexyl-chroman with OH, Me, CH2-NH2 substituents and CH2-O-phenyl-Br side chain | 4-bromophenyl glycidyl ether |

*1 = commercially available  2 = synthesized by Method A (Example 32)
3 = synthesized by Method B (Example 32)

EXAMPLE 68

[1R.3S]

1-Aminomethyl-3-cyclohexyl-3,4-dihydro-5-hydroxy-6-methyl-1H-2-benzopyran hydrobromide Step 1: 1-Cyclohexyl-2-(2'-methoxy-3'-methyl)phenyl-1-ethanol n-Butyl lithium (14.0 mL of a 2.5 M solution in hexane, 35 mmol) was added dropwise to a solution of 4.95 mL (35 mmol) of 2,6-dimethyl anisole in 60 mL of dry THF at 0° C. and the resultant mixture was stirred at 0° C. for 1 h, and then at ambient temperature for 4 h. The reaction mixture was then cooled to 0° C., treated with 4.2 mL (35 mmol) of cyclohexane carboxaldehyde, allowed to warm to ambient temperature again and poured into saturated aqueous ammonium chloride solution. The cloudy mixture was extracted with diethyl ether and the ether solution was washed with water and brine and concentrated in vacuo. The residue was purified on silica gel eluted with hexane:diethyl ether (5:1 v/v) to give 4.2 g (48% yield) of the title compound.

Step 2: [1R.3S] 1- Aminomethyl-3-cyclohexyl-3,4-dihydro-5-methoxy-6-methyl-1H-2-benzopyran Following the procedures described in Steps 2–3 of Example 33, 1-cyclohexyl-2-(2'-methoxy-3'-methoxy 3'-methyl)phenyl-1-ethanol from Step 1 was converted to the title compound.

[1R.3S]

1-Aminomethyl-3-cyclohexyl-3,4-dihydro-5-hydroxy-6-methyl-1H-2-benzopyran hydrobromide A suspension of 1-aminomethyl-3-cyclohexyl-3,4-dihydro-5-methoxy-6-methyl-1H 2 benzopyran (467 mg, 1.43 mmol) in 10 mL of of glacial acetic acid and 10 mL of 48% hydrobromic acid was heated at reflux for 2 h. The reaction mixture was then concentrated in vacuo. The residue was crystallized from ethyl alcohol/methylene chloride to afford 478 mg of the title compound; m.p. 217°– 218° C.; MS DCl-NH$_3$ M/Z: 276 (M+H)$^+$. Analysis calculated for $C_{17}H_{26}BrNO_2$: C, 52.71; H, 6.82; N, 3.51. Found: C, 52.85; H, 6.97; N, 3.90.

EXAMPLES 69–86

Following the procedures described in Example 68, replacing cyclohexane carboxaldehyde with an appropriate carbonyl compound, Examples 69–86 are prepared as disclosed in Table 3.

TABLE 3

Examples 69–86

| Example # | Compound | Carbonyl Cpd |
|---|---|---|
| 69 | isochroman with Me, OH, NH2 substituents and ethyl side chain | propanal (CH3CH2CHO) |
| 70 | isochroman with Me, OH, NH2 substituents and ethyl side chain | propanal (CH3CH2CHO) |
| 71 | isochroman with Me, OH, NH2 substituents and tert-butyl side chain | pivaldehyde ((CH3)3C-CHO) |

4,994,486

TABLE 3-continued
Examples 69-86

| Example # | Compound | Carbonyl Cpd |
|---|---|---|
| 72 | (structure) | hexanal (CH₃(CH₂)₄CHO) |
| 73 | (structure) | 5-hexenal |
| 74 | (structure) | nonanal |
| 75 | (structure) | Me₃Si-C≡C-(CH₂)₃-CHO |
| 76 | (structure) | 1-adamantanecarboxaldehyde |
| 77 | (structure) | cyclohexanone |
| 78 | (structure) | cyclopentanone |
| 79 | (structure) | pivaldehyde (t-Bu-CHO) |

TABLE 3-continued

Examples 69-86

| Example # | Compound | Carbonyl Cpd |
|---|---|---|
| 80 | (structure) | cyclohexanecarboxaldehyde |
| 81 | (structure) | benzaldehyde (PhCHO) |
| 82 | (structure) | 4-bromobenzaldehyde |
| 83 | (structure) | 3-benzyloxybenzaldehyde |
| 84 | (structure) | phenylacetaldehyde |
| 85 | (structure) | 3-phenylpropanal |

TABLE 3-continued

Examples 69-86

| Example # | Compound | Carbonyl Cpd |
|---|---|---|
| 86 | Structure: benzopyran with OH, Me, and CH(NH₂) substituents, linked via CH-O-CH₂ to phenoxy group | OHC-CH₂-O-phenyl |

*H. C. Arndt and S. A. Carroll, Synthesis, 3,202-4 (1979)

EXAMPLE 87

3-Cyclohexyl-3,4-dihydro-1-(N,N-dimethyl)-aminomethyl-5-hydroxy-6-methyl-1H-2-benzopyran hydrochloride A solution of 200 mg (0.56 mmol) of 1-aminomethyl-3-cyclohexyl-3,4-dihydro-5-hydroxy-6-methyl-1H-2-benzopyran hydrobromide (the product of Step 2 of Example 68) in 3 mL of methanol was treated with 0.45 mL of a 37% aqueous formaldehyde solution (6.0 mmol), followed by 190 mg (3 mmol) of sodium cyanoborohydride and the resultant mixture was stirred at ambient temperature for 2 days. The reaction was quenched with 5 mL of 1 M aqueous hydrochloric acid and the mixture was poured into 150 mL of saturated aqueous sodium bicarbonate solution. The cloudy mixture was extracted twice with methylene chloride. The combined organic extracts were washed with brine and concentrated in vacuo. The residue was treated with diethyl ether saturated with anhydrous hydrogen chloride and the resultant solution was concentrated under reduced pressure. The residue was recrystallized from methanol/methylene chloride/diethyl ether to afford 108 mg (57% yield) of the title compound as a white solid, m.p. 217°-219° C.; MS DCI-NH₃ M/Z: 304 (M+H)⁺. Analysis calculated for $C_{19}H_{30}ClNO_2$: C, 66.78; H, 8.91; N, 4.10. Found: C, 66.44; H, 8.81; N, 4.15.

Following the procedures described in Example 87, replacing formaldehyde with an appropriate alkyl adehyde, all of the aminomethyl compounds of Formula (I) can be converted to their corresponding symmetrical N,N-dialkylamino derivatives.

EXAMPLE 88

3-Cyclohexyl-3,4-dihydro-5-hydroxy-1-(N-methyl)-aminomethyl-6-methyl-1H-2-benzopyran hydrobromide Step 1: 3-Cyclohexyl-3,4-dihydro-1-(N-formyl)-aminomethyl-5-methoxy-6-methyl-1H-2-benzopyran Boron trifluoride etherate (0.58 mL, 4.7 mmol) was added to a solution of 582 mg (2.3 mmol) of 1-cyclohexyl-2-(2'-methoxy-3'-methyl)-phenyl-1-ethanol (the product of Step 1 of Example 68) and 245 mg (2.9 mmol) of (N-formyl)aminoacetaldehyde dimethyl acetal in 5 mL of diethyl ether at 0° C. After being stirred for 2 days at ambient temperature, the reaction mixture was poured into 150 mL of saturated aqueous sodium bicarbonate solution. The resultant cloudy mixture was extracted with ethyl acetate. The ethyl acetate solution was washed with brine, dried over anhydrous sodium sulfate, filtered and concentrated in vacuo. The residue was purified on silica gel eluted with 40% ethyl acetate in hexane to afford 405 mg (55% yield) of the title compound.

Step 2: 3-Cyclohexyl-3,4-dihydro-5-hydroxy-1-(N-methyl)-aminomethyl-6-methyl-1H-2-benzopyran hydrobromide A solution of 0.40 g (1.27 mmol) of 3-cyclohexyl-3,4-dihydro-1-(N-formyl)-aminomethyl-5-methoxy-6-methyl-1H-2-benzopyran, from Step 1, in 4 mL of THF was treated with 2.5 mL of a 1.0 M solution of lithium aluminum hydride (2.5 mmol) in THF. The reaction mixture was heated at reflux for 12 h. The reaction was quenched by the sequential addition of 90 μL of water, 90 μL of 15% aqueous sodium hydroxide solution and 300 μL of water. The resultant precipitate was filtered and washed with methylene chloride and ethyl acetate. The filtrate was concentrated under reduced pressure and the residue was treated with diethyl ether saturated with anhydrous hydrogen chloride. The precipitate collected by vacuum filtration was 1-aminomethyl -3-cyclohexyl-3,4-dihydro-5-methoxy-6-methyl -1H-2-benzopyran hydrochloride. This compound was dissolved in 8 mL of glacial acetic acid and 8 mL of 48% aqueous hydrobromic acid solution, and the resultant solution was heated at reflux temperature for 2 h. The solution was concentrated in vacuo to give a brown oil, which was crystallized from ethanol/methylene chloride/diethyl ether to give 250 mg (65% yield) of the title compound as an off-white solid, m.p. 204°-205° C.; MS DCI-NH₃ M/Z: 290 (M+H)⁺. Analysis calculated for $C_{18}H_{28}BrNO_2$: C, 58.38; H, 7.62; N, 3.72. Found: C, 58.14; H, 7.65; N,3.72.

EXAMPLE 89

[1R,3S] 1 Aminomethyl-6-bromo-3,4-dihydro-5-hydroxy-3-phenyl-1H-2-benzopyran Step 1: 2-[2'-(2''-(1''.3''-dioxanyl)-6'-methoxymethoxyphenyl)]-1 -phenyl -1-ethanol n-Butyl lithium (48.8 mL of a 2.5 M solution in hexane, 122 mmol) was added dropwise to a solution of 27.5 g (122 mmol) of 2-(3'-methoxy-methoxy)phenyl-1,3-dioxane (prepared as described by Ronald and Winkle in *Tetrahedron*, 39, 2031 (1983)) in 250 mL of cyclohexane at 0° C. The resultant mixture was stirred at 0° C. for 1 h and then 13.67 mL (120 mmol) of styrene oxide was added and stirring was continued at ambient temperature for 3 days. The reaction mixture was then poured into 250 mL of water and the cloudy mixture was extracted with 500 mL of diethyl ether. The organic extract was washed with brine, dried over anhydrous sodium sulfate, filtered and concentrated in vacuo. The residue was purified on silica gel eluted with 40% diethyl ether in hexane to give 18.52 g (45% yield) of the title compound.

Step 2: 3,4-Dihydro-1-hydroxy-5-methoxymethoxy-3-phenyl-1H-2-benzopyran

A solution of 41.16 g (119 mmol) of 2-[2 '-(2"-(1",3"-dioxanyl)-6'-methoxymethoxyphenyl)]-1-phenyl-1-ethanol, the product of Step 1, in 850 mL of acetone was mixed with 100 mL of a 1 M aqueous hydrochloric acid solution and the resultant solution was stirred at ambient temperature for 1 h. The precipitate which formed was filtered and washed with water to afford the title compound. The filtrate was concentrated in vacuo and additional product was crystallized from the residue in hexane/ethyl acetate to give a total of 26.86 g (79% yield) of 3,4-dihydro-1-hydroxy-5-methoxymethoxy-3-phenyl-1H-2-benzopyran as a mixture of anomers.

Step 3: 1-Cyano-3,4-dihydro-5-hydroxy-3-phenyl-1H-2-benzopyran

A solution of 9.07 g (31.7 mmol) of 3,4-dihydro-1-hydroxy-5-methoxymethoxy-3-phenyl-1H-2-benzopyran, from Step 2 above, in 150 mL of methylene chloride at $-78°$ C. was treated, sequentially, with trimethylsilyl cyanide (8.5 mL, 64 mmol) and boron trifluoride etherate (6 mL, 49 mmol). After being stirred for 1.5 h at $-78°$ C., and for 4 h at ambient temperature, 100 mL of water was added and stirring was continued for 1 h. The reaction mixture was then extracted with $2 \times 300$ mL of ethyl acetate and the combined organic extract was washed with 200 mL of brine, dried over anhydrous sodium sulfate, filtered and concentrated in vacuo. The residue was purified on silica gel eluted with 10% ethyl acetate in hexane to give 7.33 g (92% yield) of the title compound as a 4:1 mixture of the trans and cis isomers.

Step 4: 6-Bromo-1-cyano-3,4-dihydro-5-hydroxy-3-phenyl-1H-2-benzopyran

Bromine (0.11 mL, 2.1 mmol) was added to a solution of 0.91 mL (8.7 mmol) of t-butylamine in 15 mL of toluene at 31 30° C. The resultant mixture was stirred at $-30°$ C. for 10 minutes, cooled to $-78°$ C. and then treated with a solution of 1.09 g (4.3 mmol) of 1-cyano-3,4-dihydro -5-hydroxy-3-phenyl-1H-2-benzopyran, from Step 3, in 15 mL of methylene chloride. The reaction mixture was stirred at $-78°$ C. for 3 h, allowed to slowly warm to ambient temperature over a 3 h period and then partitioned between ethyl acetate and water. The organic extract was washed with water and brine, dried over anhydrous sodium sulfate, filtered and concentrated in vacuo. The residue was purified on silica gel eluted with 1% ethyl acetate in hexane to give 0.32 g (24% yield) of [1 R, 3R]-6-bromo-1-cyano-3,4-dihydro-5-hydroxy-3-phenyl-1H-2-benzopyran and 0.26 g (20% yield) of [1R,3S] 6-bromo-1-cyano-3,4-dihydro-5-hydroxy-3-phenyl-1H-2-benzopyran.

Step 5: [1R.3S] 1-Aminomethyl-6-bromo-3,4-dihydro-5-hydroxy-3-phenyl-1H-2-benzopyran hydrochloride Borane-tetrahydrofuran complex (4 mL of a 1 M solution in THF, 4 mmol) was added to a solution of 0.29 g (0.9 mmol) of [1R,3S] 6-bromo-1-cyano-3,4-dihydro-5-hydroxy-3-phenyl-1H-2-benzopyran, from Step 4, in 10 ml of THF. The resultant mixture was stirred at ambient temperature for 3 days, treated with 15 mL of methanol and concentrated in vacuo. The residue was purified on silica gel eluted with ethyl acetate to give the amine product. The amine was treated with diethyl ether saturated with anhydrous hydrogen chloride. The precipitate which formed was collected by vacuum filtration to give 90 mg (27% yield) of the title compound, m.p. 207°-210° C.; MS DCl-NH$_3$ M/Z: 334 (M+H)$^+$. Analysis calculated for $C_{16}H_{17}BrClNO_2 + 0.7H_2O$: C, 50.14; H, 4.84; N, 3.65. Found: C, 50.12; H, 4.48; N, 3.52.

EXAMPLE 90

[1R,3R] 1 Aminomethyl-6-bromo-3,4-dihydro-5-hydroxy-3-phenyl-1H-2-benzopyran hydrochloride Following the procedures described in Step 5 of Example 89, [1R,3R]-6-bromo-1-cyano-3,4-dihydro-5-hydroxy-3-phenyl-1H-2-benzopyran, the product of Step 4 of Example 89, was converted to the title compound, m.p. 255°-257° C.; MS DCl-NH$_3$ M/Z: 334 (M+H)$^+$. Analysis calculated for $C_{16}H_{17}BrClNO_2 + 0.5H_2O$: C, 50.61; H, 4.78; N, 3.69. Found: C, 50.66; H, 4.74; N, 3.59.

EXAMPLE 91

[1R, 3R]1-Aminomethyl-8-bromo-3,4-dihydro-5-hydroxy-3-phenyl-1H-2-benzopyran hydrochloride Step 1: [1R,3R] 8-Bromo-1-cyano-3,4-dihydro-5-hydroxy-3-phenyl-1H-2-benzopyran A solution of 0.94 g (3.8 mmol) of 1-cyano-3,4-dihydro-5-hydroxy-3-phenyl-1H-2-benzopyran, the product of Step 3 of Example 89 in 10 mL of glacial acetic acid was treated with a solution of 1.2 g (3.8 mmol) of pyridine hydrobromide perbromide in 50 mL of glacial acetic acid and the resultant mixture was stirred for 48 h at ambient temperature. The precipitate was filtered to afford 351 mg (28% yield) of the title compound. An additional 229 mg (18% yield) of the desired product precipitated from the filtrate after concentration in vacuo, to give a total of 580 mg (46% yield) of [1R,3R] 8-bromo-1-cyano-3,4-dihydro-5-hydroxy-3-phenyl-1H-2-benzopyran.

Step 2: [1R,3R] 1-Aminomethyl-8-bromo-3,4-dihydro-5-hydroxy-3-phenyl-1H-2-benzopyran hydrochloride Following the procedures described in Step 5 of Example 89, [1R,3R] 8-bromo-1-cyano-3,4-dihydro-5-hydroxy-3-phenyl-1H-2-benzopyran, from Step 1, was converted to the title compound, m.p. 166°-168° C.; MS DCl-NH$_3$ M/Z: 334 (M+H)$^+$.

EXAMPLE 92

[1R,3S] 1-Aminomethyl-3,4-dihydro-5-hydroxy-3-phenyl-1H-2-benzopyran hydrochloride Step 1: [1R,3S] 3,4-Dihydro-5-methoxymethoxy-1-nitromethyl-3-phenyl-1H-2-benzopyran A solution of 1.81 g (6.3 mmol) of 3,4-dihydro-1-hydroxy-5-methoxymethoxy-3-phenyl-1H-2-benzopyran (the product of Step 2 of Example 89) and 488 mg (1.8 mmol) of ammonium acetate in 30 mL of nitromethane was heated at reflux for 3 days and then concentrated in vacuo, the concentrate was poured into 30 mL of a 1M aqueous hydrochloric acid solution and the cloudy mixture was extracted with $2 \times 150$ mL of ethyl acetate. The organic extract was washed with brine, dried over anhydrous sodium sulfate, filtered and concentrated in vacuo. The residue was purified on silica gel eluted with hexane/diethyl ether (8:1 v/v) to give 230 mg (11% yield) of the title compound.

Step 2: [1R,3S] 3,4-Dihydro-5-hydroxy-1-nitromethyl-3-phenyl-1H-2-benzopyran

A solution of 135 mg (0.4 mmol) of [1R,3S] 3,4-dihydro-5-methoxymethoxy-1-nitromethyl-3-phenyl-1H-2-benzopyran, from Step 1, in 5 mL of methanol was saturated with anhydrous hydrogen chloride. The resultant mixture was stirred at reflux temperature for 2 h and then concentrated in vacuo. The residue was purified on silica gel eluted with 5% methanol in methylene chloride to afford 75 mg (66% yield) of the title compound.

Step 3: [1R,3S] 1-Aminomethyl-3,4-dihydro-5-hydroxy-3-phenyl-1H-2-benzopyran hydrochloride A solution of 75 mg (0.26 mmol) of [1R,3S] 3,4-dihydro-5-hydroxy-1-nitromethyl-3-phenyl-1H-2-benzopyran, from Step 2, in 15 mL of ethyl acetate and 1.5 mL of isopropyl alcohol was treated with 75 mg of 10% palladium on carbon and the mixture was shaken under 4 atmospheres of hydrogen for 1 day. The reaction mixture was diluted with ethyl acetate and filtered through Celite filter aid. The filtrate was concentrated in vacuo and the residue was purified on silica gel eluted with 5% methanol in methylene chloride to give the amine product. The amine was treated with diethyl ether saturated with anhydrous hydrogen chloride to give 52 mg (69% yield) of the title compound, m.p. 160°–163° C.; MS DCI-NH$_3$ M/Z: 256 (M+H)$^+$. Analysis calculated for $C_{16}H_{18}ClNO_2 + 0.8H_2O$: C, 62.76; H, 6.45; N, 4.57. Found: C, 62.65; H, 6.34; N, 3.90.

EXAMPLE 93

[1R,3R]
6-Bromo-3,4-dihydro-5-hydroxy-1-(N-methyl)-aminomethyl-3-phenyl-1H-2-benzopyran hydrochloride A solution of 214 mg (0.6 mmol) of [1R,3R] 1-aminomethyl-6-bromo-3,4-dihydro-5-hydroxy-3-phenyl-1H-2-benzopyran hydrochloride (the product of Example 90) in 30 mL of ethyl formate was heated at reflux for 5 h, cooled to ambient temperature and concentrated in vacuo. The residue was dissolved in 6 mL of anhydrous THF. This solution was added slowly to a well-stirred solution of lithium aluminum hydride (4 mL of 1.0M solution in THF, 4 mmol). The resultant mixture was heated at reflux for 6 h, cooled to ambient temperature and the reaction was quenched by the sequential addition of 0.4 mL of water, 0.4 mL of 15% aqueous sodium hydroxide solution and 1.2 mL of water. Sodium sulfate was added and the mixture filtered. The filter cake was washed with methylene chloride and discarded. The filtrate was concentrated in vacuo and the residue purified on silica gel eluted with 5% methanol in chloroform to give 0.04 g (18% yield) of the amine product. The amine was treated with diethyl ether saturated with anhydrous hydrogen chloride to give the hydrochloride salt (the title compound), m.p. 240°–241° C.; MS DCI-NH$_3$ M/Z: 348 (M+H)$^+$. Analysis calculated for $C_{17}H_{19}BrClNO_2 + 0.3H_2O$: C, 52.34; H, 5.06; N, 3.59. Found: C, 52.24; H, 4.91; N, 3.59.

Following the procedures described in Example 93, replacing ethyl formate with an appropriate alkylcarboxylic acid derivative (preferably an ester, acid chloride or acid anhydride), all of the aminomethyl compounds of Formula (I) can be converted to their corresponding N-alkylamino derivatives. The N-alkylamino compounds can, in turn, be converted by the same procedures (using a different alkylcarboxylic acid derivative) to their corresponding unsymmetrical N,N-dialkyl derivatives.

EXAMPLE 94

[1R, 3S]
1-Aminomethyl-6,8-dibromo-3,4-dihydro-5-hydroxy-3-phenyl-1H-2-benzopyran hydrochloride Step 1:[1R, 3S]1-Cyano-6,8-dibromo-3,4-dihydro-5-hydroxy-3-phenyl-1H-2-benzopyran To a solution of t-butylamine (0.27 mL, 2.6 mmol) in 3.5 mL of toluene at −30° C. was added 66 μL (1.3 mmol) of bromine and the mixture was stirred for 15 minutes. The internal temperature was maintained between −20 and −30° C. The mixture was cooled to −78° C. and a solution of 0.336 g (1.3 mmol) of a 1:4 mixture of cis/trans 1-cyano-5-hydroxy-3-phenyl-3,4-dihydro-1H-2-benzopyran (the product of Step 3 of Example 89) in 4 mL of methylene chloride, was added dropwise. The internal temperature was maintained at −70° C. The reaction mixture was stirred at −78° C. for 2 h and then allowed to warm to ambient temperature over a 4 h period. The solid was filtered and washed with diethyl ether and methanol. The filtrate was evaporated and the residue was dissolved in methylene chloride. The methylene chloride solution was washed with 2×50 mL of aqueous 10% sodium hydroxide solution. The combined sodium hydroxide extracts were acidified with hydrochloric acid and the acidic solution was extracted with methylene chloride. The methylene chloride extract was dried over anhydrous sodium sulfate and concentrated in vacuo to afford 0.23 g (42% yield) of the title compound.

Step 2: [1R, 3S] 1-Aminomethyl-6,8-dibromo-3,4-dihydro-5-hydroxy-3-phenyl-1H-2-benzopyran hydrochloride By the procedures described in Step 5 of Example 89, [1R, 3S] 1-cyano-6,8-dibromo-3,4-dihydro-5-hydroxy-3-phenyl-1H-2-benzopyran hydrochloride, from Step 1, was converted to the title compound, m.p. 238°–240° C.; MS DCI-NH$_3$ M/Z:412 (M+H)$^+$.

EXAMPLES 95–130

Following the procedures described in Examples 89, 91 and 92, as indicated, Examples 95–130 are prepared from the appropriate aminomethyl-3,4-dihydro-1H-2-benzopyran compounds as disclosed in Table 4.

EXAMPLES 131–139

Following the procedures described in Example 89, Examples 131–139 are prepared from the appropriate N-protected aminomethyl dihydro- or tetrahydronaphthalene compounds as disclosed in Table 5.

TABLE 4

Examples 95–130

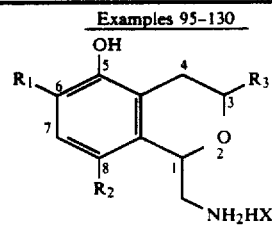

(I)

| Example # | R$_1$ | R$_2$ | R$_3$ | Method (Example #) |
|---|---|---|---|---|
| 95 | Br | H | ethyl | 89 |
| 96 | H | Br | ethyl | 91 |
| 97 | H | H | ethyl | 92 |
| 98 | Br | H | t-butyl | 89 |

TABLE 4-continued

Examples 95-130

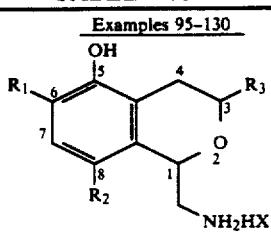

| Example # | R₁ | R₂ | R₃ | Method (Example #) |
|---|---|---|---|---|
| 99 | H | Br | t-butyl | 91 |
| 100 | H | H | t-butyl | 92 |
| 101 | Br | H | n-hexyl | 89 |
| 102 | H | Br | n-hexyl | 91 |
| 103 | H | H | n-hexyl | 92 |
| 104 | Br | H | isopropyl | 89 |
| 105 | H | Br | isopropyl | 91 |
| 106 | H | H | isopropyl | 92 |
| 107 | Br | H | n-octyl | 89 |
| 108 | H | Br | n-octyl | 91 |
| 109 | H | H | n-octyl | 92 |
| 110 | Br | H | n-decyl | 89 |
| 111 | H | Br | n-decyl | 91 |
| 112 | H | H | n-decyl | 92 |
| 113 | Br | H | cyclohexyl | 89 |
| 114 | H | Br | cyclohexyl | 91 |
| 115 | H | H | cyclohexyl | 92 |
| 116 | Br | H | 1-adamantyl | 89 |
| 117 | H | Br | 1-adamantyl | 91 |
| 118 | H | H | 1-adamantyl | 92 |
| 119 | Br | H | phenyl | 89 |
| 120 | H | Br | phenyl | 91 |
| 121 | H | H | phenyl | 92 |
| 122 | Br | H | 4-bromophenyl | 89 |
| 123 | H | Br | 4-bromophenyl | 91 |
| 124 | H | H | 4-bromophenyl | 92 |
| 125 | Br | H | benzyl | 89 |
| 126 | H | Br | benzyl | 91 |
| 127 | H | H | benzyl | 92 |
| 128 | Br | H | phenylethyl | 89 |
| 129 | H | Br | phenylethyl | 91 |
| 130 | H | H | phenylethyl | 92 |

TABLE 5

Examples 131-139

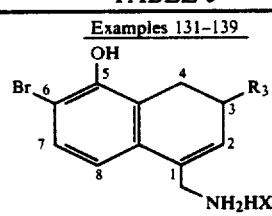

| Example # | R₃ | Carboxylic acid starting material |
|---|---|---|
| 131 | phenyl | phenylacetic acid |
| 132 | 4-bromophenyl | 4-bromophenylacetic acid |
| 133 | 3-bromophenyl | 3-bromophenylacetic acid |
| 134 | ethyl | butanoic acid |
| 135 | isopropyl | 3-methylbutanoic acid |
| 136 | n-butyl | hexanoic acid acid |
| 137 | n-hexyl | n-octanoic acid |
| 138 | cyclohexyl | cyclohexaneacetic acid |
| 139 | adamantyl | 1-adamantaneacetic acid |

EXAMPLE 140

[1R,3S]

1-Aminomethyl-3,4-dihydro-5-hydroxy-6-methoxy-3-phenyl-1H-2-benzopyran

Step 1: 2-Benzyloxy-3-methoxybenzaldehyde

A 60% dispersion of sodium hydride in mineral oil (5.26 g, 140 mmol) was washed with hexane and the hexane was removed. To the washed sodium hydride was added 75 mL of anhydrous DMF. The resultant slurry was well stirred and 21.38 g (140 mmol) of 2-hydroxy-3-methoxy benzaldehyde (commercially available from Aldrich Chemical Company) was added dropwise, over a period of 45 minutes. The mixture was stirred at 50° C. for 1 h and then 16.2 mL (140 mmol) of benzyl chloride was added in one portion. The reaction mixture was stirred at 50° C. for 3 days and then allowed to slowly (overnight) cool to ambient temperature and the reaction was quenched with 60 mL of 10% aqueous hydrochloric acid solution. The mixture was extracted with 3×250 mL of ethyl acetate and the combined ethyl acetate extracts were washed with 250 mL of aqueous sodium bicarbonate solution, water and brine, dried over anhydrous sodium sulfate, filtered and concentrated in vacuo. The residue was purified by chromatography on silica gel eluted with ethyl acetate:-hexane (1:9 v/v) to give 26.39 g (77.5%) of the title compound.

Step 2: 2-Benzyloxy-3-hydroxymethyl-1-methoxybenzene

To a well-stirred suspension of 2.0 g (52.7 mmol) of sodium borohydride in 65 mL of ethyl alcohol at 0° C. under a nitrogen atmosphere, was slowly added 15 g (61.9 mmol) of 2-benzyloxy-3-methoxybenzaldehyde, from Step 1, in 100 mL of ethyl alcohol. The reaction mixture was stirred at 0° C. for 10 minutes and then 50 mL of water was added to quench the reaction, followed by 50 mL of diethyl ether. The mixture was slowly added to 60 mL of 10% aqueous hydrochloric acid solution at 0° C. and the resultant mixture was stirred for 1 h and then extracted with 3×200 mL of diethyl ether. The combined ether extracts were washed with aqueous sodium bicarbonate solution, water and brine, dried over anhydrous sodium sulfate, filtered and concentrated in vacuo to give 15.14 g (100% yield) of the title compound as a white solid.

Step 3: 2-Benzyloxy-3-bromomethyl-1-methoxybenzene

To a solution of 15.04 g (62 mmol) of 2-benzyloxy-3-hydroxymethyl-1-methoxybenzene, from Step 2, in 140 mL of diethyl ether at 0° C. was added slowly, with stirring, 2.9 mL (31 mmol) of phosphorous tribromide. The reaction mixture was stirred at 0° C. for 30 minutes and then allowed to warm to ambient temperature over a 4 h period. The solution phase was decanted and the reaction was quenched with aqueous sodium bicarbonate solution. The layers were separated and the aqueous layer was extracted twice with diethyl ether. The combined organic layers were washed with water and brine, dried over anhydrous sodium sulfate, filtered and concentrated under reduced pressure to give 12.48 g (65% yield) of the title compound.

Step 4: 2-Benzyloxy-3-(2'-(1"3"-dithiane)-2'-(phenyl)ethyl)-1-methoxybenzene

To a solution of 4.38 g (23.3 mmol) of 2-phenyl-1,3-dithiane (commercially available from Aldrich Chemical Company) in 15 mL of THF at −78° C. under a nitrogen atmosphere, was added dropwise, 8.9 mL (22.3 mmol) of a 2.5M solution of n-butyl lithium in hexane. The resultant mixture was stirred at −78° C. for 1 h and then to it was added a solution of 6.86 g (22.3 mmol) of 2-benzyloxy-3-bromomethyl-1-methoxybenzene, from Step 3, in 70 mL of THF. The reaction mixture was allowed to warm to ambient temperature and stirred at ambient temperature for 24 h. The reaction was then quenched by the addition of 125 mL of water and the resultant mixture was stirred at ambient temperature for 1 h. The mixture was then extracted three times with ethyl acetate and the combined ethyl acetate extracts were washed with water and brine, dried over anhydrous sodium sulfate, filtered and concentrated in vacuo to give 10.99 g of the title compound, which was carried on to the next step without purification.

Step 5: 2-(2'-Benzyloxy-3'-methoxy)phenyl-1-phenylethanone

To a solution of 19.88 g (117 mmol) of silver nitrate and 13.87 g (104 mmol) of N-chlorosuccinimide in 250 mL of an 80% solution of acetonitrile in water, was added dropwise a solution of 10.99 g (26 mmol) of 2-benzyloxy-3-(2'-(1'',3''-dithiane)-2'-(phenyl)ethyl)-1-methoxybenzene, from Step 4, in acetonitrile. The reaction mixture was stirred at ambient temperature for 45 minutes and then quenched with 25 mL of saturated aqueous sodium hydrogen sulfite solution, 25 mL of saturated aqueous sodium carbonate solution and 25 mL of brine. The mixture was filtered and the filtrate was washed with 1N aqueous hydrochloric acid solution, aqueous sodium bicarbonate solution and brine, dried over anhydrous sodium sulfate, filtered and concentrated in vacuo. The residue was purified by chromatography on silica gel eluted with ethyl acetate:hexane (1:5 v/v) to give 3.27 g (38% yield) of the title compound.

Step 6: 2-(2'-Benzyloxy-3'-methoxy)phenyl-1-phenyl-1-ethanol

To a stirred solution of 230 mg (6.0 mmol) of sodium borohydride in 20 mL of ethyl alcohol, in an ice bath, was added a solution of 2.3 g (6.9 mmol) of 2-(2'-benzyloxy-3'-methoxy)phenyl-1-phenylethanone, from Step 5, in 20 mL of ethyl alcohol. The reaction mixture was stirred for 12 h at ambient temperature and then poured into 25 mL of 10% aqueous hydrochloric acid solution. The cloudy mixture was extracted with 3×75 mL of diethyl ether and the combined ether extracts were washed with aqueous sodium bicarbonate solution and brine, dried over anhydrous sodium sulfate, filtered and concentrated in vacuo to afford 1.89 g (82% yield) of the title compound.

Step 7: 2-Bromo-1-ethoxy-1-((1'-phenyl-2'-(2''-benzyloxy-3''-methoxy)phenyl)ethoxyethane Bromine (1.8 mL, 36 mmol) was added to a solution of 3.36 mL (36 mmol) of ethyl vinyl ether in 90 mL of methylene chloride at 0° C. The mixture was stirred at 0° C. for 0.5 h and then treated with 6 mL (36 mmol) of diisopropyl ethylamine, followed by 8.64 g (26.9 mmol) of 2-(2'-benyloxy-3'-methoxy)phenyl-1-phenyl-1-ethanol from Step 6. The reaction mixture was stirred for 6 h at ambient temperature and then poured into 200 mL of saturated aqueous ammonium chloride solution. The cloudy mixture was extracted with 2×250 mL of diethyl ether and the combined ether extracts were washed with water and brine, dried over anhydrous sodium sulfate, filtered and concentrated under reduced pressure. The residue was purified by chromatography on silica gel eluted with 7% diethyl ether in hexane to give 10.57 g (80% yield) of the title compound.

Step 8:[1R,3S] 5-Benzyloxy-1-bromomethyl-3,4-dihydro-6-methoxy-3-phenyl-1H-2-benzopyran A solution of 9.76 g (20.6 mmol) of 2-bromo-1-ethoxy-1-((1'-phenyl-2'-(2''-benzyloxy-3''-methoxy)-phenyl)ethoxyethane, from Step 7, in 45 mL of methylene chloride was treated at −50° C. with 5.13 mL (41 mmol) of boron trifluoride etherate and the resultant mixture was allowed to slowly warm to 0° C. over a 1 h period, and was then stirred at 0° C. for 3 h. The reaction mixture was then poured into 150 mL of saturated aqueous sodium bicarbonate solution and the cloudy mixture was extracted with 2×300 mL of diethyl ether. The combined ether extracts were washed with water and brine, dried over anhydrous sodium sulfate, filtered and concentrated in vacuo. The yellow oil was chromatographed on silica gel eluted with 5% diethyl ether in hexane to give 6.36 g (72% yield) of the title compound.

Step 9: [1R,3S] 1-Aminomethyl-5-benzyloxy-3,4-dihydro-6-methoxy-3-phenyl-1H-2-benzopyran hydrochloride Following the procedures described in Step 3 of Example 33, the product of Step 8, [1R,3S] 5-benzyloxy-1-bromomethyl-3,4-dihydro-6-methoxy-3-phenyl-1H-2-benzopyran, was converted to the title compound.

Step 10: [1R,3S] 1-Aminomethyl-3,4-dihydro-5-hydroxy-6-methoxy-3-phenyl-1H-2-benzopyran hydrochloride A solution of 940 mg (2.28 mmol) of [1R,3S] 1-aminomethyl-5-benzyloxy-3,4-dihydro--6-methoxy-3-phenyl-1H-2-benzopyran hydrochloride, from Step 9, in 500 mL of methanol was treated with 500 mg of 10% palladium on carbon and the resultant mixture was shaken under a hydrogen atmosphere for 24 h. The reaction mixture was diluted with ethyl acetate and filtered through Celite filter aid. The filtrate was concentrated in vacuo to give an off-white solid which was crystallized from methanol/methylene chloride/ether to give 488 mg (66% yield) of the title compound, m.p. 234° C.; MS DCl-NH$_3$ M/Z: 286 (M+H)$^+$. Analysis calculated for C$_{17}$H$_{20}$ClNO$_3$+0.25 CH$_2$Cl$_2$: C, 60.40; H, 6.02; N, 4.08. Found: C, 60.07; H, 5.97; N, 4.03.

EXAMPLE 141

[1R,3S] 1-Aminomethyl-3,4-dihydro-5,6-dimethoxy-3-phenyl-1H-2-benzopyran formic acid salt Step 1 2-(2',3'-Dimethoxy)phenyl-1-phenyl-1-ethanol To a solution of 8.0 g (58 mmol) of 1,2-dimethoxybenzene (veratrole) in 200 mL of dry THF at 0° C., was added sequentially, 8.7 mL (58 mmol) of tetramethylethylene diamine and 23.2 mL of a 2.5M solution of n-butyl lithium in hexane. After being stirred for 1 h at 0° C. and 4 h at ambient temperature, the resultant yellow suspension was cooled to 0° C. and then treated with 3.41 mL (30 mmol) of styrene oxide. The resultant mixture was then allowed to warm to ambient temperature, stirred for 5 h and then poured into 150 mL of 1M aqueous hydrochloric acid solution. The cloudy aqueous solution was extracted with 3×100 mL of diethyl ether. The combined ether extracts were washed with brine, dried over anhydrous sodium sulfate and concentrated in vacuo. The residue was chromatographed on silica gel eluted with 20% ethyl acetate in hexane to give 1.5 g (20% yield) of the title compound.

Step 2: [1R,3S] 1-Aminomethyl-3,4-dihydro-5,6-dimethoxy-3-phenyl-1H-2-benzopyran formic acid salt Following the procedures described in Steps 2–3 of Example 33, the hydrochloride salt of the title compound was prepared. The hydrochloride salt was chromatographed on silica gel eluted with 18:1:1 ethyl acetate:formic acid:water to give the title compound, m.p. 121° C.; MS DCl-NH$_3$ M/Z: 300 (M+H)$^+$. Analysis calculated for C₁₉H₂₃NO₅: C, 64.42; H, 6.82; N, 3.95. Found: C, 64.08; H, 6.69; N, 3.93.

EXAMPLE 142

[1R,3S] 1,3-Bis(aminomethyl)-3,4-dihydro-5-hydroxy-8-methyl-1H-2-benzopyran dihydrobromide Step 1: 1-Benzyloxy-3-(2'-methoxy-5'-methylphenyl)-2-propanol Glycidol (3.1 g, 42 mmol) is added dropwise to a suspension of sodium hydride (1.0 g, 42 mmol) in 25 mL of dry dimethyl formamide (DMF) at 0° C. After stirring the suspension for 30 min at 0° C., 7.1 g (42 mmol) of benzyl bromide is added dropwise and the reaction mixture is stirred at 0° C. for 40 min. The reaction mixture is then diluted with 75 mL of diethyl ether, transferred to a separatory funnel and washed with 2×30 mL of 2N aqueous sulfuric acid solution, 2×30 mL of water and saturated aqueous sodium bicarbonate solution. The organic solution is dried over anhydrous magnesium sulfate, filtered and concentrated under reduced pressure to give 5.3 g of the protected epoxy alcohol as an oil.

N-Butyl lithium (18.5 mL of a 2.5M solution in hexane, 46 mmol) is added to a solution of 4-methyl-anisole (4.76 mL, 39 mmol) in 75 mL of THF at 0° C. After 4 h, the protected glycidol (5.3 g, 32 mmol) in 10 mL of THF is added dropwise and the reaction mixture is allowed to warm to ambient temperature. After 1.5 h, the reaction mixture is poured into 10% aqueous ammonium chloride solution and extracted with 2×50 mL of diethyl ether. The combined ether extracts are washed with ammonium chloride solution, dried over anhydrous magnesium sulfate, filtered and concentrated in vacuo. The residue is purified by column chromatography on silica gel to give the title compound.

Step 2: [1R,3S] 3-Benzyloxymethyl-1-bromomethyl-3,4-dihydro-5-methoxy-8-methyl-1H-2-benzopyran A solution of 1-benzyloxy-3-(2'-methoxy-5'-methylphenyl)-2-propanol (3.4 g, 12 mmol), from Step 1, and bromoacetaldehyde dimethyl acetal (1.7 mL, 14 mmol) in 25 mL of methylene chloride is cooled to 0° C. Boron trifluoride etherate (3.6 mL, 29 mmol) is added dropwise and the reaction mixture is stirred for 1.5 h. The resultant dark brown solution is poured into 50 mL of 10% aqueous sodium carbonate solution and the aqueous solution is extracted with 3×50 mL of diethyl ether. The combined ether extracts are washed with saturated aqueous sodium bicarbonate solution and brine, dried over anhydrous magnesium sulfate, filtered and concentrated under reduced pressure. The residue is purified by column chromatography on silica gel to give the title compound.

Step 3: [1R,3S] 1-Bromomethyl-3,4-dihydro-3-hydroxymethyl-5-methoxy-8-methyl-1H-2-benzopyran 5% Platinum on carbon (1.0 g) is added to a solution of [1R,3S] 3-benzyloxymethyl-1-bromomethyl-3,4-dihydro-5-methoxy-8-methyl-1H-2-benzopyran (3.42 g, 8.7 mmol), from Step 2, in 150 mL of methanol and 5 mL of ethyl acetate. The reaction mixture is sealed under 4 atmospheres of hydrogen and shaken overnight. The reaction mixture is filtered to remove the catalyst and concentrated. The residue is purified by column chromatography on silica gel to give the title compound.

Step 4: [1R,3S] 1-Azidomethyl-3,4-dihydro-3-hydroxymethyl-5-methoxy-8-methyl-1H-2-benzopyran Lithium azide (1.0 g, 20 mmol) is added to a solution of [1R,3S] 1-bromomethyl-3,4-dihydro-3-hydroxymethyl-5-methoxy-8-methyl-1H-2-benzopyran (1.77 g, 5.87 mmol), from Step 3, in 20 mL of DMF. The reaction mixture is heated to 70° C. for 1.5 h then cooled to ambient temperature and poured into 50 mL of diethyl ether and 50 mL of water. The layers are separated and the aqueous layer is extracted with 2×50 mL of diethyl ether. The combined ether layers are washed with saturated aqueous sodium bicarbonate solution, dried over anhydrous magnesium sulfate, filtered and concentrated in vacuo. The residue is purified by column chromatography on silica gel to give the title compound.

Step 5: [1R,3S] 1,3-Bis(azidomethyl)-3,4-dihydro-5-methoxy-8-methyl-1H-2-benzopyran Methanesulfonyl chloride (0.128 mL, 1.65 mmol) is added dropwise to a solution of [1R,3S] 1-azidomethyl-3,4-dihydro-3-hydroxymethyl-5-methoxy-8-methyl-1H-2-benzopyran (395 mg, 1.5 mmol), from Step 4, and 0.314 mL (2.25 mmol) of triethylamine (TEA) in 15 mL of methylene chloride at 0° C. After stirring for 30 min at 0° C., the reaction mixture is transferred to a separatory funnel and diluted with diethyl ether. The layers are separated and the organic layer is washed with 2×20 mL of water, 2×15 mL of 1 N aqueous hydrochloric acid solution and brine, dried over anhydrous magnesium sulfate, filtered and concentrated under reduced pressure. The residue is dissolved in 20 mL of DMF and 440 mg (9 mmol) of lithium azide is added. The reaction mixture is heated to 80° C. and stirred at 80° C. for 4 h then cooled and poured into 50 mL of water. The aqueous solution is extracted with 3×30 mL of diethyl ether and the combined ether extracts are washed with 30 mL of water and brine, dried over anhydrous magnesium sulfate and concentrated under reduced pressure. The residue is purified on silica gel to give the title compound.

Step 6: [1R,3S] 1,3-Bis(aminomethyl)-3,4-dihydro-5-methoxy-8-methyl-1H-2-benzopyran Lithium aluminum hydride (2.4 mL of a 1.0 M solution in diethyl ether, 2.4 mmol) is added dropwise to a solution of [1R,3S] 1,3-bis(azidomethyl)-3,4-dihydro-5-methoxy-8-methyl-1H-2-benzopyran (283 mg, 1.2 mmol), from Step 5, in 10 mL of anhydrous diethyl ether at 0° C. The reaction mixture is allowed to warm to ambient temperature and stirred for 45 min. The reaction is then quenched by the sequential addition of 91 µL of water, 91 µL of 15% aqueous sodium hydroxide solution and 273 µL of water. The solution is dried over anhydrous magnesium sulfate, filtered and concentrated in vacuo to give the title compound.

Step 7: [1R,3S] 1,3-Bis(aminomethyl)-3,4-dihydro-5-hydroxy-8-methyl-1H-2-benzopyran dihydrobromide

[1R,3S] 1,3-Bis(aminomethyl)-3,4-dihydro-5-methoxy-1H-2-benzopyran from Step 6 is treated with an excess of boron tribromide as described in Step 6 of Example 145 to give the title compound.

EXAMPLE 143

[1R,3S] 1-Aminomethyl-3,4-dihydro-5-hydroxy-3-hydroxymethyl-8-methyl-1H-2-benzopyran hydrobromide Step 1: [1R,3S] 1-Aminomethyl-3,4-dihydro-3-hydroxymethyl-5-methoxy-8-methyl-1H-2-benzopyran Lithium aluminum hydride (1.1 mL of a 1.0M solution in diethyl ether, 1.1 mmol) is added dropwise to a solution of 289 mg (1.1 mmol) of [1R,3S] 1-azidomethyl- 3,4-dihydro-3-hydroxymethyl-5-methoxy-8-methyl-1H-2-benzopyran, the product of Step 4 of Example 142, in 10 mL of anhydrous diethyl ether at 0° C. The reaction mixture is allowed to warm to ambient temperature and stirred for 40 min. The reaction mixture is cooled to 0° C. and quenched by the sequential addition of 42 μL of water, 42 μL of 15% aqueous sodium hydroxide solution and 126 μL of water. The solution is dried over anhydrous magnesium sulfate and filtered. The filtrate is concentrated in vacuo to give the title compound.

Step 2:[1R,3S] 1-Aminomethyl-3,4-dihydro-5-hydroxy-3-hydroxymethyl-8-methyl-1H-2-benzopyran hydrobromide

[1R,3S] 1-Aminomethyl-3,4-dihydro-3-hydroxymethyl-5-methoxy-1H-2-benzopyran, from Step 1, is treated with an excess of boron tribromide as described in Step 6 of Example 145 to afford the title compound.

EXAMPLE 144

[1R,3S]
1-Aminomethyl-3,4-dihydro-5-hydroxy-8-methyl-3-pyrrolidinylmethyl-1H-2-benzopyran dihydrobromide Step 1: 1-Azidomethyl-3,4-dihydro-5-methoxy-8-methyl-3-pyrrolidinylmethyl-1H-2-benzopyran Methanesulfonyl chloride (0.146 mL, 1.89 mmol) is added dropwise to a solution of 0.453 g (1.72 mmol) of [1R,3S] 1-azidomethyl-3,4-dihydro-3-hydroxymethyl-5-methoxy-8-methyl-1H-2-benzopyran, the product of Step 4 of Example 142, and 0.36 mL (2.58 mmol) of triethylamine in 15 mL of methylene chloride at 0° C. The reaction mixture is stirred for 30 min at 0° C. then transferred to a separatory funnel and diluted with 45 mL of diethyl ether. The layers are separated and the organic layer is washed with 2×20 mL of water, 2×20 mL of 1 N hydrochloric acid and 20 mL of brine, dried over anhydrous magnesium sulfate, filtered and concentrated under reduced pressure. The residue is dissolved in 20 mL of N,N-dimethyl formamide (DMF) and an excess amount of pyrrolidine is added to this solution. The reaction mixture is heated at 95° C. for 2.5 h then poured into 75 mL of water. The aqueous solution is extracted with 3×40 mL of diethyl ether. The combined ether extracts are washed with 2×30 mL of water and brine, dried over anhydrous magnesium sulfate and concentrated in vacuo. The residue is purified by column chromatography on silica gel eluted to give the title compound.

Step 2: [1R,3S] 1-Aminomethyl-3,4-dihydro-5-methoxy-8-methyl-3-pyrrolidinylmethyl-1H-2-benzopyran dihydrochloride Lithium aluminum hydride (0.52 mL of a 1.0M solution, 0.52 mmol) is added dropwise to a solution of 164 mg (0.52 mmol) of [1R,3S]1-azidomethyl-3,4-dihydro-5-methoxy-8-methyl-3-pyrrolidinylmethyl-1H-2-benzopyran, from Step 1, in 10 mL of anhydrous diethyl ether at 0° C. The reaction mixture is allowed to warm to ambient temperature and it is stirred at ambient temperature for 40 min. The reaction mixture is then cooled to 0° C. and the reaction is quenched by the sequential addition of 20 μL of water, 20 μL of 15% aqueous sodium hydroxide solution and 60 μL of water. The resultant solution is dried over anhydrous magnesium sulfate and the precipitate filtered. Diethyl ether saturated with anhydrous hydrogen chloride is then added dropwise to the filtrate to obtain the hydrochloride salt of [1R,3S] 1-aminomethyl-3,4-dihydro-5-methoxy-3-pyrrylidinomethyl-1H-2-benzopyran.

Step 3: [1R,3S] 1-Aminomethy-3,4-dihydro-5-hydroxy-8-methyl-3-pyrrolidinylmethyl-1H-2-benzopyran dihydrobromide

[1R,3S] 1-Aminomethyl-3,4-dihydro-5-methoxy-8-methyl-3-pyrrylidinylmethyl-1H-2-benzopyran, from Step 2 is treated with an excess of boron tribromide as described in Step 6 of Example 145 to afford the title compound

EXAMPLE 145

[1R,3S]
5-Hydroxy-3-phenyl-1-(2'R-pyrrolidinyl)-1,2,3,4-tetrahydronaphthalene hydrobromide Step 1:1-Cyano-5-methoxy-3-phenyl-3,4-dihydronaphthalene To a suspension of 8.8 g (35 mmol) of 5-methoxy-3-phenyl-1,2,3,4-tetrahydro-1-naphthalenone, the product of Example 1, is added 7.5 g (75.6 mmol) of trimethylsilyl cyanide (commercially available from Aldrich Chemical Company) and approximately 50 mg of anhydrous aluminum chloride (AlCl$_3$). The reaction mixture is heated at 60° C. for 3 h then cooled to ambient temperature and diluted with 150 mL of toluene. The volume of the reaction mixture is reduced in vacuo to approximately 50 mL. The resultant trimethylsilyl adduct is dehydrated by treatment with 15 mL of trifluoroacetic acid and 100 mg of p-toluenesulfonic acid in 200 mL of toluene at reflux temperature for 1 h. The reaction mixture is cooled to ambient temperature, the layers separated and the organic layer washed with water, aqueous sodium bicarbonate solution and brine, dried over anhydrous magnesium sulfate, filtered and concentrated under reduced pressure to give the title compound.

Step 2:1-Cyano-5-methoxy-3-phenyl-1,2,3,4-tetrahydronaphthalene

Sodium borohydride (6.8 g) is added to a suspension of 6.1 g (23.3 mmol) of 1-cyano-5-methoxy-3-phenyl-3,4-dihydronaphthalene, from Step 1, in 100 mL of absolute ethanol and the reaction mixture is heated at reflux temperature for 1.5 h. The solvent is evaporated under reduced pressure and the residue partitioned between equal volumes of ethyl acetate and 1N aqueous hydrochloric acid solution. The layers are separated and the organic layer is washed with aqueous sodium bicarbonate solution and brine, dried over anhydrous magnesium sulfate, filtered and concentrated to give the title compound.

Step 3:5-Methoxy-3-phenyl-1,2,3,4-tetrahydro-1-naphthalene carboxylic acid

A mixture of 5.03 g (19.1 mmol) of 1-cyano-5-methoxy-3-phenyl-1,2,3,4-tetrahydronaphthalene, from Step 2, 40 mL of 5% aqueous potassium hydroxide solution and 90 mL of ethylene glycol is heated at reflux temperature for 8 h. The reaction mixture is then cooled to −20° C. and made acidic by the addition of cold concentrated aqueous hydrochloric acid solution. The acidic solution is extracted with methylene chloride and the organic extracts are washed with brine, dried over anhydrous magnesium sulfate, filtered and evaporated to give the title compound which is used in the next step without purification.

Step 4: N-Methoxy-N-methyl-5-methoxy-3-phenyl-1,2,3,4-tetrahydro-1-naphthalene carboxamide 5-Methoxy-3-phenyl-1,2,3,4-tetrahydro-1-naphthalene carboxylic acid (4.5 g, 16 mmol), from Step 3, is suspended in 100 mL of toluene and 5 mL of oxalyl chloride is added. The reaction mixture is heated at reflux temperature for 1.5 h under a nitrogen atmosphere. The solvent is evaporated to give the acid chloride. The acid chloride and 2 g (20 mmol) of N, O-dimethylhydroxylamine hydrochloride are dissolved in 80 mL of ethanol-free chloroform. The solution is cooled to 0° C. and 3.3 mL (40.8 mmol) of pyridine is added slowly. The reaction mixture is allowed to warm to ambient temperature and stirred at ambient temperature for approximately 64 h and then evaporated to dryness. The residue is partitioned between brine and a 1:1 mixture of diethyl ether and methylene chloride. The layers are separated and the organic layer dried over anhydrous magnesium sulfate, filtered and concentrated under reduced pressure to give the title compound. The product of Step 4 is used in the next step without purification.

Step 5: 5-Methoxy-3-phenyl-1-(2'R-pyrrolidinyl)-1,2,3,4-tetrahydronaphthalene hydrochloride N-Methoxy-N-methyl-5-methoxy-3-phenyl-1,2,3,4-tetrahydro-1-naphthalene carboxamide (3.3 g), from Step 4, is dissolved in 80 mL of dry THF and the solution is cooled to 0° C. An excess (3-4 equivalents) of 2,2,5,5-tetramethyl-1-aza-2,5-disilacyclopentane-1-propyl magnesium bromide (prepared as described by Basha and DeBernardis in *Tetrahedron Letters*, 25, 5271-5274 (1984)) is added and the reaction mixture is stirred overnight. The reaction mixture is recooled to 0° C., 10% hydrochloric acid solution in ethanol is added slowly, and the reaction mixture is allowed to warm to ambient temperature again. The reaction mixture is stirred at ambient temperature for 3 h and the solvent is evaporated. The residue is dissolved in 50 mL of methanol, cooled to 0° C. and the solution is treated with an excess of sodium cyanoborohydride. The reaction mixture is allowed to warm to ambient temperature and stirred at ambient temperature for 2 h. The solvent is removed in vacuo and the residue is dissolved in diethyl ether and washed with water. The layers are separated and the acidic aqueous layer is made basic and extracted with methylene chloride. The methylene chloride extract is dried over anhydrous magnesium sufate, filtered and concentrated in vacuo. The residue is purified by column chromatography on silica gel eluted with ethyl acetate:formic acid:water (18:1:1) to give, after concentration in vacuo, the individual [1R,3S,2'R] and [1R,3R,2'R] diastereomers of the title compound as their formate salts. Each diastereomer is converted to its hydrochloride salt as follows: The formate salt is dissolved in water and the aqueous solution is made basic with sodium hydroxide. The free base is extracted with methylene chloride, and the organic layer is washed with brine, dried over anhydrous magnesium sulfate, filtered and concentrated under reduced pressure. The residue is dissolved in diethyl ether and a saturated solution of hydrogen chloride in methanol is added to precipitate the hydrochloride salt.

Step 6: [1R,3S] 5-Hydroxy-3-phenyl-1-(2'R-pyrrolidinyl)-1,2,3,4-tetrahydronaphthalene hydrobromide The product of Step 5, is dissolved in 10 mL of methylene chloride and the solution is cooled to −78° C. under a nitrogen atmosphere. Boron tribromide (0.25 mL of a 1M solution in methylene chloride) is added and the reaction mixture is stirred for 3 h at −78° C. under a nitrogen atmosphere. The reaction mixture is then allowed to warm to −20° C. for 1 h, recooled to −78° C. and the reaction is quenched with 10 mL of methanol. The solution is evaporated to dryness and distilled with methanol three times to azeotrope methyl borate from the residue to give the title compound.

EXAMPLE 146

[1R,8S,9aR]1-Amino-5-hydroxy-2,3,7,8,9,9a-hexahydro-8-phenyl-phenalene hydrobromide Step 1: 1-(3'-(3'-carbomethoxy)propanoic acid)-5-methoxy-3-phenyl-3,4-dihydronaphthalene To a suspension of 3.58 g (14.2 mmol) of 5-methoxy-3-phenyl-1,2,3,4-tetrahydro-1-naphthalenone, the product of Example 1, in 5 mL of t-butyl alcohol is added, dropwise, a mixture of 13 mL (99.4 mmol) of dimethyl succinate, 9.6 g (86 mmol) of potassium t-butoxide and 65 mL of t-butyl alcohol. After 10 mL of the mixture is added, the reaction is heated to 55° C. and maintained at this temperature for the duration of the addition. When the addition is complete, the reaction is heated for an addition 60 minutes and then cooled and poured into 50 mL of ice cold 2N aqueous hydrochloric acid solution. The aqueous phase is extracted with 5×100 mL of diethyl ether. The combined organic phase is extracted with 5×100 mL of aqueous saturated sodium bicarbonate solution. The combined aqueous layers are acidified to pH 3 with 6N aqueous hydrochloric acid solution and the product is extracted with 2×200 mL of 1:1 diethyl ether:ethyl acetate. The organic phase is dried over anhydrous magnesium sulfate, filtered, and concentrated in vacuo to give the title compound.

Step 2: 1-(3'-(3'-Carbomethoxy)propanoic acid)-5-methoxy-3-phenyl-1,2,3,4-tetrahydronaphthalene To a solution of 14.6 g.(39.9 mmol) of 1-(3'-(3'-carbomethoxy)propanoic acid)-5-methoxy-3-phenyl-3,4-dihydronaphthalene, from Step 1, in 200 mL of ethyl acetate is added 3.16 g of 10% palladium supported on carbon. The reaction mixture is shaken under 4 atmospheres of hydrogen until hydrogen uptake ceases. The reaction mixture is filtered and concentrated under reduced pressure to give the title compound. The product is carried on without any further purification or characterization.

Step 3: [1R,8S,9aR] 1-Carbomethoxy-3-hydroxy-5-methoxy-8-phenyl-7,8,9,9a-tetrahydrophenalene 1-(3'-(3'-carbomethoxy)propanoic acid)-5-methoxy-3-phenyl-1,2,3,4-tetrahydronaphthalene (3.12 g, 8.5 mmol), from Step 2, is added to 11 g of polyphosphoric acid at 0° C. The ice bath is removed and the mixture is stirred at ambient temperature for 3 hours. Ice (500 g) is added and the mixture is stirred for 1 hour. The aqueous solution is extracted with 3×50 mL of 1:1 ethyl acetate:diethyl ether. The combined organic layers are washed with 50 mL of saturated aqueous sodium bicarbonate, dried over anhydrous magnesium sulfate, filtered, and concentrated under reduced pressure. The product is purified by chromatography on silica gel to afford (1R,8S,9aR)-1-carbomethoxy-5-methoxy-3-hydroxy-8-phenyl-7,8,9,9a-tetrahydrophenalene and (1S,8S,9aR)-1-carbomethoxy-5-methoxy-3-hydroxy-8-phenyl-7,8,9,9a-tetrahydrophenalene.

Step 4: [1R,8S,9aR] 1-Carbomethoxy-5-methoxy-8-phenyl-2,3,7,8,9,9a-hexahydrophenalene To a solution of 0.46 g. (1.3 mmol) of [1R,8S,9aR] 1-carbomethoxy-5-methoxy-3-hydroxy-8-phenyl-7,8,9,9a-tetrahydrophenalene, from Step 3, in 50 mL of methanol, 50 mL of ethyl acetate, and 0.1 mL of concentrated hydrochloric acid is added 0.2 g of 5% palladium supported on carbon and the mixture is shaken under 4 atmospheres of hydrogen until the hydrogen uptake ceases. The catalyst is filtered through Celite filter aid and concentrated to give the title compound, which is carried on without further purification.

Step 5: [1R,8S,9aR]-5-Methoxy-8-phenyl-2,3,7,8,9,9a-hexahydrophenalene-1-carboxylic acid Crude [1R,8S,9aR] 1-carbomethoxy-5-methoxy-8-phenyl-2,3,7,8,9,9a-hexahydrophenalene (0.8 g., 2.1 mmol), from Step 4, is dissolved in 100 mL of methanol and 8 mL of 1N aqueous sodium hydroxide is added. After stirring for 3 days at ambient temperature, the methanol is removed under reduced pressure. The residue is partitioned between 50 mL of diethyl ether and 75 mL of water. The aqueous phase is acidified to pH 2 with 6M aqueous hydrochloric acid solution and the product is extracted with 3×25 mL of 1:1 ethyl acetate:diethyl ether. The combined organic layers are washed with brine, dried over anhydrous magnesium sulfate, filtered, and concentrated in vacuo to give the title compound.

Step 6: [1R,8S,9aR] 1-Carbobenzyloxyamino-5-methoxy-8-phenyl-2,3,7,8,9,9a-hexahydrophenalene

[1R,8S,9aR] 5-Methoxy-8-phenyl-2,3,7,8,9,9a-hexahydrophenalene-1-carboxylic acid (0.74 g, 2.3 mmol), from Step 5, and triethylamine (0.32 mL, 2.3 mmol) are dissolved in 16 mL of toluene and 0.55 mL (2.5 mmol) of diphenylphosphoryl azide is added. The mixture is heated at 80° C. for 2.5 hours then 0.5 mL (4.8 mmol) of benzyl alcohol is added and heating is continued at 80° C. for an additional 3 hours and at 65° C. for 15 hours. The mixture is cooled and concentrated under reduced pressure and 25 mL of diethyl ether is added. The solution is washed with 10 mL of 1N aqueous sodium hydroxide solution and brine, dried over anhydrous magnesium sulfate, filtered, and concentrated in vacuo. The product is purified by chromatography on silica gel to give the title compound.

Step 7: [1R,8S,9aR] 1-Amino-5-methoxy-8-phenyl-2,3,7,8,9,9a-hexahydrophenalene

A suspension of 0.58 g (1.4 mmol) of [1R,8S,9aR]-1-carbobenzyloxyamino-5-methoxy-8-phenyl-2,3,7,8,9,9a-tetrahydrophenalene, from Step 6, in 50 mL of methanol and 0.1 g of 10% palladium supported on carbon is stirred under 1 atmosphere of hydrogen for 1 hour. The solid dissolves as the reaction proceeds. The palladium catalyst is removed by filtration and the solution is concentrated under reduced pressure to give the crude product which is carried on without further purification.

Step 8: [1R,8S,9aR]-1-Amino-5-hydroxy-8-phenyl-2,3,7,8,9,9a-hexahydrophenalene hydrobromide A solution of 0.34 g (1.2 mmol) of [1R,8S,9aR] 1-amino-5-methoxy-8-phenyl-2,3,7,8,9,9a-hexahydrophenalene, from Step 7, in 9 mL of methylene chloride is treated with 4.4 mL (4.4 mmol) of a 1M solution of boron tribromide in methylene chloride, added dropwise at −78° C. The reaction is warmed to ambient temperature for 1 hour and recooled to −78° C. and the reaction is quenched with 5 mL of methanol. The reaction mixture is allowed to warm to ambient temperature and stirred for 1 hour. The solvent is removed in vacuo and 5 mL of methanol is added and the solution is concentrated to remove methyl borate by azeotropic distillation to give the title compound.

EXAMPLE 147

6-Hydroxy-4-phenyl-2,3,4,5-tetrahydro-1H-benz-[e]isoindole formic acid salt

Step 1: 5-Methoxy-3-phenyl-2-thiophenyl-1,2,3,4-tetrahydro-1-naphthalenone

To a solution of 25.7 g (0.102 mol) of 5-methoxy-3-phenyl-1,2,3,4-tetrahydro-1-naphthalenone, the product of Example 1, in 240 mL of THF is added 40.4 g (0.107 mol) of phenyltrimethylammonium tribromide. After stirring at ambient temperature for 1 h, 960 mL of water is added. The solution is extracted with 3×250 mL of ethyl acetate. The combined organic phase is washed with 3×250 mL of water, 250 mL of brine, dried over anhydrous magnesium sulfate, filtered, and concentrated under reduced pressure to give an oil which is carried on without further purification or characterization.

A solution of sodium methoxide is prepared by the addition of 3.28 g. (0.143 mol) of sodium metal to 97 mL of methanol with cooling to 0° C. Thiophenol (14.6 mL, 0.143 mol) is added dropwise over 10 minutes and then the reaction mixture is stirred for an additional 10 minutes at 0° C. A solution of the above crude oil in 60 mL of THF is added dropwise over 30 minutes and the reaction is then allowed to warm to ambient temperature for 4 h. The solvents are removed in vacuo and the residue is dissolved in a mixture of 250 mL of methylene chloride and 250 mL of water. The organic phase is collected and washed with brine, dried over anhydrous sodium sulfate, filtered, and concentrated under reduced pressure to give 5-methoxy-3-phenyl-2-thiophenyl-1,2,3,4-tetrahydro-1-naphthalenone.

Step 2: 5-Methoxy-3-phenyl-2-sulfoxophenyl-3,4-dihydronaphthalene

A solution of 20.11 g (53.7 mmol) of 5-methoxy-3-phenyl-2-thiophenyl-1,2,3,4-tetrahydronaphthalenone in 320 mL of ethanol is treated with 20.03 g (0.529 mol) of sodium borohydride. The reaction mixture is heated at reflux temperature for 2 h, then cooled and 500 mL of water is added. The solvents are removed in vacuo and the residue is taken up in 500 mL of 1:1 diethyl ether:-methylene chloride and 500 mL of water. The organic layer is removed and washed with 100 mL each of water and brine, dried over anhydrous magnesium sulfate, filtered, and concentrated under reduced pressure. The crude resultant alcohol is dehydrated by the addition of 700 mL of toluene and 3.6 g. (18.9 mmol) of p-toluenesulfonic acid monohydrate and heating to reflux with azeotropic removal of water for 30 minutes. After cooling, the solution is washed with 3 × 100 mL of saturated aqueous sodium bicarbonate solution, 100 mL of water, dried over anhydrous magnesium sulfate, filtered, and concentrated in vacuo. The crude thioenolether is dissolved in 360 mL of methylene chloride. This solution is cooled to −15° C. and a solution of 12.1 g of 3-chloroperoxybenzoic acid in 160 mL of methylene chloride is added dropwise over 30 minutes. After the addition is complete, the reaction is quenched by the addition of 100 mL of aqueous saturated sodium thiosulfate. The organic layer is separated, and washed with 3×100 mL of saturated aqueous sodium bicarbonate, 100 mL of water, dried over sodium sulfate, filtered, and concentrated under reduced pressure. The product is chromatographed on silica gel to give 5-methoxy-3-phenyl-2-sulfoxophenyl-3,4-dihydronaphthalene.

Step 3: N-Trimethylsilylmethyl-benzylamine

A mixture of 264 mL (2.42 mol) of benzylamine and 97.7 g. (0.796 mol) of chloromethyltrimethylsilane was heated to 200° C. for 2.5 h and then cooled to 10° C. A 0.1M sodium hydroxide solution (400 mL) was added and the product was extracted with 3×200 mL of diethyl ether. The combined organic phase was washed with 100 mL of water, dried over anhydrous magnesium sulfate, filtered, and concentrated under reduced pressure. The product was distilled at 115°–125° C. and 5 mm of Hg to afford the title compound as a clear liquid. $^1$H NMR (CDCl$_3$) δ0.0 (s, 9H), 1.1 (br s, 1H), 2.01 (s, 2H), 3.76 (s, 2H), 7.1–7.3 (m, 5H).

Step 4: N-Methoxymethyl-trimethylsilylmethyl-benzylamine

N-trimethylsilylmethyl-benzylamine (125.4 g, 0.649 mol), from Step 3, was added dropwise, over a 10 minute period, to a solution of 69.5 mL of 37% aqueous formaldehyde at 0° C. After an additional 10 minutes, 75.2 mL of methanol was added. The solution was then saturated with solid potassium carbonate and stirred at 0° C. for 1 h. The layers were separated and the organic phase was stirred over solid potassium carbonate at ambient temperature for 18 h. The solution was filtered and fractionally distilled give a 145°–155° C. fraction as a viscous oil, identified as N-methoxymethyl-trimethylsilylmethyl-benzylamine. $^1$H NMR (CDCl$_3$) δ0.0 (s,9H), 2.13 (s,2H), 3.18 (s,3H), 3.71 (s,2H), 3.96 (2,2H), 7.1–7.3 (m,5H).

Step 5: 2-Benzyl-6-methoxy-4-phenyl-2,3,4,5-tetrahydro-1H-benzo[e]isoindole

To a solution of 1.13 g (3.13 mmol) of 5-methoxy-3-phenyl-2-sulfoxophenyl-3,4-dihydronaphthalene, from Step 2, in 10 mL of methylene chloride is added 1 g (4.21 mmol) of N-methoxymethyl-trimethylsilylmethyl-benzylamine, from Step 4, and 0.1 mL of trifluoroacetic acid. At 12 h intervals, the amine and acid additions are repeated 7 more times. The solvent is then removed under reduced pressure with heating to 100° C. and the product is purified on silica gel to give the title compound.

Step 6: 6-Methoxy-4-phenyl-2,3,4,5-tetrahydro-1H-benzo[e]isoindole hydrochloride To a solution of 0.89 g (2.52 mmol) of 2-benzyl-6-methoxy-4-phenyl-2,3,4,5-tetrahydrobenzo[e]isoindole, from Step 6, in 22 mL of 1,2-dichloroethane is added 0.11 g (0.05 mmol) of 1,8-bis(dimethylamino)-naphthalene and 0.33 mL (3.15 mmol) of 1-chloroethylchloroformate at 0° C. The solution is heated to reflux for 2 h and the solvent removed in vacuo. The residue is filtered through silica gel, eluting with 25% ethyl acetate in hexanes. After concentration under reduced pressure, methanol (20 mL) is added and the solution is heated to reflux for 30 minutes, before the solvent is removed in vacuo to give the title compound.

Step 7: 6-Hydroxy-4-phenyl-2,3,4,5-tetrahydro-1H-benzo[e]isoindole formic acid salt A suspension of 44.1 mg. (0.159 mmol) of 6-methoxy-4-phenyl-2,3,4,5-tetrahydro-1H-benzo[e]isoindole hydrochloride, from Step 6, in 2 mL of methylene chloride is cooled to −78° C. and 0.64 mL of a 1M solution of boron tribromide in methylene chloride is added. The reaction is warmed to ambient temperature for 1 h and recooled to −78° C. before 1 mL of methanol is added. After warming to ambient temperature for 1 h, the solvents are removed in vacuo. Additional methanol (5 mL) is added and removed in vacuo. The product is chromatographed on silica gel, eluting with 18:1:1 ethyl acetate:formic acid: water to give 6-hydroxy-4-phenyl-2,3,4,5-tetrahydro-1H-benzo[e]isoindole formic acid salt.

EXAMPLE 148

[1R,3S] 3,4-Dihydro-5-hydroxy-1-(N-L-norvalyl)-aminomethyl-3-phenyl-1H-2-benzopyran hydrochloride Step 1: [1R,3S] 3,4-Dihydro-5-hydroxy-1-[N-(N-t-butoxycarbonyl)-L-norvalyl]-aminomethyl-3-phenyl-1H-2-benzopyran The product of example 92 (1.68 g, 6.59 mmol) is dissolved in 20 mL of N,N-dimethylformamide and N-t-butoxycarbonyl-L-norvaline (1.49 g, 6.59 mmol) is added to the solution. The mixture is cooled to 0° C. and 1-ethyl-3-[3-(dimethylamino)propyl]-carbodiimide hydrochloride (1.4 g, 6.91 mmol) is added as a solid, followed by 1-hydroxybenzotriazole (0.93 g, 6.91 mmol). After 10 min, N-methyl morpholine (0.76 mL, 6.91 mmol) is slowly added and the mixture is stirred at 0° C. for 2 h, then overnight at ambient temperature. The reaction is quenched with 50 mL of water and extracted into ethyl acetate. The organic layer is washed with 1N phosphoric acid solution, saturated aqueous sodium bicarbonate solution, water and brine, then dried over anhydrous magnesium sulfate, filtered and concentrated in vacuo to give the crude product, which is purified by chromatography to give the title compound.

Step 2: [1R,3S] 3,4-Dihydro-5-hydroxy-1-(N-L-norvalyl)-aminomethyl-3-phenyl-1H-2-benzopyran hydrochloride The product of step 1 is dissolved in diethyl ether and the solution is saturated with hydrogen chloride (g). The mixture is stirred for 3 h then filtered and washed with diethyl ether to afford the title compound.

EXAMPLE 149

Competitive Binding

D-1 and D-2 Receptor Binding Assays

Homogenized rat caudate was incubated in the presence of [$^{125}$I]SCH-23982 (a selective antagonist of the dopamine D-1 receptor) and the compounds of this invention, according to procedures described by A. Sidhu, et al. in *European J Pharmacology*, 113: 437 (1985) and in *European J Pharmacology*, 128: 213 (1986). The compounds compete with the radiolabeled ligand for occupancy of the receptors and the molar potency of each compound was quantified. The affinity of the compound for the receptor (Ki) was calculated as described by Y. C. Cheng and W. H. Prusoff in *Biochemical Pharmacology*, 22: 3099 (1973) from the relationship $Ki=IC_{50}(1+[L]/K_D)$ where $IC_{50}$ is the concentration of test compound which produces a 50% inhibition in the specific binding of the radioligand, L; [L] is the concentration of radioligand; and $K_D$ is the affinity of the radioligand for the receptor.

The procedure for the dopamine D-2 receptor binding assay was similar to that used for the D-1 receptor assay. Homogenized rat caudate was the source of the D-2 receptors. The tissue homogenate was incubated in the presence of [$^{125}$I]-p-aminophenylethyl spiroperidol (a selective antagonist of the dopamine D-2 receptor) and the compounds being evaluated, according to the protocol described by T. Agui, N. Amlaiky, M. G. Caron and J. W. Kebabian in *Molecular Pharmacology*, 33: 163 (1988). The molar affinity of the compound for the receptor binding site was calculated by the same method used for the D-1 receptor assay, assuming a competitive interaction between the compound and the radiolabeled ligand.

The competitive binding data (Ki values) from the D-1 and D-2 receptor binding assays are shown in Table 6. The Ki values are inversely proportional to the affinity of the compound for the receptor.

TABLE 6

| Competitive Binding for D-1 and D-2 Receptors | | |
|---|---|---|
| Example # | D-1 Ki ($\mu$M) | D-2 Ki ($\mu$M) |
| 2 | 1.445 | 2.188 |
| 5 | 0.692 | 4.121 |
| 33 | 78.523 | — |
| 34 | 96.605 | 23.988 |
| 68 | 0.086 | — |
| 87 | 2.754 | 18.057 |
| 88 | 0.236 | 4.677 |
| 89 | 0.686 | 1.200 |
| 90 | 0.366 | 1.202 |
| 91 | 26.303 | 9.770 |
| 92 | 0.103 | — |
| 93 | 3.388 | — |
| 140 | 1.876 | — |
| 141 | 2.691 | 12.589 |

EXAMPLE 150

Functional Assays

The interaction of dopamine or a dopamine D-1 receptor agonist with the D-1 receptor causes a dose-dependent increase in the adenylate cyclasecatalyzed conversion of adenosine triphosphate (ATP) to cyclic adenosine monophosphate (cAMP). The functional activity of a compound was determined by assaying, in vitro, its ability to either stimulate the enzyme adenylate cyclase to produce more cAMP (agonist activity) or to antagonize a dopamine-induced increase in cAMP levels. The protocol for the adenylate cyclase assays was described by K. J. Watling and J. E. Dowling in J Neurochemistry, 36: 559 (1981) and by J. W. Kebabian, et al. in Proc Natl Acad Sci. USA, 69: 2145 (1972). In order to determine agonist activity, cell-free tissue homogenates are incubated in an ionic buffer solution containing ATP and the compound being evaluated. The tissue was obtained from either goldfish retina or rat striatum. Most of the compounds were inactive in this assay, although a few exhibited weak partial agonist activity.

In order to determine functional antagonist activity, these assays were repeated in the presence of 10 $\mu$M dopamine and increasing concentrations of the compound being evaluated. The results of the assays for antagonist activity are shown in Table 7. The Ki values were calculated as described by Y. C. Cheng and W. H. Prusoff in Biochemical Pharmacology, 22, 3099 (1973) from the relationship Ki=IC$_{50}$([S]/K$_D$). The applicability of this relationship is based on the assumption that tissues used in the assay do not have large receptor reserves for the D-1 and D-2 receptors. In this expression IC$_{50}$ is defined as the concentration of test compound which produces a 50% reduction in the response to an agonist, S; [S] is the concentration of agonist in the assay; and K$_D$ is the affinity of the agonist for the receptor.

TABLE 7

| Antagonist Activity in Adenylate Cyclase Assay | |
|---|---|
| Example # | Ki ($\mu$M) |
| 2 | 0.955 |
| 5 | 0.412 |

TABLE 7-continued

| Antagonist Activity in Adenylate Cyclase Assay | |
|---|---|
| Example # | Ki ($\mu$M) |
| 68 | 0.100 |
| 87 | 0.125 |
| 88 | 0.121 |
| 89 | 0.033 |
| 90 | 0.132 |
| 92 | 0.052 |
| 93 | 0.100 |
| 140 | 0.247 |
| 141 | 0.215 |

ROTATION BEHAVIOR

The behavioral assay used herein was based on the rat rotational model. Striatal dopamine was depleted by the intracranial injection of 6-hydroxydopamine, a neurotoxin which specifically destroys catecholaminergic neurons. The intracranial injection was conducted on anesthetized animals using standard sterotaxic techniques (U. Ungerstedt and G. W. Arbuthnott, Brain Research, 24: 485, 1970 and U. Ungerstedt, Acta Physiol. Scand. Suppl. 367, 69: 1973). This unilateral lesioning of dopamine-containing neurons causes the post synaptic dopamine receptors to become supersensitive to dopaminergic stimulation in behavioral assays. When these striatal dopamine receptors are stimulated by the test compounds, the rats rotate or physically turn, in a direction that is away from the side of their body that receives the greater dopaminergic activation due to the receptor supersensitivity. Antagonist activity was measured by the ability of the test compound to block rotation induced by stimulation by dopamine or a dopamine agonist.

Table 8 shows the rotation behavior of selected compounds of the present invention.

TABLE 8

| Example No. | Dose ($\mu$ mole/kg. s.c.*) | Number of Rotations/2 h |
|---|---|---|
| 68 | 0.1 | 227 |
| 69 | 0.1 | 1007 |

*injected subcutaneously

What is claimed is:

1. A compound having the formula:

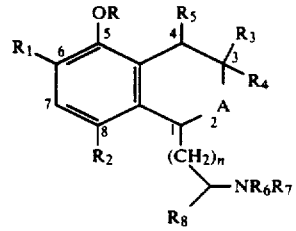

wherein
A is O,
n is 0 or 1;
R is hydrogen, lower alkyl or a prodrug ester group;
R$_1$ is selected from hydrogen, halogen, lower alkyl, C$_1$-C$_6$ haloalkyl and lower alkoxy;
R$_2$ is selected from hydrogen, halogen, lower alkyl, and C$_1$-C$_6$ haloalkyl or, taken together with R$_8$ forms a saturated fused ring of from six or seven carbon atoms;

$R_3$ is selected from
hydrogen,
alkyl of from one to twelve carbon atoms,
alkenyl of from two to twelve carbon atoms,
alkynyl of from two to twelve carbon atoms,
cycloalkyl of from three to twelve carbon atoms,
aryl wherein aryl is selected from phenyl, 1 - or 2-naphthyl, pyridyl, pyrazinyl, thiazolyl, furyl, and thienyl, optionally substituted by hydroxy, halogen, lower alkyl or lower alkoxy,
arylalkyl wherein the aryl portion is as defined above and the alkyl portion is of from one to twelve carbon atoms or,
$R_3$, taken together with $R_4$ forms a saturated spiroalkyl group of from five to seven carbon atoms or,
$R_3$, taken together with $R_5$, forms a saturated fused cycloalkyl ring of six carbon atoms;
$R_4$ is hydrogen or alkyl of from one to twelve carbon atoms;
$R_5$ is hydrogen or alkyl of from one to twelve carbon atoms;
$R_6$ is selected from hydrogen,
alkyl of from one to twelve carbon atoms,
alkenyl of from one to twelve carbon atoms,
alkynyl of from two to twelve carbon atoms,
cycloalkyl of from three to twelve carbon atoms, and
aralkyl, wherein aralkyl is as defined above, or
taken together with $R_7$ or $R_8$ forms a saturated nitrogen-containing heterocycle of from five to seven ring atoms;
$R_7$ is hydrogen or alkyl of from one to twelve carbon atoms or, taken together with $R_6$ or $R_8$ forms a saturated nitrogen-containing heterocycle of from five to seven ring atoms;
$R_8$ is hydrogen or alkyl of from one to twelve carbon atoms or, taken together with $R_6$ or $R_7$, forms a saturated nitrogen-containing heterocycle of from five to seven ring atoms, or, or
a pharaceutically acceptable salt, ester, or amide thereof;
subject to the proviso that $R_3$ and $R_4$ cannot simultaneously both be hydrogen.

2. A compound according to claim 1 in which $R_3$ is aryl, alkyl or cycloalkyl.

3. A compound according to claim 1 in which $R_3$ is phenyl or cyclohexyl.

4. A compound according to claim 1 in which $n=0$, $R_8$ is hydrogen and $NR_6R_7$ is $NH_2$ or $NHCH_3$.

5. A compound according to claim 1 in which $R_1$ is methyl or bromo.

6. A compound according to claim 1 in which R is hydrogen or a readily cleavable group.

7. A compound according to claim 1 in which n is 0; R is hydrogen or a readily cleavable group; $R_2$ is hydrogen or taken together with $R_8$ forms a fused ring; $R_4$ is hydrogen and $R_5$ is hydrogen.

8. A compound selected from the group consisting of:
[1R,3S]-1-aminomethyl-3-cyclohexyl-3,4-dihydro-5-hydroxy-6-methyl-1H-2-benzopyran;
[1R,3S]-1-(N,N-dimethylamino)methyl-3-cyclohexyl-3,4-dihydro-5-hydroxy-6-methyl -1H-2-benzopyran;
[1R,3S]-1-(N-methylamino)methyl-3-cyclohexyl-3,4-dihydro-5-hydroxy-6-methyl-1H-2-benzopyran;
[1R,3S]-1-aminomethyl-6-bromo-3,4-dihydro-5-hydroxy-3-phenyl-1H-2-benzopyran;
[1R,3R]-1-aminomethyl-6-bromo-3,4-dihydro-5-hydroxy-3-phenyl-1H-2-benzopyran;
[1R,3S]-1-aminomethyl-3,4-dihydro-5-hydroxy-3-phenyl-1H-2-benzopyran;
[1R,3R]-1-(N-methylamino)methyl-6-bromo-3,4-dihydro-5-hydroxy-3-phenyl-1H-2-benzopyran;
[1R,3S]-1-aminomethyl-3,4-dihydro-5,6-dimethoxy-3-phenyl-1H-2-benzopyran; and
[1R,3S]-1-aminomethyl-3,4-dihydro-5-hydroxy-6-methoxy-3-phenyl-1H-2-benzopyran;
or a pharmaceutically acceptable salt, ester, or amide thereof.

9. A pharmaceutical composition for selectively acting on dopaminergic receptors comprising a pharmaceutically acceptable carrier and a therapeutically effective amount of a compound as defined by claim 1.

10. A pharmaceutical composition for treating dopamine-related neurological disorders comprising a pharmaceutically acceptable carrier and a therapeutically effective amount of a compound as defined by claim 1.

11. A pharmaceutical composition for treating dopamine-related cardiovascular disorders comprising a pharmaceutically acceptable carrier and a therapeutically effective amount of a compound as defined by claim 1.

12. A pharmaceutical composition for treating addictive behavior disorders comprising a pharmaceutically acceptable carrier and a therapeutically effective amount of a compound as defined by claim 1.

13. A method for selectively acting on dopaminergic receptors comprising administering to a patient in need, a therapeutically effective amount of a compound as defined by claim 1.

14. A method for treating dopamine-related neurological disorders characterized by abnormal dopaminergic activity comprising administering to a patient in need a therapeutically acceptable amount of a compound as defined by claim 1.

15. A method for treating dopamine-related cardiovascular disorders comprising administering to a patient in need a therapeutically effective amount of a compound as defined by claim 1.

16. A method for treating addictive behavior disorders comprising administering to a patient in need a therapeutically effective amount of a compound as defined by claim 1.

* * * * *